US010105948B2

(12) United States Patent
Ueshima

(10) Patent No.: US 10,105,948 B2
(45) Date of Patent: Oct. 23, 2018

(54) IMAGE INSPECTION DEVICE, IMAGE INSPECTION METHOD, PROGRAM, AND INK JET PRINTING SYSTEM

(71) Applicant: FUJIFILM Corporation, Tokyo (JP)

(72) Inventor: Masashi Ueshima, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/715,173

(22) Filed: Sep. 26, 2017

(65) Prior Publication Data

US 2018/0086049 A1 Mar. 29, 2018

(30) Foreign Application Priority Data

Sep. 27, 2016 (JP) ................................ 2016-188700

(51) Int. Cl.

*B41J 2/045* (2006.01)
*B41J 2/21* (2006.01)
*B41J 29/393* (2006.01)
*G01N 21/892* (2006.01)
*H04N 1/00* (2006.01)

(52) U.S. Cl.

CPC ......... *B41J 2/0451* (2013.01); *B41J 2/04586* (2013.01); *B41J 2/2139* (2013.01); *B41J 29/393* (2013.01); *G01N 21/8921* (2013.01); *H04N 1/00029* (2013.01)

(58) Field of Classification Search

CPC .... B41J 2/0451; B41J 2/0456; B41J 2/04586; B41J 2/135; B41J 2/2139; B41J 2/2142; G01N 21/8921; H04N 1/00029

See application file for complete search history.

(56) References Cited

U.S. PATENT DOCUMENTS 6,130,685 A * 10/2000 Matsubara ............. B41J 19/147 347/41
6,504,625 B1 * 1/2003 Amero .................. B41J 2/2135 358/1.9

(Continued)

FOREIGN PATENT DOCUMENTS

EP 2626210 8/2013
JP 5111216 1/2013

(Continued)

OTHER PUBLICATIONS

"Search Report of Europe Counterpart Application", dated Mar. 8, 2018, p. 1-p. 7.

*Primary Examiner* — Anh T. N. Vo
(74) *Attorney, Agent, or Firm* — JCIPRNET

(57) ABSTRACT

An image inspection device analyzes data of a first read image obtained by reading a defective nozzle detection pattern which is recorded in a first region of a recording medium by a single pass ink jet printing apparatus to detect a defective nozzle of a line-type ink jet head used to record the defective nozzle detection pattern and stores a history of the detection result of the defective nozzle in a history information storage unit. The image inspection device analyzes data of a second read image of a printed image recorded in a second region of the recording medium to detect an image defect of the printed image and collates information about the detected image defect with history information stored in the history information storage unit to specify a defective nozzle causing the image defect.

18 Claims, 35 Drawing Sheets

(56) References Cited

U.S. PATENT DOCUMENTS

| | | | | |
|---|---|---|---|---|
| 6,862,414 | B2 * | 3/2005 | Sampath | G03G 15/5062 382/112 |
| 8,118,389 | B2 | 2/2012 | Sasayama | |
| 8,567,896 | B2 | 10/2013 | Ueshima | |
| 8,801,130 | B2 | 8/2014 | Nishida et al. | |
| 8,851,619 | B2 | 10/2014 | Ueshima | |
| 2007/0070111 | A1 | 3/2007 | Vladislav | |
| 2012/0154477 | A1 * | 6/2012 | Yamazaki | B41J 2/2139 347/19 |
| 2013/0187970 | A1 * | 7/2013 | Inoue | B41J 2/12 347/14 |

FOREIGN PATENT DOCUMENTS

| | | |
|---|---|---|
| JP | 2013069003 | 4/2013 |
| JP | 5457307 | 4/2014 |
| JP | 5597680 | 10/2014 |
| JP | 2015179090 | 10/2015 |

* cited by examiner

| | | NOZZLE NUMBER | | | | | | | | | | | | | | | | |
|---|---|---|---|---|---|---|---|---|---|---|---|---|---|---|---|---|---|---|
| PAGE NUMBER | DETECTED COLOR | 0 | 1 | 2 | ........ | m-4 | m-3 | m-2 | m-1 | m | m+1 | m+2 | m+3 | m+4 | ........ | N-2 | N-1 | N |
| Page1 | Magenta | | | | | | | | DETECTED | | | | | | | | | |
| Page2 | Black | DETECTED | | | | | DETECTED | | | | | | | | | | | |
| Page3 | Cyan | | | DETECTED | | DETECTED | | | | | DETECTED | | | | | | DETECTED | |
| Page4 | Yellow | | | | | | | | DETECTED | | | | | DETECTED | | | | DETECTED |
| Page5 | Magenta | | | | | | | | | | | | | | | | | |
| ....... | | | | | | | | | | | | | | | | | | |
| Page Latest-8 | Black | | | DETECTED | | DETECTED | | | | | | | | | | | DETECTED | |
| Page Latest-7 | Cyan | | | | | | | | | | | | DETECTED | | | | | |
| Page Latest-6 | Yellow | | | | | | DETECTED | | DETECTED | | | | | | | DETECTED | | |
| Page Latest-5 | Magenta | DETECTED | | | | | | | | | | | | | | | | |
| Page Latest-4 | Black | | | | | | | | DETECTED | | | | | DETECTED | | | | |
| Page Latest-3 | Cyan | | DETECTED | | | | | | | | | | DETECTED | | | | | DETECTED |
| Page Latest-2 | Yellow | | | | | | | | | | DETECTED | | | | | | DETECTED | |
| Page Latest-1 | Magenta | | | | | | DETECTED | | | | | | | | | | | |
| Page Latest | Black | DETECTED | | DETECTED | | | | | DETECTED | | | | | | | | | |

| PAGE NUMBER | DETECTED COLOR | NOZZLE NUMBER | | | | | | | | | | | | | | | | |
|---|---|---|---|---|---|---|---|---|---|---|---|---|---|---|---|---|---|---|
| | | 0 | 1 | 2 | ....... | m-4 | m-3 | m-2 | m-1 | m | m+1 | m+2 | m+3 | m+4 | ....... | N-2 | N-1 | N |
| Page1 | Magenta | | | | | | | | DETECTED | | | | | | | | | |
| Page2 | Black | DETECTED | | | | | DETECTED | | | | | | | | | | | |
| Page3 | Cyan | | | DETECTED | | DETECTED | | | | | DETECTED | | | | | | DETECTED | |
| Page4 | Yellow | | | | | | | | DETECTED | | | | | DETECTED | | | | DETECTED |
| Page5 | Magenta | | | | | | | | | | | | | | | | | |
| ....... | | | | | | | | | | | | | | | | | | |
| Page Latest-8 | Black | | | DETECTED | | DETECTED | | | | | | | | | | | DETECTED | |
| Page Latest-7 | Cyan | | | | | | | | | | | | DETECTED | | | | | |
| Page Latest-6 | Yellow | | | | | | DETECTED | | DETECTED | | | | | | | DETECTED | | |
| Page Latest-5 | Magenta | DETECTED | | | | | | | | | | | | | | | | |
| Page Latest-4 | Black | | | | | | | | DETECTED | | | | | DETECTED | | | | |
| Page Latest-3 | Cyan | | DETECTED | | | | | | | | | | DETECTED | | | | | DETECTED |
| Page Latest-2 | Yellow | | | | | | | | | | DETECTED | | | | | | DETECTED | |
| Page Latest-1 | Magenta | | | | | | DETECTED | | | | | | | | | | | |
| Page Latest | Black | DETECTED | | DETECTED | | | | | DETECTED | | | | | | | | | |

162B

164

162A

IMAGE INSPECTION DEVICE, IMAGE INSPECTION METHOD, PROGRAM, AND INK JET PRINTING SYSTEM

CROSS-REFERENCE TO RELATED APPLICATIONS

The present application claims priority under 35 U.S.C. § 119 to Japanese Patent Application No. 2016-188700, filed on Sep. 27, 2016. The above application is hereby expressly incorporated by reference, in its entirety, into the present application.

BACKGROUND OF THE INVENTION

1. Field of the Invention

The present invention relates to an image inspection device, an image inspection method, a program, and a printing system, and more particularly, to an image inspection technique that detects abnormality in the quality of an image printed by a single pass ink jet printing apparatus.

2. Description of the Related Art

In the field of digital printing which is one of image formation techniques, an ink jet printing apparatus that performs drawing using a single pass method has been put to practical use. A single pass printing method using ink jetting is referred to as a single pass ink jet method. In the single pass ink jet method, a line-type ink jet head in which a plurality of nozzles are arranged at high density relatively scans a recording medium only one time to complete the recording of an image in the scanning region.

In the single pass ink jet method, when liquid droplets jetted from a nozzle of the ink jet head fly in a curved line or when the nozzle is in a non-jetting state, streak unevenness occurs in a corresponding portion of a printed image. The streak unevenness is an image defect that appears as streak-shaped shading. The streak-shaped image defect is referred to as a streak defect.

In order to prevent the streak defect, measures, such as a process of specifying a defective nozzle and performs image quality correction corresponding to the state of the defective nozzle, are required. For example, a non-jetting correction technique which disables a defective nozzle and supplements recording using neighboring nozzles has been known as an example of the image quality correction process. JP5457307B discloses a non-jetting correction technique.

In addition, a technique which prints a test chart called a ladder pattern and performs image analysis for the printing result of the ladder pattern has been known as a technique for specifying a defective nozzle. The ladder pattern is a line pattern in which lines drawn by each nozzle, which are formed by performing so-called "1-on n-off" jetting control for a nozzle column of an ink jet head such that each nozzle continuously jets liquid droplets, are arranged.

JP2013-069003A discloses a technique that performs image analysis for data of a read image, which is obtained by reading the printing result of a ladder pattern using an image reading device, such as a charge-coupled device (CCD) sensor, to specify a defective nozzle. The technique for specifying a defective nozzle disclosed in JP2013-069003A can check the position of the defective nozzle and the details of the defective state. As a result, it is possible to accurately perform image quality correction for the defective nozzle.

As a technique for detecting the occurrence of a streak defect from a printed image, JP2015-179090A discloses a method that determines whether a streak defect occurs in a printed matter on the basis of a difference value between sample image information and inspection target image information, which is obtained by reading an image included in the printed matter obtained by a printing operation of a printing apparatus, using a reading unit. The reading unit disclosed in JP2015-179090A is construed as the term corresponding to an "image reading device" in the specification.

According to the technique disclosed in JP2015-179090A, it is possible to rapidly determine whether a streak defect occurs in a printed image of a printed matter with high accuracy.

SUMMARY OF THE INVENTION

However, the technique for specifying a defective nozzle disclosed in JP2013-069003A has the following problems.

[Problem 1]

There is no guarantee that, when a defective nozzle is detected from the printing result of the ladder pattern, a streak defect will occur in a corresponding portion of the user image which is designated as a printing target by a print job during continuous printing. For example, even when curved flight occurs a little, for example, because the amount of ink used for the portion corresponding to the defective nozzle is small, the curved flight is less likely to affect the visibility of a streak defect.

From the viewpoint of the quality of a printed matter required by the user, when the degree of streak defect is small, the streak defect is likely to be allowed as the image quality of the printed matter. In this case, when a defective nozzle is detected on the basis of strict standards and a process of determining whether the printing quality of the printed matter is poor is performed or an image quality correction process for the defective nozzle is performed, there is a concern that productivity will be reduced. In addition, excessive image quality correction is performed. As a result, there is a concern that the corrected image quality will be degraded.

[Problem 2]

In a case in which a defective nozzle is detected during continuous printing, the defective nozzle detection ladder pattern is printed a blank portion which is a region outside the region in which the user image is drawn in the recording medium. Since the area of the region in which the ladder pattern is drawn is limited to the blank portion, it is difficult to print the ladder pattern corresponding to all colors and all nozzles of the ink jet heads of each ink color provided in the ink jet printing apparatus on one page. Therefore, in a case in which a defective nozzle is detected during continuous printing, the ladder pattern is divided and printed on a plurality of recording media. For example, the ladder patterns corresponding to each ink color are printed on different pages. As a result, it takes time to specify a defective nozzle during continuous printing. In addition, since it takes time to specify a defective nozzle, it is difficult to perform image quality correction in time and the number of waste sheets with a printing failure increases.

The technique for determining whether a streak occurs which is disclosed in JP2015-179090A has the following problem.

[Problem 3]

The technique disclosed in JP2015-179090A can determine whether a streak defect occurs in the printed user image, but is not capable of specifying a defective nozzle causing the streak defect. This is because the reading resolution of an image reading device, such as a scanner for reading the printing result, is lower than the recording resolution defined by the nozzle density of the ink jet head.

In a case in which an image reading device with a resolution lower than the recording resolution is used, it is possible to narrow down the approximate position of the defective nozzle and the approximate color generated by the defective nozzle from streak information in the printed image. However, the technique disclosed in JP2015-179090A is not capable of definitely narrow down a specific defective nozzle in a defective state, unlike the technique disclosed in P2013-069003A. Therefore, it is difficult to accurately perform image quality correction for the defective nozzle on the basis of the streak information obtained by the technique disclosed in JP2015-179090A.

The present disclosure has been made in view of the above-mentioned problems and an object of the present disclosure to provide an image inspection device, an image inspection method, a program, and an ink jet printing system that can solve at least one of the above-mentioned plurality of problems.

In order to achieve the object, the following aspects of the invention are provided.

According to a first aspect of the present disclosure, there is provided an image inspection device comprising: a read image acquisition unit that acquires data of read images obtained by reading a defective nozzle detection pattern which is recorded in a first region of a recording medium by a single pass ink jet printing apparatus and a printed image which is recorded in a second region different from the first region in the recording medium by the ink jet printing apparatus, using an image reading device; a defective nozzle detection processing unit that analyzes data of a first read image, which is the read image of the defective nozzle detection pattern, to detect a defective nozzle of a line-type ink jet head used to record the defective nozzle detection pattern; a history information storage unit that stores a history of a detection result of the defective nozzle obtained by the defective nozzle detection processing unit; an image defect detection processing unit that analyzes data of a second read image, which is the read image of the printed image, to detect an image defect of the printed image; and a defective nozzle specification processing unit that collates information about the image defect detected by the image defect detection processing unit with history information stored in the history information storage unit to specify a defective nozzle causing the image defect.

According to the image inspection device of the first aspect, when it is detected that an image defect has occurred in the printed image recorded on the recording medium, the defective nozzle causing the image defect is specified. Therefore, it is possible to prevent a defective nozzle specification process from being unnecessarily performed in a situation in which no image defect is detected and to effectively perform image inspection with high accuracy.

According to a second aspect, in the image inspection device according to the first aspect, during continuous printing in which the ink jet printing apparatus continuously prints a plurality of printed images of one or more types, a process of acquiring the data of the read image, a process of detecting the defective nozzle, a process of storing the history of the detection result of the defective nozzle, a process of detecting the image defect, and a process of specifying the defective nozzle may be performed.

According to a third aspect, in the image inspection device according to the first aspect or the second aspect, the defective nozzle specification processing unit may perform a process of specifying the defective nozzle from the history information, using at least one of estimation information of an ink color obtained by estimating an ink color causing the image defect from color analysis for the information about the image defect detected by the image defect detection processing unit, estimation information of an approximate nozzle number obtained by estimating an approximate nozzle number of a nozzle causing the image defect from coordinate analysis for the information about the image defect detected by the image defect detection processing unit, or time information indicating a time when the image defect is detected by the image defect detection processing unit occurs.

According to a fourth aspect, in the image inspection device according to the third aspect, the defective nozzle specification processing unit may comprise: an ink color estimation unit that performs the color analysis for the information about the image defect detected by the image defect detection processing unit to estimate the ink color causing the image defect; an approximate nozzle number estimation unit that performs the coordinate analysis for the information about the image defect detected by the image defect detection processing unit to estimate the approximate nozzle number of the nozzle causing the image defect; a history data collation unit that extracts one or more data items including the latest data among the data items of the detection result of the defective nozzle of the ink color estimated by the ink color estimation unit from the history information, on the basis of the estimation information of the estimated ink color, and extracts data of the detection result of the defective nozzle in a range of nozzles with a plurality of consecutive nozzle numbers including the approximate nozzle number estimated by the approximate nozzle number estimation unit from the history information; and a defective nozzle determination unit that specifies the defective nozzle from the data extracted by the history data collation unit.

According to a fifth aspect, the image inspection device according to any one of the first to fourth aspects may further comprise an information providing unit that, after the process of detecting the image defect and the process of specifying the defective nozzle are performed, visualizes information indicating the processing results and provides the information to a user. The information providing unit may provide one or more information items among an output image which is output by the ink jet printing apparatus, image defect visualization information obtained by visualizing an image defect portion detected by the image defect detection processing unit on the output image, information indicating a portion in which the image defect occurs, information indicating the time when the image defect occurs, and information indicating a specification result of the defective nozzle by the process of specifying the defective nozzle.

According to a sixth aspect, in the image inspection device according to any one of the first to fifth aspects, the image defect may be a streak defect extending in a scanning direction which is a direction in which the ink jet head and the recording medium are moved relative to each other when recording is performed by a single pass method.

According to a seventh aspect, there is provided an ink jet printing system comprising: a single pass ink jet printing apparatus; an image reading device that is provided in the ink jet printing apparatus; a control device that controls an operation of the ink jet printing apparatus; and the image inspection device according to any one of the first to sixth aspects.

According to an eighth aspect, the ink jet printing system according to the seventh aspect may further comprise a correction processing unit that, in a case in which a defective nozzle causing the image defect is specified, performs an image quality correction process of preventing the image defect caused by the defective nozzle.

According to the eighth aspect, it is possible to effectively perform the specification of an accurate defective nozzle and the image quality correction process. In addition, according to the eighth aspect, when an image defect is detected, it is possible to early apply the image quality correction process and to prevent the excessive execution of the image quality correction process.

According to a ninth aspect, in the ink jet printing system according to the seventh aspect of the eighth aspect, in a case in which the defective nozzle has not been specified by a process of the defective nozzle specification processing unit during continuous printing in which the ink jet printing apparatus continuously prints a plurality of printed images of one or more types, the control device may control an interrupt process of outputting a test chart during the continuous printing, using an interrupt.

According to a tenth aspect, in the ink jet printing system according to the ninth aspect, at least one of the test charts output by the interrupt process may be a defective nozzle specification chart including a line pattern for specifying the defective nozzle. The control device may reflect an analysis result of data of a third read image, which is obtained by reading the output defective nozzle specification chart using the image reading device, in a process of printing the printed image during the continuous printing after the test chart is output by the interrupt process.

According to an eleventh aspect, in the ink jet printing system according to the ninth aspect or the tenth aspect, at least one of the test charts output by the interrupt process may be a chart formed by a composite image obtained by incorporating a test chart into one or more types of printed images which are scheduled to be output during the continuous printing.

According to a twelfth aspect, the ink jet printing system according to the eleventh aspect may further comprise: a first image processing unit that applies first image processing to at least one of the one or more types of printed images scheduled to be output during the continuous printing to generate image data subjected to the first image processing; a second image processing unit that applies second image processing to data of a test chart for interrupt output to generate image data subjected to the second image processing; and an image combination processing unit that applies an image combination process to the image data subjected to the first image processing and the image data subjected to the second image processing to generate composite image data.

According to a thirteenth aspect, the ink jet printing system according to the twelfth aspect may further comprise a test chart generation unit that generates data of the test chart for interrupt output, on the basis of detection information of the image defect detected by the image defect detection processing unit.

According to a fourteenth aspect, in the ink jet printing system according to the twelfth aspect or the thirteenth aspect, the content of the first image processing may be different from the content of the second image processing.

According to a fifteenth aspect, in the ink jet printing system according to any one of the ninth to fourteenth aspects, at least one of the test charts output by the interrupt process may be an adjustment chart for adjusting a correction parameter that is used for an image correction process of preventing a streak defect which is the image defect. The control device may reflect an analysis result of data of a fourth read image, which is obtained by reading the output adjustment chart using the image reading device, in the process of printing the printed image during the continuous printing after the test chart is output by the interrupt process.

According to a sixteenth aspect, in the ink jet printing system according to any one of the ninth to fifteenth aspects, the content of a first image quality correction process which is applied to the printed image to be output after the specification of the defective nozzle succeeds in a case in which the specification of the defective nozzle causing the image defect has succeeded and prevents the image defect may be different from the content of a second image quality correction process which is applied to the printed image to be output after the specification of the defective nozzle succeeds in a case in which the specification of the defective nozzle causing the image defect has failed and prevents the image defect.

According to a seventeenth aspect, there is provided an image inspection method comprising: a read image acquisition step of acquiring data of read images obtained by reading a defective nozzle detection pattern which is recorded in a first region of a recording medium by a single pass ink jet printing apparatus and a printed image which is recorded in a second region different from the first region in the recording medium by the ink jet printing apparatus, using an image reading device; a defective nozzle detection processing step of analyzing data of a first read image, which is the read image of the defective nozzle detection pattern, to detect a defective nozzle of a line-type ink jet head used to record the defective nozzle detection pattern; a history information storage step of storing a history of a detection result of the defective nozzle obtained in the defective nozzle detection processing step in a history information storage unit; an image defect detection processing step of analyzing data of a second read image, which is the read image of the printed image, to detect an image defect of the printed image; and a defective nozzle specification processing step of collating information about the image defect detected in the image defect detection processing step with history information stored in the history information storage unit to specify a defective nozzle causing the image defect.

In the seventeenth aspect, the same matters as those specified by the second to sixteenth aspects can be appropriately combined with each other. In this case, elements, such as processing units in charge of the processes or operations specified in the image inspection device, can be construed as elements of steps of the processes or operations corresponding thereto.

According to an eighteenth aspect, there is provided a program that causes a computer to perform: a read image acquisition step of acquiring data of read images obtained by reading a defective nozzle detection pattern which is recorded in a first region of a recording medium by a single pass ink jet printing apparatus and a printed image which is recorded in a second region different from the first region in the recording medium by the ink jet printing apparatus, using an image reading device; a defective nozzle detection processing step of analyzing data of a first read image, which is the read image of the defective nozzle detection pattern, to detect a defective nozzle of a line-type ink jet head used to record the defective nozzle detection pattern; a history information storage step of storing a history of a detection result of the defective nozzle obtained in the defective nozzle detection processing step in a history information storage unit; an image defect detection processing step of analyzing data of a second read image, which is the read image of the printed image, to detect an image defect of the printed image; and a defective nozzle specification processing step of collating information about the image defect detected in the image defect detection processing step with history information stored in the history information storage unit to specify a defective nozzle causing the image defect.

In the eighteenth aspect, the same matters as those specified by the second to sixteenth aspects can be appropriately combined with each other. In this case, elements, such as processing units in charge of the processes or operations specified in the image inspection device, can be construed as elements of the functions of a program that causes a computer to perform steps of the processes or operations corresponding thereto.

According to the invention, in a case in which an image defect is detected from a printed image, a defective nozzle is specified. Therefore, it is possible to effectively specify the defective nozzle.

BRIEF DESCRIPTION OF THE DRAWINGS

FIG. 13 is a conceptual diagram illustrating an example of a defective nozzle detection result history database.

FIG. 14 is a diagram schematically illustrating an example of a method for specifying a defective nozzle using the defective nozzle detection result history database in a case in which a streak is detected by the streak detection process.

DESCRIPTION OF THE PREFERRED EMBODIMENTS

Hereinafter, embodiments of the invention will be described in detail with reference to the accompanying drawings.

<<Example of Configuration of Ink Jet Printing Apparatus>>

Figure 1:
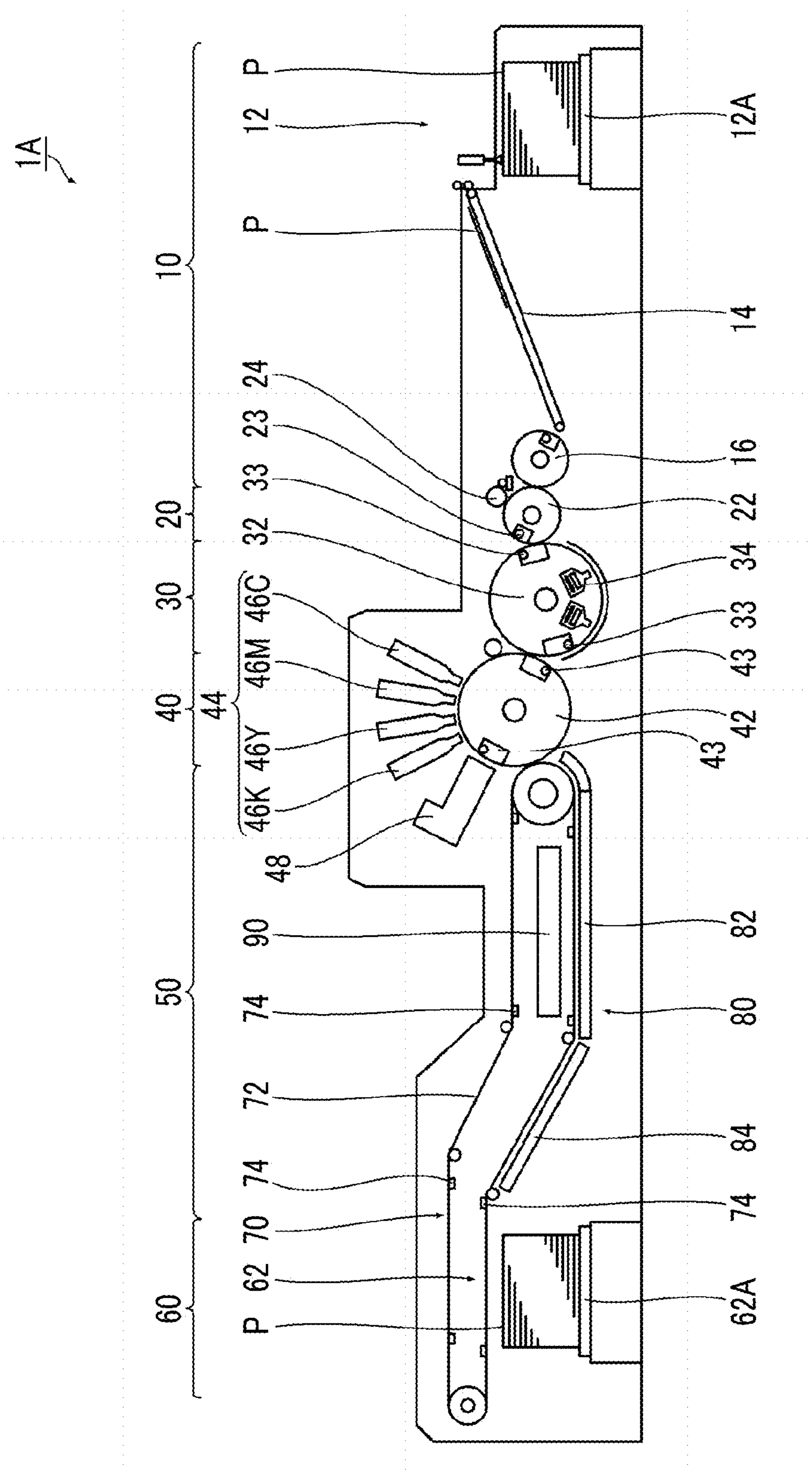
FIG. 1 is a diagram illustrating the overall configuration of an ink jet printing apparatus according to an embodiment.

FIG. 1 is a diagram illustrating the overall configuration of an example of an ink jet printing apparatus 1A according to an embodiment. The ink jet printing apparatus 1A is a single pass ink jet color digital printing apparatus that includes line-type ink jet heads 46C, 46M, 46Y, and 46K as a print head of a drawing unit 40 and prints a desired image on a sheet P, which is a flat sheet, with four color inks, such as cyan (C), magenta (M), yellow (Y), and black (K) inks, using a single pass method.

The ink jet printing apparatus 1A includes a sheet feed unit 10, a treatment liquid applying unit 20, a treatment liquid drying unit 30, a drawing unit 40, an ink drying unit 50, and a stacking unit 60.

The sheet feed unit 10 feeds the sheets P one by one. The sheet feed unit 10 includes a sheet feed device 12, a feeder board 14, and a sheet feed drum 16. The sheets P are stacked in a bundle on a sheet feed base 12A. The type of sheet P is not particularly limited. For example, cellulose-based printing sheets, such as a high-quality sheet, a coated sheet, and an art sheet, can be used. The sheet P is an example of a recording medium on which an image is recorded.

The sheet feed device 12 takes out the sheets P which are set in a bundle on the sheet feed base 12A one by one from the top and feeds the sheets to the feeder board 14. The feeder board 14 transports the sheet P received from the sheet feed device 12 to the sheet feed drum 16.

The sheet feed drum 16 receives the sheet P fed from the feeder board 14 and transports the received sheet P to the treatment liquid applying unit 20.

The treatment liquid applying unit 20 applies a treatment liquid to the sheet P. The treatment liquid is a liquid having a function of agglutinating, insolubilizing, or thickening color material components in ink. The treatment liquid applying unit 20 includes a treatment liquid applying drum 22 and a treatment liquid applying device 24.

The treatment liquid applying drum 22 receives the sheet P from the sheet feed drum 16 and transports the received sheet P to the treatment liquid drying unit 30. The treatment liquid applying drum 22 includes a gripper 23 provided on a circumferential surface. The treatment liquid applying drum 22 is rotated with the leading end of the sheet P held by the gripper 23 such that the sheet P is wound around the circumferential surface and is transported.

The treatment liquid applying device 24 applies the treatment liquid onto the sheet P transported by the treatment liquid applying drum 22. The treatment liquid is applied by a roller.

The treatment liquid drying unit 30 dries the sheet P having the treatment liquid applied thereon. The treatment liquid drying unit 30 includes a treatment liquid drying drum 32 and a warm air blower 34. The treatment liquid drying drum 32 receives the sheet P from the treatment liquid applying drum 22 and transports the received sheet P to the drawing unit 40. The treatment liquid drying drum 32 includes grippers 23 provided on a circumferential surface. The treatment liquid drying drum 32 is rotated with the leading end of the sheet P held by the grippers 23 to transport the sheet P.

The warm air blower 34 is provided inside the treatment liquid drying drum 32. The warm air blower 34 blows warm air to the sheet P transported by the treatment liquid drying drum 32 to dry the treatment liquid.

The drawing unit 40 includes a drawing drum 42, a head unit 44, and an image reading device 48. The drawing drum 42 receives the sheet P from the treatment liquid drying drum 32 and transports the received sheet P to the ink drying unit 50. The drawing drum 42 includes grippers 43 provided on a circumferential surface and is rotated with the leading end of the sheet P held by the grippers 43 such that the sheet P is wound around the circumferential surface and is transported. The drawing drum 42 includes a suction mechanism (not illustrated), sucks the sheet P wound around the circumferential surface to the circumferential surface, and transports the sheet P. A negative pressure is used for the suction. The drawing drum 42 includes a plurality of suction holes provided in the circumferential surface and draws air to the inside of the drawing drum 42 through the suction holes to suck the sheet P to the circumferential surface of the drawing drum 42.

The head unit 44 includes the ink jet heads 46C, 46M, 46Y, and 46K. The ink jet head 46C is a recording head that jets droplets of cyan (C) ink. The ink jet head 46M is a recording head that jets droplets of magenta (M) ink. The ink jet head 46Y is a recording head that jets droplets of yellow (Y) ink. The ink jet head 46K is a recording head that jets droplets of black (K) ink. Ink is supplied to each of the ink jet heads 46C, 46M, 46Y, and 46K from ink tanks (not illustrated) which are ink supply sources of corresponding colors through pipe lines (not illustrated).

Each of the ink jet heads 46C, 46M, 46Y, and 46K is a line head that can print an image on the sheet P transported by the drawing drum 42, using one scanning operation, that is, a single pass method. The ink jet heads 46C, 46M, 46Y, and 46K are arranged such that each nozzle surface faces the circumferential surface of the drawing drum 42. The ink jet heads 46C, 46M, 46Y, and 46K are arranged at regular intervals along the transport path of the sheet P by the drawing drum 42.

A plurality of nozzles which are ink jetting ports are two-dimensionally arranged on a nozzle surface of each of the ink jet heads 46C, 46M, 46Y, and 46K, which is not illustrated. The "nozzle surface" means a jetting surface in which the nozzles are formed and is synonymous with terms, such as an "ink jetting surface" and a "nozzle formation surface". The two-dimensional arrangement of the plurality of nozzles is referred to as a "two-dimensional nozzle array".

Each of the ink jet heads 46C, 46M, 46Y, and 46K can be formed by connecting a plurality of head modules in the width direction of the sheet. Here, the width direction of the sheet indicates the width of the sheet in a direction perpendicular to the transport direction of the sheet P. Each of the ink jet heads 46C, 46M, 46Y, and 46K is a line-type recording head including nozzle columns that can record an image in the entire recording region of the sheet P at a prescribed recording resolution in the width direction of the sheet perpendicular to the transport direction of the sheet P, using one scanning operation. The recording head is also called a "full-line recording head" or a "page-wide head".

The prescribed recording resolution may be a recording resolution that is set in advance by the ink jet printing apparatus 1A or may be a recording resolution which is selected and set by the user or a recording resolution which is automatically selected and set by a program corresponding to the print mode. The recording resolution can be, for example, 1200 dpi. The "dpi" means dots per inch and is a unit indicating the number of dots per inch. One inch is 25.4 millimeters [mm].

In some cases, the width direction of the sheet perpendicular to the transport direction of the sheet P is referred to as a nozzle column direction of the line head and the transport direction of the sheet P is referred to as a direction perpendicular to a nozzle column.

In the case of an ink jet head having the two-dimensional nozzle array, a projected nozzle column obtained by projecting (orthographic projection) each nozzle in the two-dimensional nozzle array in the nozzle column direction can be considered to be equivalent to a column of nozzles which are arranged at substantially regular intervals at a nozzle density for achieving the maximum recording resolution in the nozzle column direction. The "substantially regular intervals" mean that dots that can be recorded by the ink jet printing apparatus are arranged at substantially regular intervals. For example, the concept of "regular intervals" includes a case in which the intervals between the nozzles are slightly different from each other, considering the movement of the droplets on the medium due to errors in manufacture and/or landing interference. The projected nozzle column corresponds to a substantial nozzle column. Considering the projected nozzle column, nozzle numbers indicating the positions of the nozzle can be associated with each nozzle in the order of the projected nozzles arranged in the nozzle column direction.

The arrangement of the nozzles in each of the ink jet heads 46C, 46M, 46Y, and 46K is not limited and various nozzle arrays can be used. For example, instead of the two-dimensional matrix array, a linear array, a V-shaped nozzle array, and a polygonal-line nozzle array, such as a W-shaped array in which the V-shaped array, which is a unit array, is repeated, can be used.

Ink droplets are jetted from at least one of the ink jet heads 46C, 46M, 46Y, and 46K to the sheet P transported by the drawing drum 42 and the jetted droplets are attached to the sheet P. In this way, an image is recorded on the sheet P.

The drawing drum 42 functions as means for moving the sheet P relative to the ink jet heads 46C, 46M, 46Y, and 46K. The drawing drum 42 corresponds to an example of relative movement means for moving the sheet P relative to the ink jet heads 46C, 46M, 46Y, and 46K. The jetting time of each of the ink jet heads 46C, 46M, 46Y, and 46K is synchronized with a rotary encoder signal obtained from a rotary encoder provided in the drawing drum 42. The rotary encoder is not illustrated in FIG. 1 and is illustrated as a rotary encoder 152 in FIG. 2. The jetting time is the time when ink droplets are jetted and is synonymous with a droplet drop time.

In this example, four ink colors, that is, C, M, Y, and K are used. However, a combination of the ink colors and the number of colors is not limited to this embodiment. For example, light ink, dark ink, and special color ink may be added as necessary. For example, an ink jet head that jets ink of light colors, such as light cyan and light magenta, may be added or an ink jet head that jets ink of special colors, such as green and orange, may be added. Furthermore, the arrangement order of the ink jet heads of each color is not particularly limited.

The image reading device 48 is a device that optically reads the image recorded on the sheet P by the ink jet heads 46C, 46M, 46Y, and 46K and generates electronic image data indicating the read image. The image reading device 48 includes an imaging device that capture the image recorded on the sheet P and converts the image into an electric signal indicating image information. The image reading device 48 may include an illumination optical system that illuminates a reading target and a signal processing circuit that processes the signal obtained from the imaging device and generates digital image data, in addition to the imaging device.

It is preferable that the image reading device 48 has a structure capable of reading a color image. In this example, the image reading device 48 uses a color CCD linear image sensor as the imaging device. The CCD is an abbreviation of charge-coupled device and indicates a charge-coupled device. The color CCD linear image sensor is an image sensor in which light-receiving elements including color filters corresponding to red (R), green (G), and blue (B) are arranged in a line. A color CMOS linear image sensor may be used instead of the color CCD linear image sensor. The CMOS is an abbreviation of complementary metal oxide semiconductor and indicates a complementary metal oxide semiconductor.

The image reading device 48 reads the image on the sheet P while the sheet P is transported by the drawing drum 42. In some cases, the image reading device which is provided on the sheet transport path is referred to as an "in-line scanner" or an "in-line sensor". In addition, the image reading device 48 may be a camera.

When the sheet P on which the image has been recorded by at least one of the ink jet heads 46C, 46M, 46Y, and 46K passes through a reading region of the image reading device 48, the image on the sheet P is read. Examples of the image recorded on the sheet P include a user image which is a print target designated by a print job, a defective nozzle detection pattern for inspecting the jetting state of each nozzle, a printing density correction test pattern, a printing density unevenness correction test pattern, and other various test patterns.

A printed image is inspected on the basis of image data read by the image reading device 48 and it is determined whether there is an error in image quality. In addition, information about the density of an image or a jetting failure in the ink jet heads 46C, 46M, 46Y, and 46K is obtained on the basis of the image data read by the image reading device 48.

The ink drying unit 50 dries the sheet P on which the image has been recorded by the drawing unit 40. The ink drying unit 50 includes a chain gripper 70, a sheet guide 80, and a warm air blowing unit 90.

The chain gripper 70 receives the sheet P from the drawing drum 42 and transports the received sheet P to the stacking unit 60. The chain gripper 70 includes a pair of endless chains 72 that travel along a prescribed travel path and transports the sheet P along the prescribed travel path, with the leading end of the sheet P held by grippers 74 included in the pair of chains 72. A plurality of grippers 74 are provided in the chains 72 at regular intervals.

The sheet guide 80 is a member that guides the transport of the sheet P by the chain gripper 70. The sheet guide 80 includes a first sheet guide 82 and a second sheet guide 84. The first sheet guide 82 guides the sheet P transported through a first transport section of the chain gripper 70. The second sheet guide 84 guides the sheet transported through a second transport section behind the first transport section. The warm air blowing unit 90 blows warm air to the sheet P transported by the chain gripper 70.

The stacking unit 60 includes a stacking device 62 that receives and stacks the sheet P transported from the ink drying unit 50 by the chain gripper 70. The chain gripper 70 releases the sheet P at a predetermined stacking position. The stacking device 62 includes a stacking tray 62A, receives the sheets P released from the chain gripper 70, and stacks the sheets P on the stacking tray 62A in a bundle. The stacking unit 60 corresponds to a sheet discharge unit.

[Outline of Configuration of System]

Figure 2:
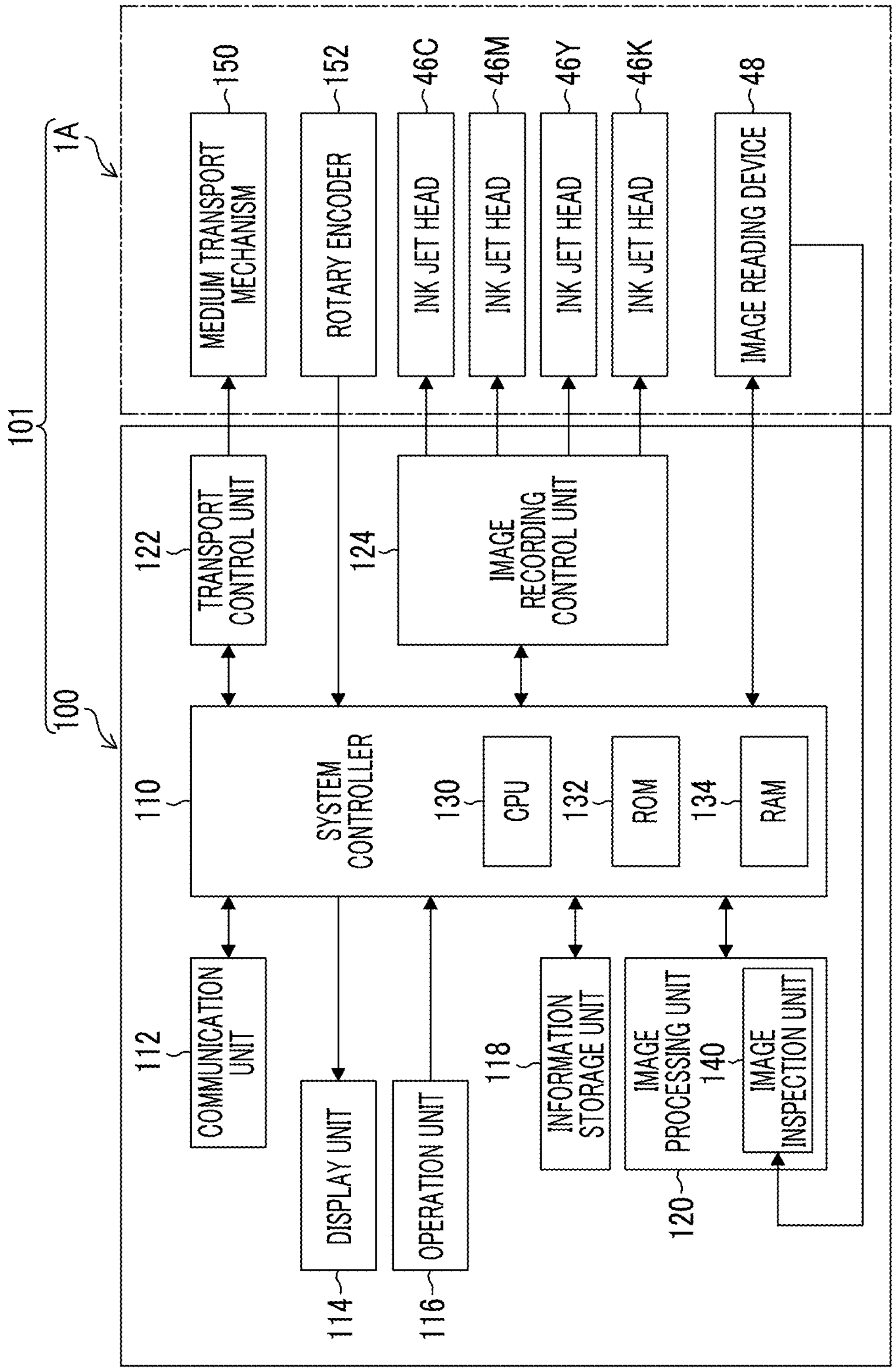
FIG. 2 is a block diagram illustrating the configuration of a main portion of a control system of the ink jet printing apparatus.

FIG. 2 is a block diagram illustrating the configuration of a main portion of a control system of the ink jet printing apparatus 1A. The ink jet printing apparatus 1A is controlled by a control device 100. A system including the control device 100 and the ink jet printing apparatus 1A is referred to as an ink jet printing system 101.

The control device 100 includes a system controller 110, a communication unit 112, a display unit 114, an operation unit 116, an information storage unit 118, an image processing unit 120, a transport control unit 122, and an image recording control unit 124. The control device 100 can be implemented by one computer or a plurality of computers. That is, the control device 100 can be formed by a combination of hardware and software of the computer. Software is synonymous with a program. In addition, some or all of the processing functions of the control device 100 may be implemented by an integrated circuit typified by a digital signal processor (DSP) or a field-programmable gate array (FPGA).

The system controller 110 functions as control means for controlling the overall operation of each unit of the ink jet printing apparatus 1A and also functions as arithmetic means for performing various arithmetic processes. The system controller 110 includes a central processing unit (CPU) 130, a read-only memory (ROM) 132, and a random access memory (RAM) 134 and operates according to a predetermined program.

The ROM 132 stores programs executed by the system controller 110 and various kinds of data required for control. The RAM 134 stores various kinds of data required for the process of the CPU 130.

The information storage unit 118 is, for example, a hard disk drive. The information storage unit 118 stores various programs executed by the CPU 130 and various kinds of data required for processes and operations.

The communication unit 112 includes a necessary communication interface. The ink jet printing apparatus 1A is connected to a host computer (not illustrated) through the communication unit 112 and can transmit and receive data to and from the host computer. There, the "connection" means a relationship capable of transmitting information and may be contact connection or non-contact connection. Examples of the connection include contact connection between corresponding terminals, wired connection, wireless connection, optical communication connection, and appropriate combinations thereof. In addition, the connection includes network connection through an electric communication line (not illustrated). The communication unit 112 may be provided with a buffer memory for increasing a communication rate. The communication unit 112 functions as an image input interface unit for acquiring image data indicating the image to be printed.

The display unit 114 and the operation unit 116 function as a user interface. Display devices using various display methods, such as a liquid crystal display and an organic electro-luminescence (EL) display, can be used as the display unit 114. Various input devices, such as a keyboard, a mouse, a touch panel, and a trackball, can be used as the operation unit 116. In addition, the operation unit 116 may be an appropriate combination thereof. The display unit 114 and the operation unit 116 may be integrally provided. For example, a touch panel may be provided on a screen of the display unit 114.

For example, an operation of inputting information and commands to the control device 100 can be performed through the operation unit 116 and the display unit 114. The user can perform, for example, an operation of inputting various kinds of information, such as printing conditions, other settings, and accessory information, an operation of selecting an image quality mode, an operation of editing accessory information, and an operation of searching for information, using the operation unit 116, while viewing content displayed on the screen of the display unit 114. In addition, the user can check various kinds of information other than input content through the content displayed on the display unit 114.

The display unit 114 functions as error information notification means for notifying error information. For example, in a case in which a streak defect is detected from a printed matter, streak defect detection information indicating streak defect detection information is displayed on the screen of the display unit 114.

The control device 100 may include a media interface unit (not illustrated). The media interface unit reads information from an external storage medium (not illustrated) and writes information to the external storage medium. Portable media, such as an optical disc and a memory card, can be used as the external storage medium. The media interface unit functions as an image input interface unit for acquiring image data indicating the image to be printed.

The image processing unit 120 performs various kinds of processing, such as a conversion process, a correction process, and halftone processing, for the image data to be printed. The conversion process includes, for example, pixel number conversion, gradation conversion, and color conversion. The correction process includes density correction and non-jetting correction for preventing an image defect caused by a defective nozzle from being seen. The image processing unit 120 performs various kinds of processing for an input image to generate output image data.

The image processing unit 120 includes an image inspection unit 140. The image inspection unit 140 performs a process of analyzing data of the read image obtained from the image reading device 48 to detect image quality abnormality. In addition, the image inspection unit 140 performs a process of analyzing data of the read image obtained from the image reading device 48 to detect a defective nozzle. The control device 100 including the image inspection unit 140 corresponds to an example of an image inspection device.

The function of the image processing unit 120 may be provided as a function block in the control device 100 including the system controller 110 or may be implemented by a computer other than the system controller 110. In addition, some or all of various processing functions of the image processing unit 120 may be implemented by an integrated circuit typified by a digital signal processor (DSP) or a field-programmable gate array (FPGA).

The transport control unit 122 controls a medium transport mechanism 150 of the ink jet printing apparatus 1A. The medium transport mechanism 150 includes the entire mechanism of the sheet transport unit related to the transport of the sheet P from the sheet feed unit 10 to the stacking unit 60 described in FIG. 1. The medium transport mechanism 150 includes, for example, the sheet feed drum 16, the treatment liquid applying drum 22, the treatment liquid drying drum 32, the drawing drum 42, the chain gripper 70 illustrated in FIG. 1. The medium transport mechanism 150 includes a driving unit including a motor and a motor driving circuit as a power source (not illustrated).

The transport control unit 122 controls the medium transport mechanism 150 in response to a command from the system controller 110 such that the sheet P is transported from the sheet feed unit 10 to the stacking unit 60.

The ink jet printing apparatus 1A includes a rotary encoder 152 as means for detecting the rotation angle of the drawing drum 42 in the medium transport mechanism 150. The jetting timing of each of the ink jet heads 46C, 46M, 46Y, and 46K is controlled according to a jetting timing signal which is generated from a rotary encoder signal output from the rotary encoder 152.

The image recording control unit 124 controls the ink jetting operation of each of the ink jet heads 46C, 46M, 46Y, and 46K in response to commands from the system controller 110. The image recording control unit 124 controls the jetting operation of each of the ink jet heads 46C, 46M, 46Y, and 46K such that an image is recorded on the sheet P, on the basis of dot data of each ink color generated through the halftone processing of the image processing unit 120.

Before an image inspection function according to this embodiment is described, the outline and task of a technique for specifying a defective nozzle and a streak detection technique for detecting a streak defect from a printed image in a single pass ink jet printing apparatus will be described.

<<For Streak Defect of Single Pass Ink Jet Printing Apparatus>>

Figure 3:
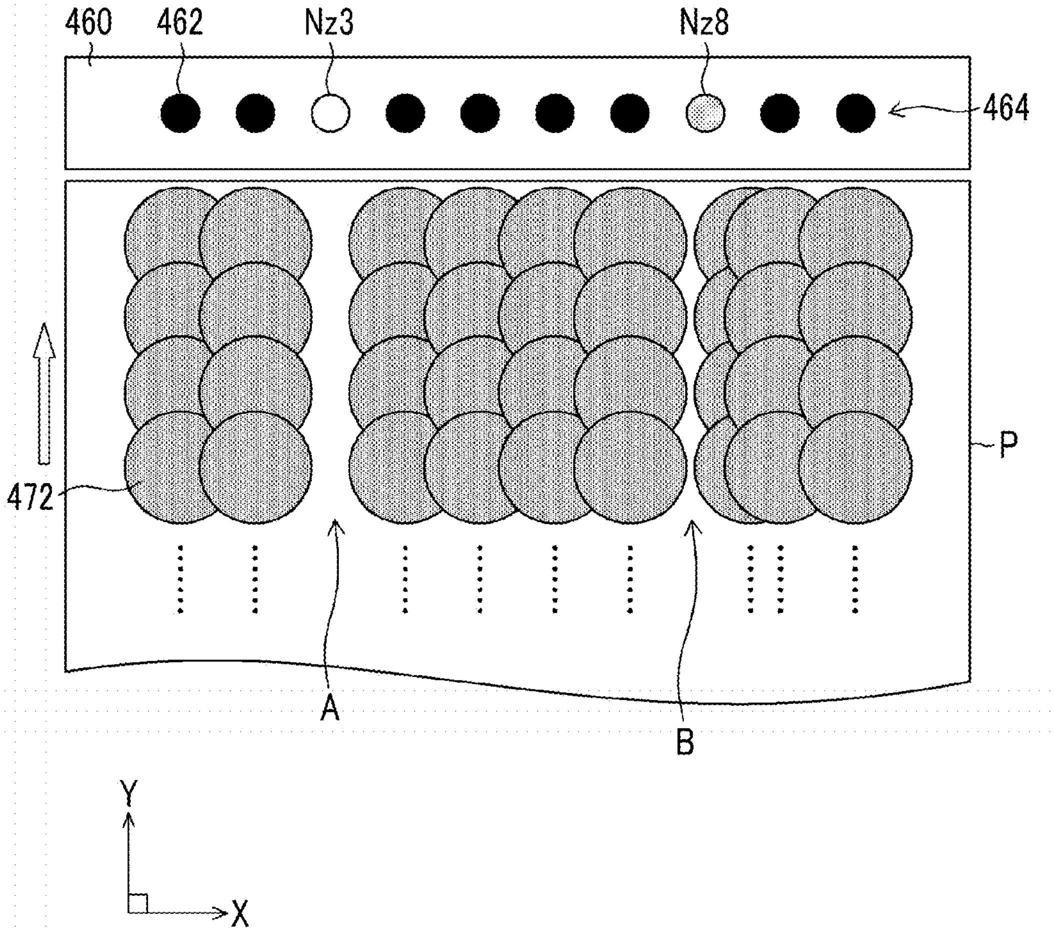
FIG. 3 is a diagram schematically illustrating a streak defect caused by a defective nozzle in a single pass ink jet printing apparatus.

FIG. 3 is a diagram schematically illustrating a streak defect caused by a defective nozzle in the single pass ink jet printing apparatus. As illustrated in FIG. 3, the single pass ink jet printing apparatus is an ink jet printing apparatus including a line head. In FIG. 3, for simplicity of explanation, an example in which a monochromatic gray image is drawn by one line head 460 will be described.

The line head 460 is an ink jet head having a nozzle column 464 in which a plurality of nozzles 462 jetting ink in an ink jet manner are arranged. The sheet P is transported with respect to the line head 460 and ink droplets are jetted from the nozzles 462. Then, the ink droplets are attached to the sheet P and dots 472 are recorded.

It is assumed that a medium transport direction in which the sheet P is transported with respect to the line head 460 is the Y direction and a sheet width direction which is the width direction of the sheet P perpendicular to the Y direction is the X direction. The plurality of nozzles 462 of the line head 460 are arranged in the X direction and each nozzle 462 records dots at different positions of the sheet P in the X direction. In some cases, the X direction in which the nozzles 462 are arranged is referred to as a nozzle column direction.

The medium transport direction is a direction in which the line head 460 relatively scans the sheet P. In some case, the medium transport direction is referred to as a scanning direction. In some cases, the X direction is referred to as a scanning orthogonal direction. The Y direction is an example of a relative movement direction. The Y direction is an example of a first direction and the X direction is an example of a second direction. Here, the sheet P is transported with respect to the line head 460 such that they are moved relative to each other. However, the line head 460 may be moved in the scanning direction with respect to the sheet P such that the line head 460 and the sheet P are moved relative to each other.

FIG. 3 illustrates the nozzle column 464 in which 10 nozzles 462 are arranged. As an example of the defective nozzle, a third nozzle Nz3 that is the third from the left of FIG. 3 is a non-jetting nozzle. In addition, the curved flight of ink droplets occurs in an eighth nozzle Nz8 that is the eighth from the left. The non-jetting nozzle is a nozzle that is not capable of jetting ink. The "non-jetting" is synonymous with "being incapable of jetting". The "defective nozzle" may be substituted with an "abnormal nozzle".

The curved flight is a phenomenon in which the jetting direction of a liquid droplet deviates and the position where a dot is to be actually formed deviates from an ideal position where the dot is to be formed. The ideal position where the dot is to be formed is a target position in terms of the design and indicates a dot formation position which is assumed in a case in which a normal nozzle jets liquid droplets. The curved flight is also referred to as "curved jetting".

In the case of the situation illustrated in FIG. 3, a streak defect that extends in the Y direction occurs at a position A on the sheet P corresponding to the position of the third nozzle Nz3 which is a defective nozzle. In addition, a streak defect that extends in the Y direction occurs at a position B on the sheet P corresponding to the position of the eighth nozzle Nz8 which is a defective nozzle. The streak defect is synonymous with "streak unevenness" or a "streak-shaped defect". In the specification, in some cases, the streak defect is simply referred to as a "streak". Examples of the streak defect include a continuous streak and an intermittent streak.

In the single pass ink jet printing apparatus that moves the sheet P relative to the line head 460 and records an image with a prescribed recording resolution using one scanning operation, a streak that extends in the scanning direction occurs in a printed image due to a defective nozzle.

<<Outline of Technique for Specifying Defective Nozzle Using Ladder Pattern>>

Figure 4:
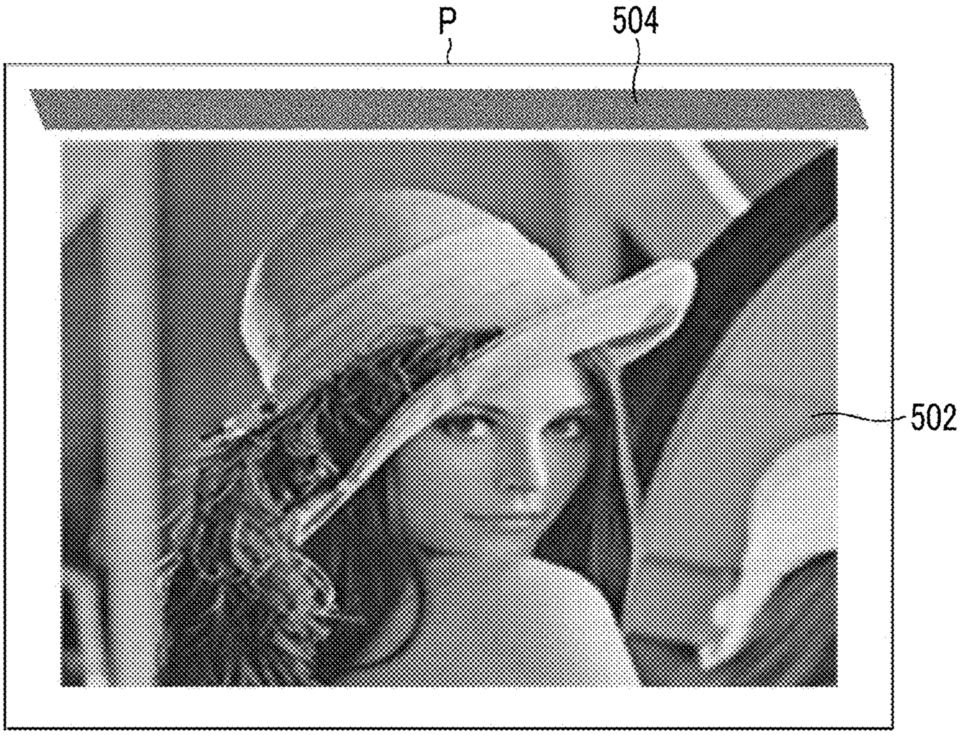
FIG. 4 is a diagram illustrating an example of an output image including a ladder pattern.

There is a method that performs image analysis for the printing result of a ladder pattern as one of the techniques for specifying a defective nozzle. FIG. 4 is a diagram illustrating an example of an output image including a ladder pattern. FIG. 4 illustrates an example in which a user image 502 and a ladder pattern 504 are drawn on the sheet P. In FIG. 4, for convenience of illustration, only a drawing region of the ladder pattern 504 is illustrated. A detailed example of the pattern is illustrated in FIG. 5.

The ladder pattern 504 illustrated in the example of FIG. 4 is added to the leading end of the user image 502 and is drawn together with the user image 502 on the same sheet P. Here, FIG. 4 illustrates an example in which the ladder pattern 504 corresponding to one color is drawn on one sheet P. The leading end of the user image 502 indicates a leading end in the travel direction of the sheet P which is the sheet transport direction in a region that is close to the end of the user image 502. The ladder pattern may be added to the rear end of the user image 502 or may be added to both the leading end and the rear end. The rear end of the user image 502 indicates a rear end in a direction opposite to the travel direction of the sheet P which is the sheet transport direction in the region that is close to the end of the user image 502. On the sheet P which is a recording medium, a region in which the ladder pattern 504 is drawn corresponds to an example of a first region. On the sheet P which is a recording medium, a region in which the user image 502 is drawn corresponds to an example of a second region.

Output Example 1 of Ladder Pattern

Figure 5:
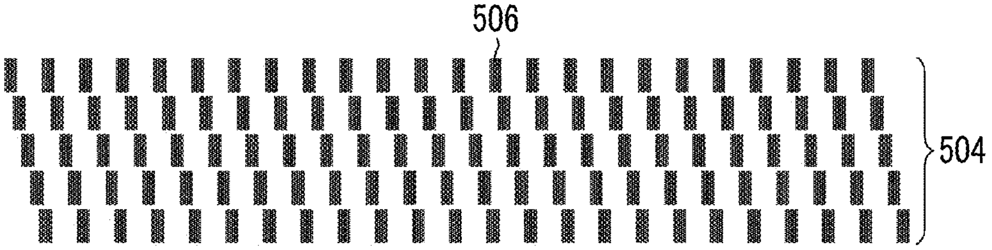
FIG. 5 is an enlarged view illustrating a portion of the ladder pattern.

FIG. 5 is an enlarged view illustrating a portion of the ladder pattern 504. The ladder pattern 504 is a so-called "1-on n-off" pattern. FIG. 5 illustrates a "1-on 4-off" pattern in a case in which n is 4. In addition, n is not limited to 4 and can be set to an appropriate integer on the basis of the relationship between the nozzle density of the ink jet head and the reading resolution of the image reading device. The ladder pattern 504 is an example of a pattern for detecting a defective nozzle. The pattern for detecting a defective nozzle is referred to as a "defective nozzle detection pattern".

The ladder pattern 504 is a line pattern in which lines 506, which are segments independently recorded by each nozzle of a line-type ink jet head, are arranged.

Output Example 2 of Ladder Pattern

Figure 6:
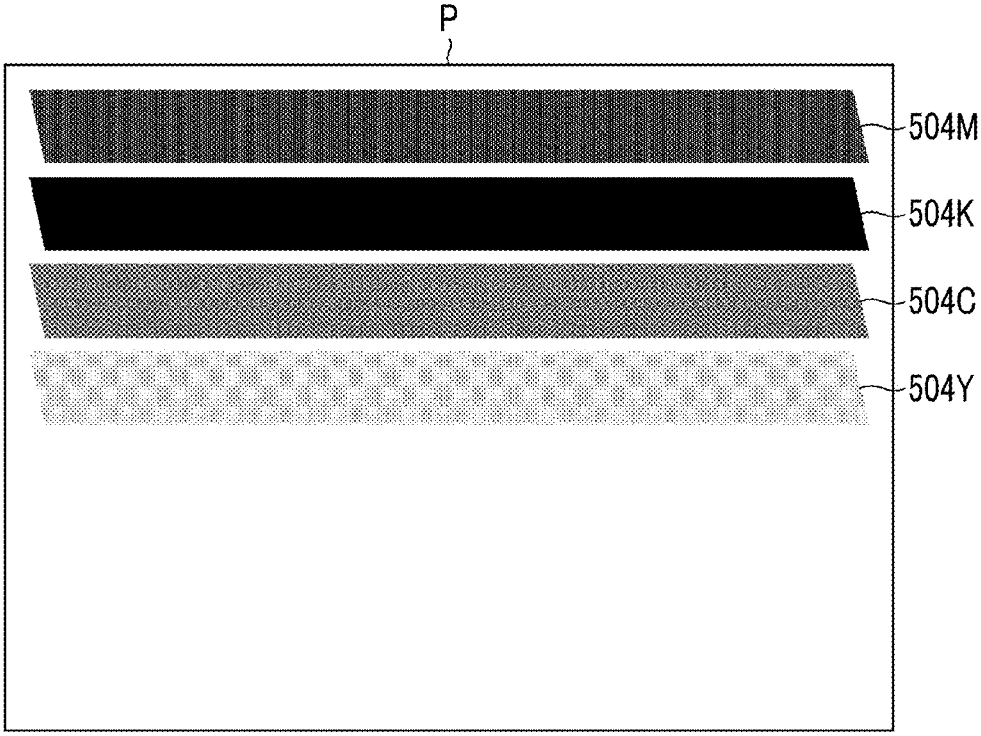
FIG. 6 is a diagram illustrating an example of a case in which a ladder pattern corresponding to all colors and all nozzles is drawn.

FIG. 6 is a diagram illustrating an example in which ladder patterns corresponding to all colors and all nozzles are collectively drawn. FIG. 6 illustrates an example in which a magenta ladder pattern 504M, a black ladder pattern 504K, a cyan ladder pattern 504C, and a yellow ladder pattern 504Y are collectively drawn on one sheet P.

In the case of a structure in which an ink jet printing apparatus using ink of four colors, that is, C, M, Y, and K includes line heads corresponding to C, M, Y, and K, ladder patterns corresponding to all of four colors, that is, C, M, Y, and K are drawn as illustrated in FIG. 6. In FIG. 6, for convenience of illustration, only the drawing regions of the ladder patterns of each color are illustrated. A detailed example of the patterns is illustrated in FIG. 7.

Figure 7:
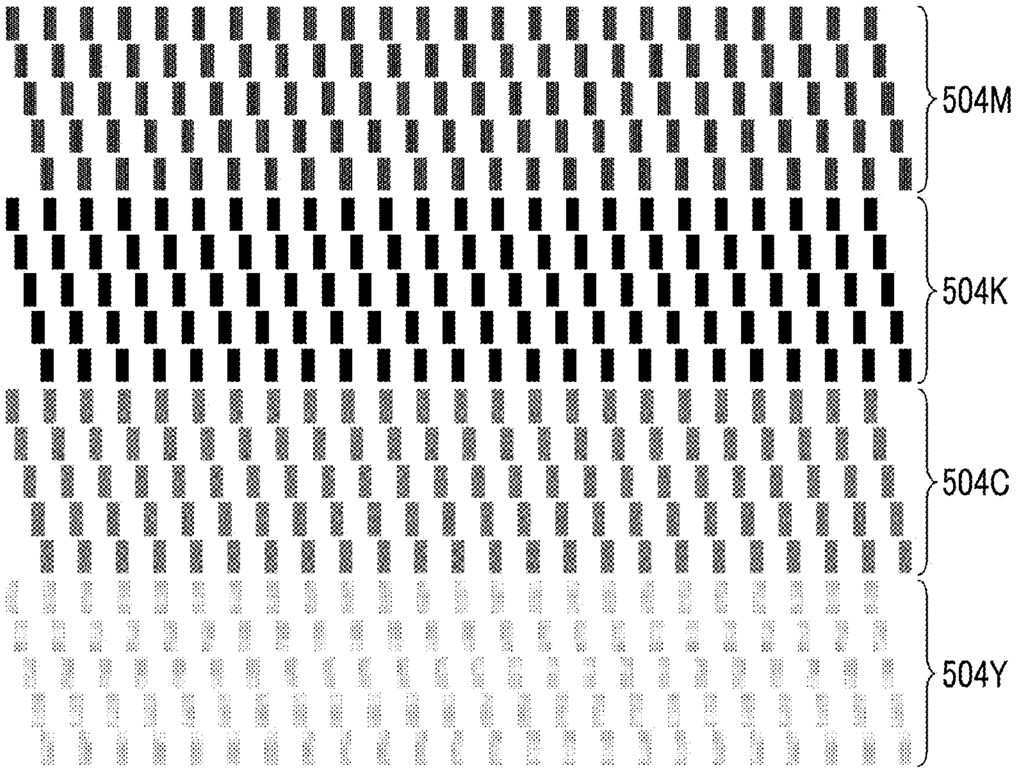
FIG. 7 is an enlarged view illustrating a portion of the ladder patterns of each color illustrated in FIG. 6.

FIG. 7 is an enlarged view illustrating a portion of the ladder patterns 504M, 504K, 504C, and 504Y of each color illustrated in FIG. 6.

[Description of Method for Specifying Defective Nozzle During Continuous Printing]

Figure 8:
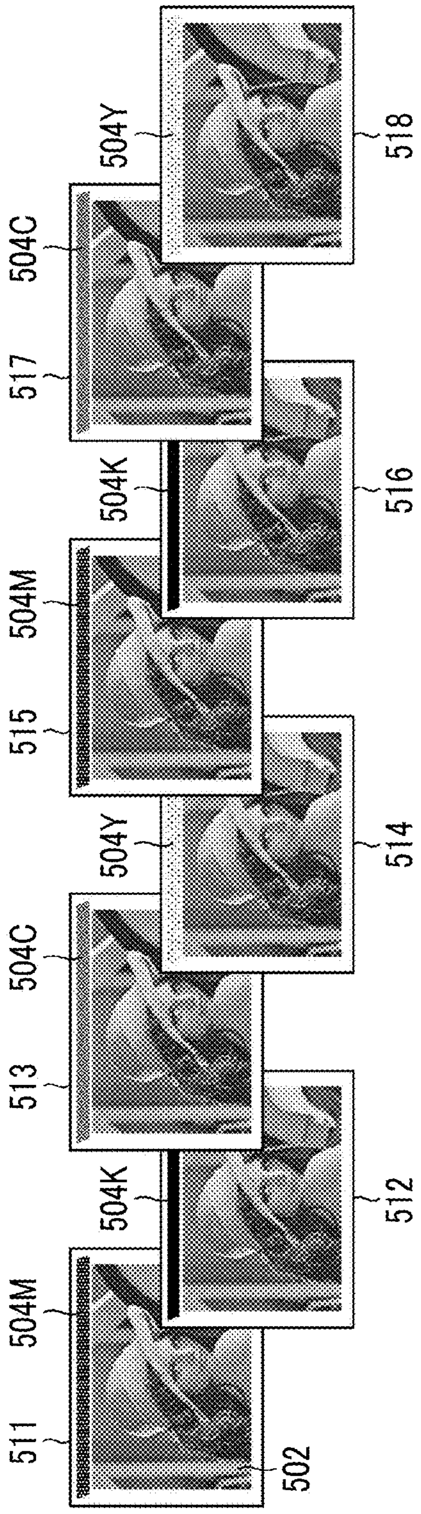
FIG. 8 is a conceptual diagram illustrating an example of a case in which the ladder patterns corresponding to all colors and all nozzles are separately drawn on a plurality of pages.

FIG. 8 is a conceptual diagram illustrating an example of a case in which ladder patterns corresponding to all colors and all nozzles are separately drawn on a plurality of pages. In a case in which a defective nozzle is detected during continuous printing, the area of the ladder pattern drawing region is limited. Therefore, as described with reference to FIG. 4, the structure in which the ladder pattern 504 is added to the end of the user image 502 and the user image 502 and the ladder pattern 504 are drawn on the same sheet P is used. In this case, as illustrated in FIG. 8, the ladder patterns corresponding to all colors and all nozzles are separately drawn on a plurality of pages.

In FIG. 8, eight printed matters 511 to 518 are continuously printed in the numerical order of reference numerals. The magenta ladder pattern 504M is drawn on a first printed matter 511. The black ladder pattern 504K is drawn on a second printed matter 512. The cyan ladder pattern 504C drawn on a third printed matter 513. The yellow ladder pattern 504Y is drawn on a fourth printed matter 514. Similarly, the ladder patterns are repeatedly drawn in the same order as described above. In this way, the ladder patterns of each color are drawn.

In the case in which one ladder pattern is drawn on one page as illustrated in FIG. 8, at least four printing operations are required to draw the ladder patterns corresponding to all of four colors, that is, C, M, Y, and K and all nozzles. The order of the colors illustrated in FIG. 8 is an example and can be appropriately set. In addition, the drawing frequency of the ladder patterns corresponding to each of C, M, Y, and K may be changed. FIG. 8 illustrates an example in which the user image 502 with the same pattern is continuously printed. However, the invention can also be applied to a case in which the user images with different patterns are continuously printed as in variable printing. That is, in the case of variable printing, a plurality of pages of printed images of two or more types are continuously printed during continuous printing.

Figure 9:
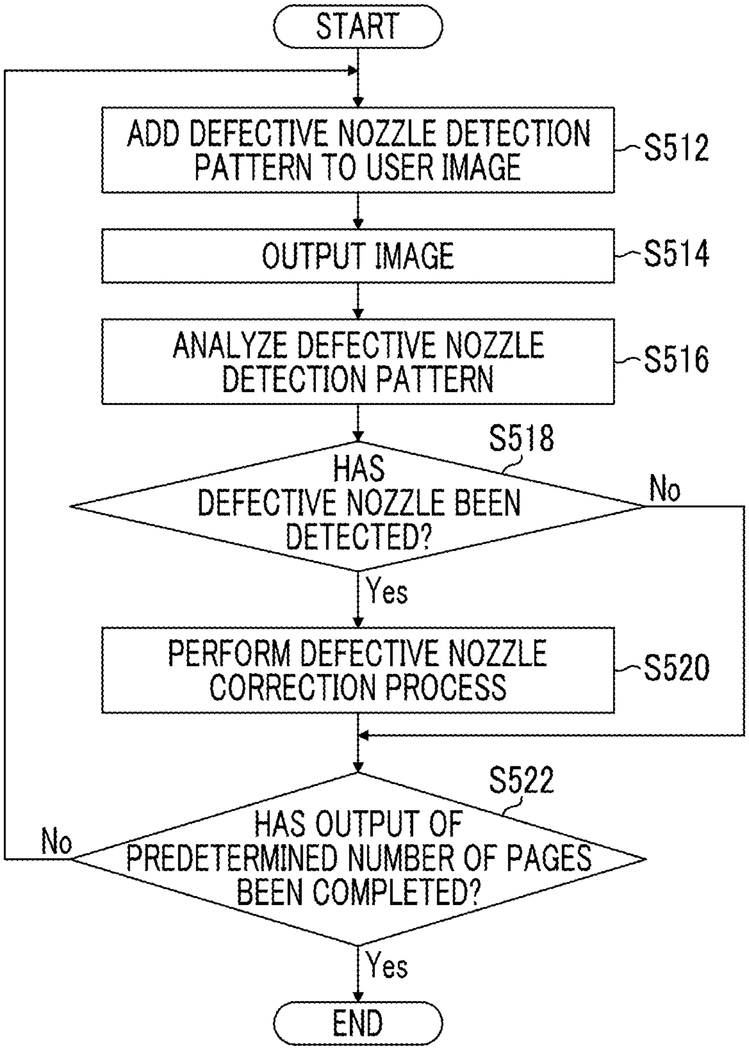
FIG. 9 is a flowchart when a method for specifying a defective nozzle is performed during continuous printing.

FIG. 9 is a flowchart when the method for specifying a defective nozzle during continuous printing is performed. Each step of the flowchart illustrated in FIG. 9 is performed by the ink jet printing apparatus, the control device of the ink jet printing apparatus, or the ink jet printing system which is a combination thereof.

When a printing process starts, the control device performs a process of adding the defective nozzle detection pattern to the user image in Step S512. Data of the user image to be printed is input as a printing document to the control device. Each of the ladder patterns 504M, 504K, 504C, and 504Y illustrated in FIG. 8 is an example of the defective nozzle detection pattern. The control device adds the defective nozzle detection pattern to the end of the user image to generate output image data corresponding to one page.

In Step S514, the control device performs a process of outputting an image on the basis of the generated output image data. The control device controls the operation of the ink jet printing apparatus such that the defective nozzle detection pattern and the user image are drawn on the sheet, on the basis of the output image data. The ink jet printing apparatus draws the defective nozzle detection pattern and the user image under the control of the control device.

In Step S516, the control device performs a process of analyzing the defective nozzle detection pattern. Step S516 in which the defective nozzle detection pattern is analyzed includes a step in which the image reading device reads the defective nozzle detection pattern recorded on the sheet, a step in which the control device acquires data of the read image of the defective nozzle detection pattern obtained from the image reading device, and a step in which the read image of the defective nozzle detection pattern is analyzed to detect a defective nozzle.

In Step S518, the control device determines whether a defective nozzle has been detected by the image analysis process in Step S516.

In a case in which a defective nozzle has been detected by the image analysis process in Step S516, the determination result in Step S518 is "Yes" and the process proceeds to Step S520. In Step S520, the control device performs a defective nozzle correction process. The defective nozzle correction process is a process of correcting image quality for the defective nozzle and is, for example, a correction process using a non-jetting correction technique. After the non-jetting nozzle correction process in Step S520 is performed, the control device proceeds to Step S522.

On the other hand, in a case in which a defective nozzle has not been detected by the image analysis process in Step S516, the determination result in Step S518 is "No". Step S520 is omitted and the control device proceeds to Step S522.

In Step S522, the control device determines whether the output of a predetermined number of pages has been completed. When the output of the number of pages designated by a print job has not been completed, the determination result in Step S522 is "No". In this case, the control device returns to Step S512 and continues to perform continuous printing.

On the other hand, when the output of the number of pages designated by the print job has been completed in Step S522, the determination result in Step S522 is "Yes" and the control device ends the printing process. The flowchart illustrated in FIG. 9 is executed to perform the continuous printing illustrated in FIG. 8.

In order to detect a defective nozzle from the ladder pattern during continuous printing, it is necessary to change the ladder pattern to be output for each page and to output the ladder patterns corresponding to all colors and all nozzles, as illustrated in FIG. 8. In this method, it takes time to specify a defective nozzle as described in [Problem 2].

<<Outline of Streak Detection Technique>>

Figure 10:
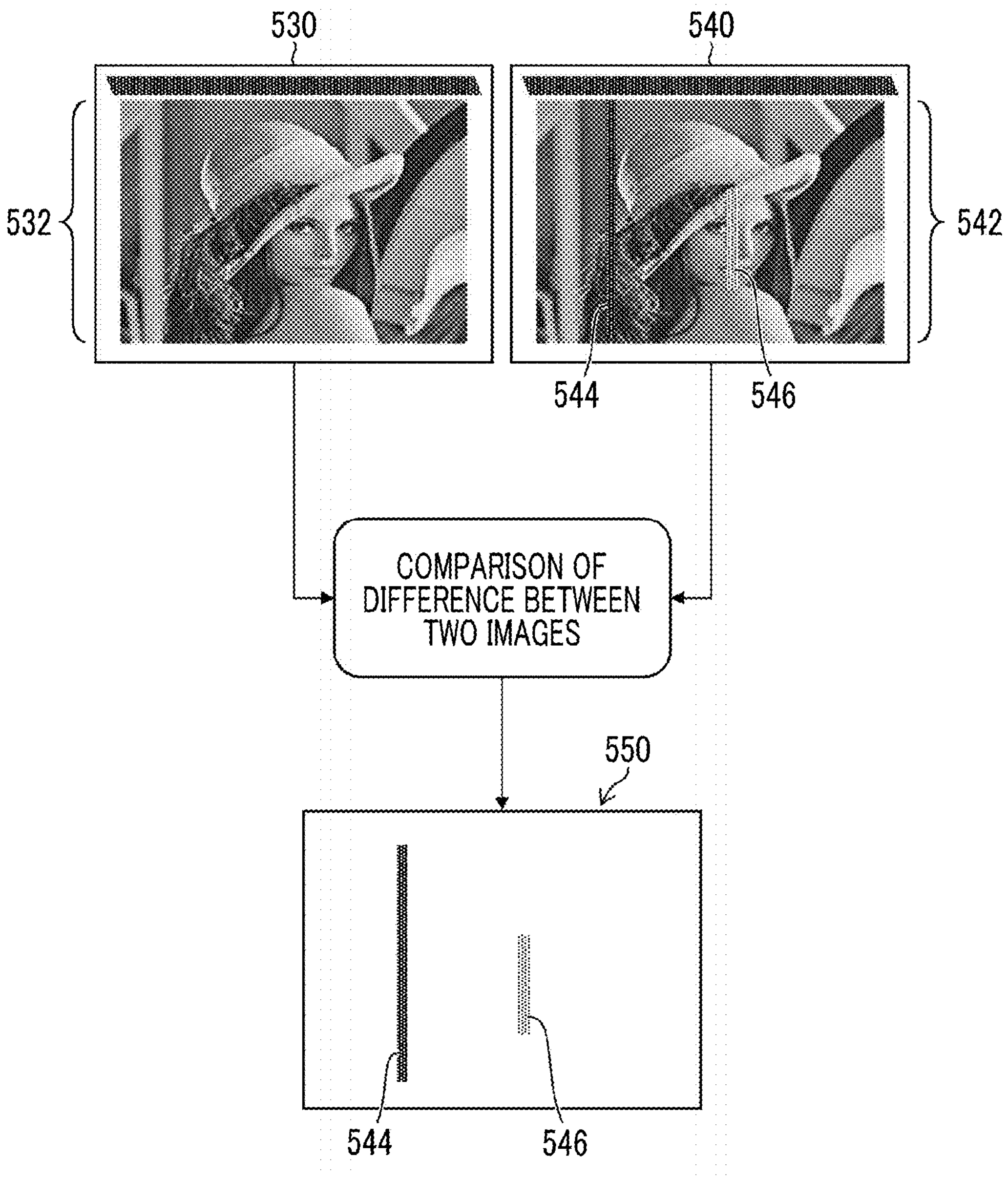
FIG. 10 is a diagram illustrating the basic principle of a streak detection algorithm.

Next, the outline of a streak detection technique will be described. The streak detection technique is a method that determines whether a streak actually occurs in a printed image on the basis of the image data printed by the user. FIG. 10 is a diagram illustrating the basic principle of a streak detection algorithm.

First, a proper image 530 is prepared in advance. The proper image 530 may be any one of an input image which is input as a printing image, an image obtained by performing a predetermined process, such as a filtering process, for the input image, and an image obtained by reading a printed image of a high-quality printed matter in advance, using, for example, a scanner, before continuous printing is performed.

The proper image 530 illustrated in FIG. 10 is an example of the image including the ladder pattern. However, during a streak detection process, information about the ladder pattern is not required. The proper image 530 may include image information of a user image region 532 and the information about the ladder pattern may be omitted.

After the proper image 530 is prepared, the image reading device reads an output image from each proper image every time during continuous printing and acquires a measured image 540. Then, the difference between the proper image 530 and the measured image 540 is compared to determine whether a streak occurs.

For example, two streaks 544 and 546 occur in a user image region 542 of the measured image 540 illustrated in FIG. 10. Streak information 550 corresponding to the streaks 544 and 546 is obtained from the difference between the image information of the user image region 532 of the proper image 530 and the image information of the user image region 542 of the measured image 540. The measured image 540 may include the image information of the user image region 542 and the information about the ladder pattern may be omitted.

Figure 11:
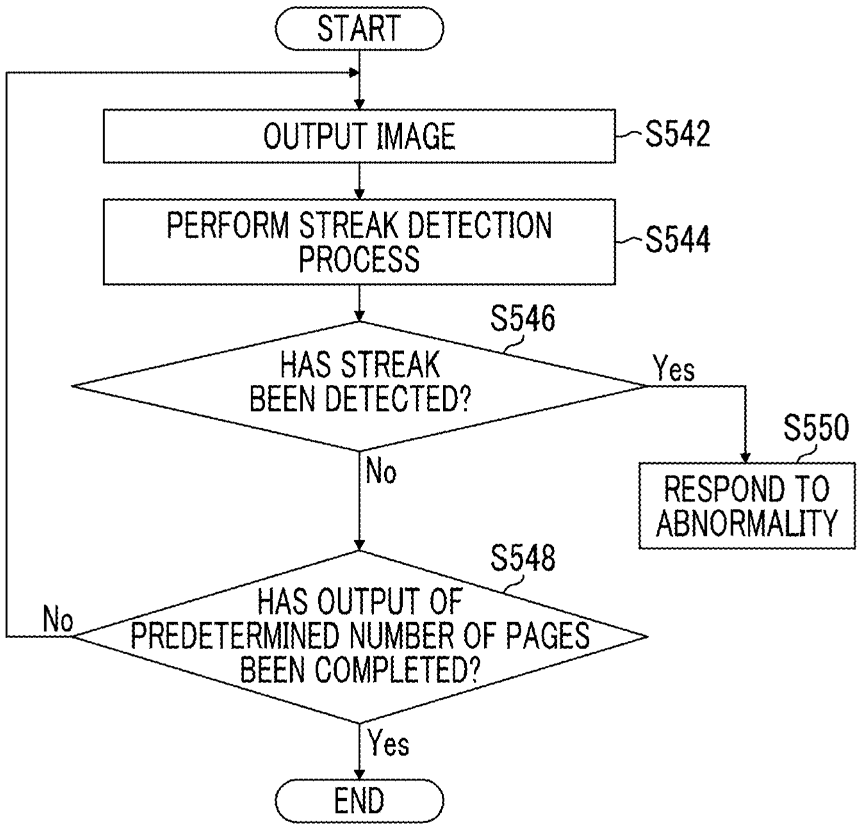
FIG. 11 is a flowchart illustrating a streak detection process performed during continuous printing.

FIG. 11 is a flowchart illustrating the streak detection process performed during continuous printing. When a continuous printing process starts on the basis of a print job, the control device performs a process of outputting an image on the basis of image data to be printed in Step S542. The control device controls the operation of the ink jet printing apparatus on the basis of output image data such that a user image is drawn on a sheet. The ink jet printing apparatus draws the user image under the control of the control device.

In Step S544, the control device performs the streak detection process. An algorithm of the streak detection process is as described with reference to FIG. 10. The streak detection process in Step S544 includes a step in which the image reading device reads the user image drawn on the sheet, a step in which the control device acquires data of a measured image which is the read image of the user image obtained from the image reading device, a step in which the difference between the measured image and a proper image which is prepared in advance is compared to obtain streak information, and a step in which it is determined whether there is a streak on the basis of the streak information. As a method for determining whether there is a streak, for example, the signal intensity of the streak information is compared with a predetermined threshold value and it is determined that a streak defect has occurred in a case in which the signal intensity of the streak information is equal to or greater than the threshold value.

In Step S546, the control device determines whether a streak has been detected. In a case in which a streak has not been detected by the streak detection process in Step S544, the determination result in Step S546 is "No" and the control device proceeds to Step S548.

In Step S548, the control device determines whether the output of a predetermined number of pages has been completed. When the output of the number of pages designated by a print job has not been completed, the determination result in Step S548 is "No". In this case, the control device returns to Step S542 and continues to perform continuous printing.

On the other hand, when a streak has been detected by the streak detection process in Step S544, the determination result in Step S546 is "Yes" and the control device proceeds to Step S550.

In Step S550, the control device responds to abnormality. An example of the response to abnormality is the display of a warning and/or the execution of a maintenance operation, such as head cleaning. An abnormality response process may be a process of temporarily stopping printing or an abnormal end process of ending printing.

When the output of the number of pages designated by the print job has been completed in Step S548, the determination result in Step S548 is "Yes" and the control device ends the printing process.

The streak detection technique described with reference to FIG. 10 and FIG. 11 has the advantage that it is possible to rapidly and accurately determine whether a streak occurs during continuous printing. However, since the streak detection technique does not specify a defective nozzle as described in [Problem 3], it is difficult to accurately perform image quality correction for the defective nozzle.

This disclosure provides a hybrid image inspection technique having both the advantages of the defective nozzle specification technique described in FIG. 8 and FIG. 9 and the advantages of the streak detection technique described with reference to FIG. 10 and FIG. 11.

<<Image Inspection Method According to First Embodiment>>

In an image inspection method according to a first embodiment, a process of specifying a defective nozzle is performed after a streak is detected.

[Outline of Process]

Figure 12:
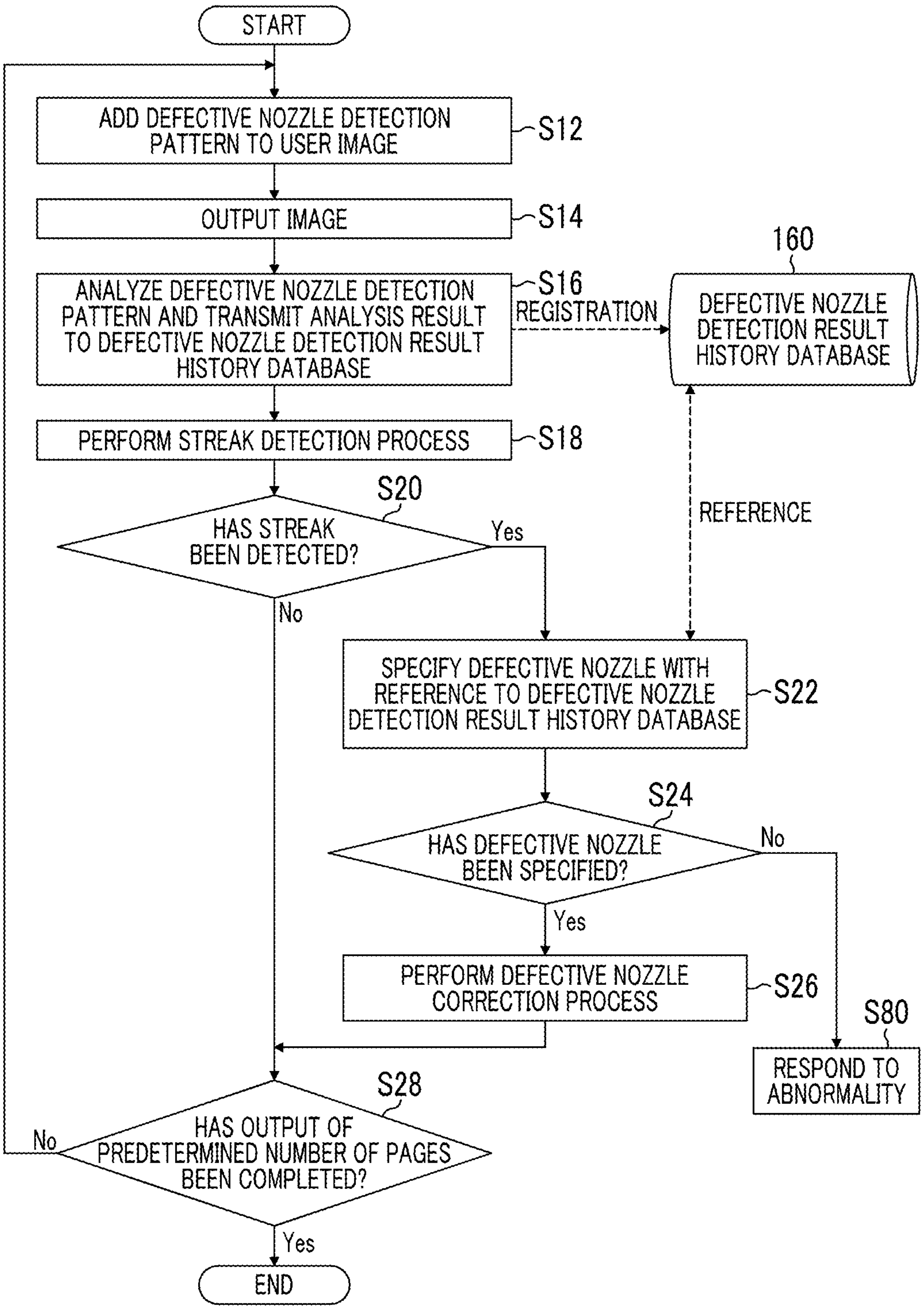
FIG. 12 is a flowchart illustrating the procedure of a process of an image inspection method according to a first embodiment.

FIG. 12 is a flowchart illustrating the procedure of a process in the image inspection method according to the first embodiment. Each step of the flowchart illustrated in FIG. 12 is performed by the control device 100 functioning as an image inspection device, the ink jet printing apparatus 1A, or the ink jet printing system 101 which is a combination thereof.

When a continuous printing process starts according to a print job, first, the image output process based on Steps S512 and S514 illustrated in FIG. 9 is performed. Steps S12 and S14 in FIG. 12 are the same as Steps S512 and S514 in FIG. 9.

In Step S16 in FIG. 12, the control device 100 analyzes the defective nozzle detection pattern output in Step S14 and transmits the analysis result to a defective nozzle detection result history database 160. Step S16 in which the defective nozzle detection pattern is analyzed includes a step in which the image reading device 48 reads the defective nozzle detection pattern drawn on the sheet P, a step in which the control device 100 acquires data of the read image of the defective nozzle detection pattern obtained from the image reading device 48, a step in which the image inspection unit 140 analyzes the read image of the defective nozzle detection pattern to detect a defective nozzle, and a step in which the control device 100 registers data indicating the detection result of the defective nozzle in the defective nozzle detection result history database 160.

That is, first, the control device 100 performs only image analysis for detecting a defective nozzle detection and the storage of data indicating the analysis result for the defective nozzle detection pattern output by the image output process in Step S14. Even when a defective nozzle is detected in Step S16, the control device 100 does not immediately perform an image quality correction process for the defective nozzle. Instead, the control device 100 stores the detection result of the defective nozzle as a history in the defective nozzle detection result history database 160 once. The defective nozzle detection result history database 160 is a database that stores the detection result of the defective nozzle as a history. Data of the detection result of the defective nozzle stored in the defective nozzle detection result history database 160 is referred to as history data.

In Step S16, the step in which the control device 100 acquires the data of the image read from the image reading device 48 corresponds to an example of a read image acquisition step. The read image of the defective nozzle detection pattern obtained from the image reading device 48 corresponds to an example of a first read image. The read image of the user image obtained from the image reading device 48 corresponds to an example of a second read image. In Step S16, the step in which the image inspection unit 140 of the control device 100 analyzes the read image of the defective nozzle detection pattern to detect a defective nozzle corresponds to an example of a defective nozzle detection processing step.

In Step S16, the step in which the control device 100 registers data indicating the detection result of the defective nozzle in the defective nozzle detection result history database 160 corresponds to an example of a history information storage step.

In Step S18 following Step S16, the control device 100 performs a streak detection process for the output user image. The streak detection process in Step S18 is the same as the process in Step S544 in FIG. 10. Step S18 corresponds to an example of an image defect detection processing step.

In Step S20, the control device 100 determines whether a streak has been detected. In a case in which a streak has been detected by the streak detection process in Step S18, the control device 100 proceeds to Step S22.

In Step S22, the control device 100 specifies a defective nozzle with reference to the defective nozzle detection result history database 160. The control device 100 performs a process of extracting data from the defective nozzle detection result history database 160, using the streak information obtained by the streak detection process in Step S18, and specifying a defective nozzle causing the streak. Step S22 corresponds to an example of a defective nozzle specification processing step.

In Step S24, the control device 100 determines whether a defective nozzle has been specified by the defective nozzle specification process in Step S22. In a case in which a defective nozzle has been specified by the defective nozzle specification process in Step S22, the control device 100 proceeds to Step S26.

In Step S26, the control device 100 performs a defective nozzle correction process. The defective nozzle correction process is an image quality correction process for the defective nozzle and is the same as the process in Step S520 in FIG. 9. After Step S26 in FIG. 12, the control device 100 proceeds to Step S28.

In a case in which a streak has not been detected by the streak detection process in Step S18 and the determination result in Step S20 is "No", the control device 100 proceeds to Step S28. Step S28 is the same as Step S522 in FIG. 9.

A printed matter from which a streak has been detected is a failed printed matter with poor image quality. Therefore, preferably, the printed matter is not counted as a predetermined number of printed pages and is processed as a waste sheet. In this case, after the defective nozzle correction process in Step S26, it is preferable to perform an "additional printing" process of printing the same user image as the failed printed matter again.

It is preferable to a discrimination process of easily discriminating the failed printed matter from which a streak has been detected from a high-quality printed matter. For example, as the discrimination process, the following processes are performed: a process of changing the discharge destination of the failed printed matter; and a stamping process of putting a mark indicating the failed printed matter.

On the other hand, in a case in which a defective nozzle has not been specified by the defective nozzle specification process in Step S22 in FIG. 12, the control device 100 proceeds to Step S80 and responds to abnormality. Step S80 is the same as Step S550 in FIG. 10.

[Method for Specifying Defective Nozzle with Reference to Defective Nozzle Detection Result History Database]

Here, a detailed example of the process of specifying a defective nozzle on the basis of the detection result of a streak and the defective nozzle detection result history database 160 will be described.

FIG. 13 is a conceptual diagram illustrating an example the defective nozzle detection result history database 160. The defective nozzle detection result history database 160 illustrated in FIG. 13 has a format in which a page number for identifying an output page is associated with a detection color which is an ink color of the defective nozzle detection pattern output when each page is printed and defective nozzle information generated when each page is output is stored. The defective nozzle information is information capable of specifying the nozzle number of the defective nozzle detected by image analysis for the defective nozzle detection pattern.

For example, for an output page with page number "Page 1", a magenta defective nozzle detection pattern is output and the detection result of the defective nozzle shows that a nozzle with nozzle number m−1 in a magenta ink jet head is detected as the defective nozzle.

For an output page with page number "Page 2", a black defective nozzle detection pattern is output and the detection result of the defective nozzle shows that two nozzles, that is, a nozzle with nozzle number 0 and a nozzle with nozzle number m−3 in a black ink jet head are detected as the defective nozzles.

As illustrated in FIG. 13, with the output of each page by continuous printing, data of the detection result of the defective nozzle for each output page is accumulated as a history in the defective nozzle detection result history database 160. The page number indicates the order in which the page is output. That is, the page number corresponds to time information. Time information, such as a time stamp, may be used as the time information indicating the time when each page is output, instead of the page number or while being combined with the page number.

FIG. 13 illustrates an example of a data structure with a table format in which a plurality of history data items from "Page 1" to the latest page "Page Latest" are arranged in time series for ease of understanding. In this example, the ink jet printing system 101 detects the defective nozzles of each color while changing four colors, that is, magenta, black, cyan, and yellow in turn in this order whenever the page for each color is changed.

It is preferable that the defective nozzle detection result history database 160 stores at least the latest history data of each of the four colors. It is more preferable that the defective nozzle detection result history database 160 stores a plurality of history data items including at least the latest history data of each color. The information registered in the defective nozzle detection result history database 160 corresponds to an example of history information.

FIG. 14 is a diagram schematically illustrating an example of a method for specifying a defective nozzle using the defective nozzle detection result history database 160 in a case in which a streak has been detected by the streak detection process.

Figure 15:
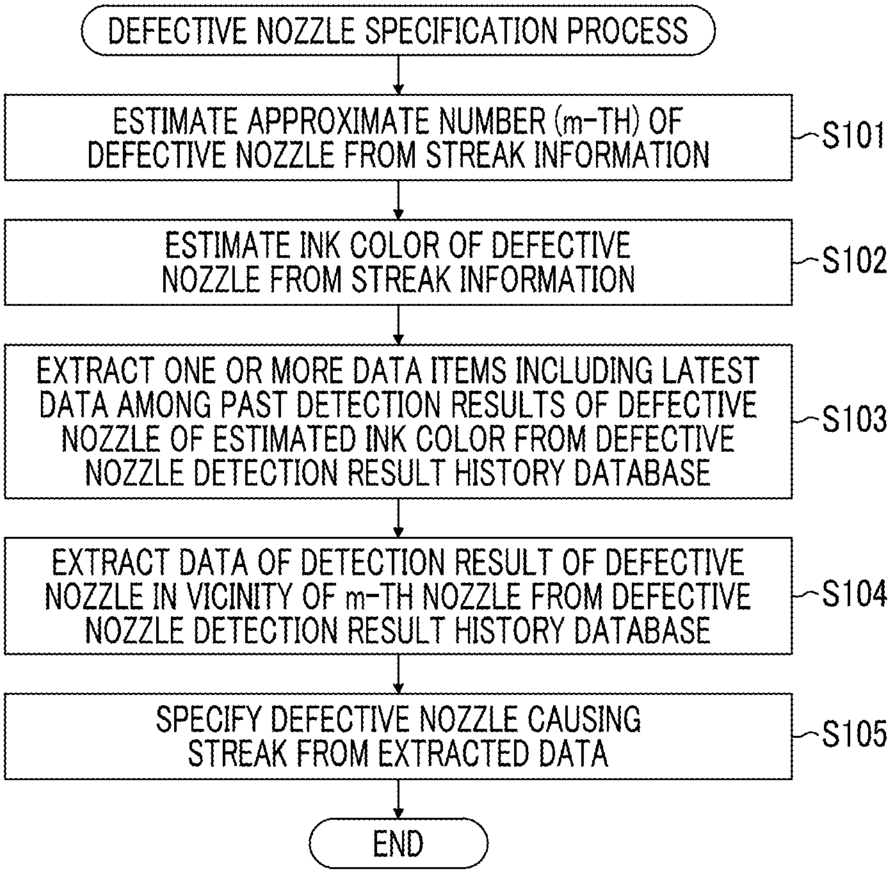
FIG. 15 is a flowchart illustrating the procedure of a defective nozzle specification process of specifying the defective nozzle using the defective nozzle detection result history database.

FIG. 15 is a flowchart illustrating the procedure of a defective nozzle specification process for specifying a defective nozzle using the defective nozzle detection result history database 160. The flowchart of FIG. 15 illustrates the content of the process in Step S22 in FIG. 12.

When a streak is detected by the streak detection process (Step S18 in FIG. 12), the defective nozzle specification process is performed according to the flowchart illustrated in FIG. 15.

First, when the defective nozzle specification process starts, in Step S101, the control device estimates the approximate number of the defective nozzle from the streak information obtained by the streak detection process. The streak information is data of a difference image indicating the difference between the proper image 530 and the measured image 540 as described in FIG. 10. The streak information corresponds to an example of information about an image defect. The approximate number of the defective nozzle is the number of a nozzle that is approximately estimated as the defective nozzle from the relationship between the position of the streak indicated by the streak information and the position of each nozzle of the ink jet head. The approximate number of the defective nozzle is referred to as an "approximate defective nozzle number". The control device 100 performs coordinate analysis on the basis of the streak information to estimate the approximate defective nozzle number. In this example, it is assumed that the approximate defective nozzle number is, for example, m.

The recording resolution of the single pass ink jet head is defined by the nozzle density of the ink jet head. The nozzle density of the ink jet head is, for example, 1200 npi. The term "npi" means nozzles per inch and is a unit indicating the number of nozzles per inch. A pixel dot can be recorded by one nozzle. Therefore, npi indicating the nozzle density can be substituted with dpi indicating a recording resolution.

The position of the streak indicated by the streak information is specified in units of pixels defined by the reading resolution of the image reading device. The reading resolution of the image reading device may be lower than the recording resolution of the ink jet head. For example, an image reading device with a reading resolution of about 400 dpi to 600 dpi can be used.

For example, the position of the streak obtained from the streak information can be specified by an accuracy of about ±1 pixel in units of pixels defined by the reading resolution of the image reading device. That is, it is difficult to accurately specify the nozzle number of the defective nozzle from the streak information obtained by analyzing the measured image 540 which is the read image with a resolution lower than the nozzle density of the ink jet head.

In Step S101, the approximate defective nozzle number of the nozzle estimated as the defective nozzle is calculated from the streak information in the allowable range of an error of about ±1 pixel in units of pixels in the measured image 540.

In Step S102, the control device 100 estimates the ink color of the defective nozzle from the streak information. The control device 100 determines the color of the streak on the basis of the streak information which is the difference data between the proper image 530 and the measured image 540 to estimate the ink color caused by the defective nozzle. The control device 100 analyzes the color of the image of the streak information and determines the color of the streak on the basis of the analysis result. The control device 100 estimates the ink color caused by the defective nozzle from the color of the streak.

In Step S103, the control device 100 extracts one or more data items including the latest data among the past defective nozzle detection results with the ink color estimated in Step S102 from the defective nozzle detection result history database 160. For example, the control device 100 extracts two data items which are two latest past data items including the latest data among the past defective nozzle detection results with the ink color estimated in Step S102 from the defective nozzle detection result history database 160.

In the example illustrated in FIG. 14, aspects in which the ink color estimated in Step S102 is black and two data items, that is, data "Page Latest", which is the latest history data, and data "Page Latest-4" are extracted as two latest past data items including the latest data for black are displayed so as to be highlighted by thick frames 162A and 162B.

Then, in Step S104, the control device 100 extracts data of the defective nozzle detection results of the nozzles in the vicinity of the m-th nozzle calculated in Step S101 extracts from the defective nozzle detection result history database 160. The range of the "vicinity" of the m-th nozzle can be determined to be, for example, a total of five nozzles which is the range of an (m−2)-th nozzles to an (m+2)-th nozzles. In a case in which the range of m±2 nozzle numbers is determined to be the "vicinity of the m-th nozzle", specifically, five nozzles, that is, nozzles with nozzle number m−2, nozzle number m−1, nozzle number m, nozzle number m+1, and nozzle number m+2 correspond to the "vicinity of the m-th nozzle". The range of the vicinity is set to an appropriate range on the basis of the relationship between the reading resolution of the image reading device and the nozzle density of the ink jet head. In FIG. 14, an aspect in which the history data of the range of m±2 nozzle numbers is extracted is displayed so as to be highlighted by a thick frame 164.

Then, in Step S105, the control device 100 specifies a defective nozzle causing the streak from the data extracted in Step S103 and Step S104. In the example illustrated in FIG. 14, a nozzle with nozzle number m−1 is specified as the defective nozzle causing the streak from data which is extracted as a product set of data extraction conditions in Step S103 and data extraction conditions in Step S104.

The order of the processes in Step S101 to Step S104 is not limited to the example illustrated in FIG. 15 and can be changed in a reasonable range. For example, the order of the processes in Step S101 and Step S102 can be reversed. In addition, the order of the processes in Step S103 and Step S104 can be reversed. Alternatively, the process may be performed in the order of Step S101, Step S104, Step S102, Step S103, and Step S105.

According to the image inspection method of the first embodiment, it is possible to compensate each problem described in [Problem 1] and [Problem 2] with the advantages of the streak detection technique and the defective nozzle specification technique and to effectively perform the specification of a defective nozzle and the image quality correction process.

Configuration of Image Inspection Device According to First Embodiment

Figure 16:
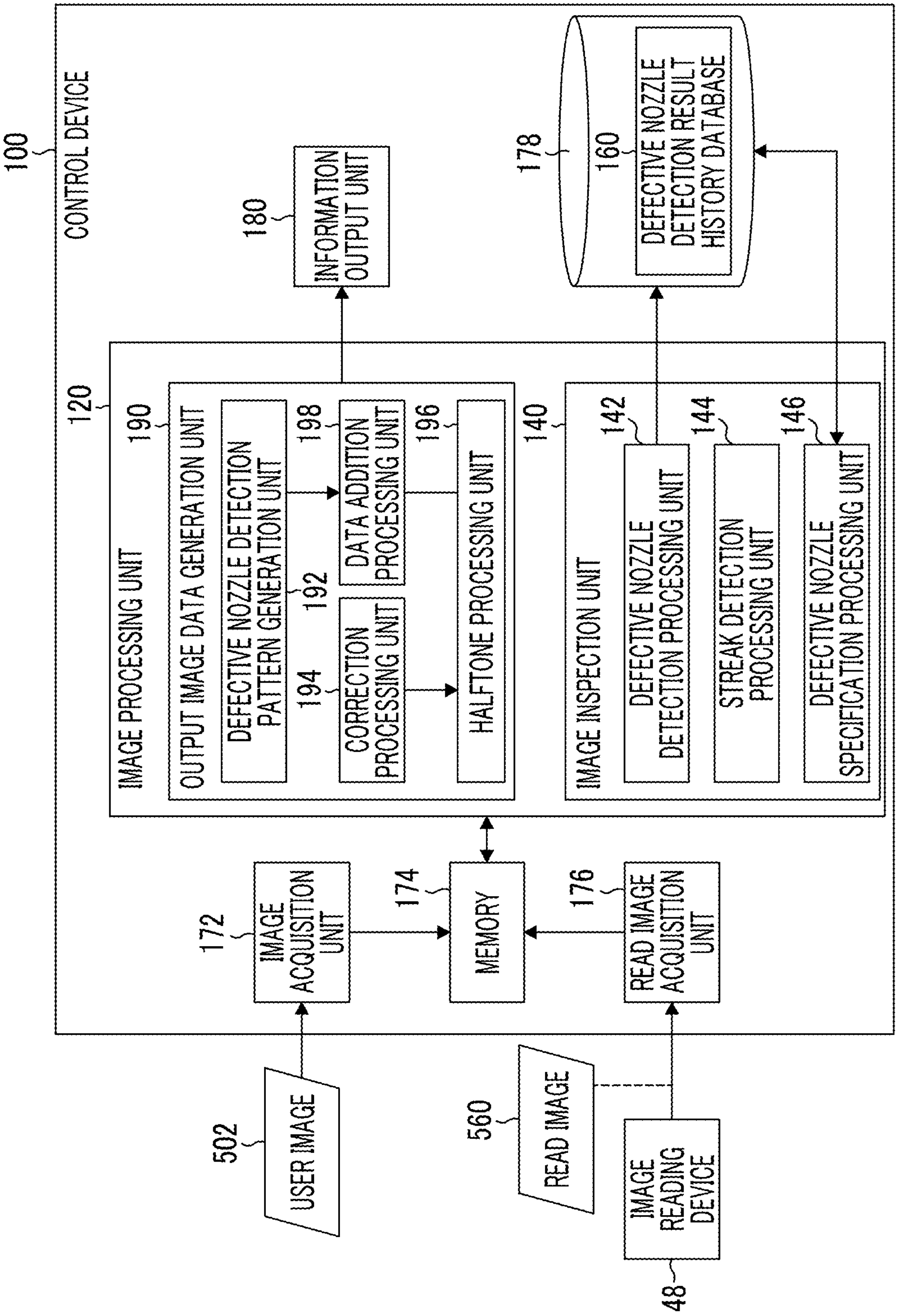
FIG. 16 is a block diagram illustrating the main configuration of an image inspection function and an output image generation function of a control device.

FIG. 16 is a block diagram illustrating the main configuration of the control device 100 related to an image inspection function and an output image generation function. The control device 100 can perform the process of the image inspection method according to the first embodiment.

The control device 100 includes an image acquisition unit 172, a memory 174, a read image acquisition unit 176, a database storage unit 178, and an information output unit 180 in addition to the image processing unit 120. The image acquisition unit 172 is an interface that acquires data of the user image 502 to be printed from other circuits outside or inside the device. The image acquisition unit 172 can be configured by a data input terminal. The image acquisition unit 172 may be a wired or wireless communication interface unit, a media interface unit that reads data from an external storage device, such as a memory card, or an appropriate combination thereof. The communication unit 112 described in FIG. 2 or a media interface unit (not illustrated) can function as the image acquisition unit 172.

The read image acquisition unit 176 is an interface that acquires data of a read image 560 obtained from the image reading device 48. The read image acquisition unit 176 may receive the data of the read image 560 from the image reading device 48 or may acquire the data of the read image 560 from other circuits in the control device 100. The read image 560 may be image data in which the read image data of the defective nozzle detection pattern and the read image data of the user image are included in one read image, the read image data of the defective nozzle detection pattern obtained by reading a defective nozzle detection pattern region, or the read image data of the user image obtained by reading a user image region. The defective nozzle detection pattern region is a region in which a pattern for inspecting a jetting state of a nozzle is drawn and is referred to as a "nozzle inspection region" in some cases. The defective nozzle detection pattern region corresponds to an example of a first region. The user image region corresponds to an example of a second region.

The memory 174 is a storage unit that stores the data of the user image 502 acquired through the image acquisition unit 172. In addition, the memory 174 is a storage unit that stores the read image 560 acquired through the read image acquisition unit 176. The memory 174 can function as a work memory when the image processing unit 120 performs various arithmetic operations. A region of the RAM 134 described in FIG. 2 may be used as the memory 174.

The database storage unit 178 is a storage unit that stores the defective nozzle detection result history database 160. A storage area of the information storage unit 118 illustrated in FIG. 2 may be used as the database storage unit 178. The database storage unit 178 corresponds to an example of a history information storage unit.

The information output unit 180 is an output interface for outputting the information generated in the image processing unit 120. The information output unit 180 may output information to, for example, other processing units in the control device 100 or may output information to the outside of the control device 100.

The image processing unit 120 includes an output image data generation unit 190 and the image inspection unit 140. The output image data generation unit 190 includes a defective nozzle detection pattern generation unit 192, a correction processing unit 194, a halftone processing unit 196, and a data addition processing unit 198. In addition, the output image data generation unit 190 includes a decomposition processing unit (not illustrated) that decomposes an input image into image data items corresponding to C, M, Y, and K ink colors.

The defective nozzle detection pattern generation unit 192 generates the original data of the defective nozzle detection pattern drawn at the leading end of the user image 502.

The correction processing unit 194 performs various image correction processes for the image data to be printed. The image correction processes performed by the correction processing unit 194 include a defective nozzle correction process that makes a streak invisible on the basis of the inspection result of the image inspection unit 140. The defective nozzle correction process corresponds to an example of an image quality correction process for preventing an image defect. The defective nozzle correction process corresponds to an example of a first image quality correction process.

The halftone processing unit 196 performs a process that quantizes the image signal of each ink color corrected by the correction processing unit 194 using a processing method, such as a dither method or an error diffusion method, to convert the image signal into binary or multi-valued dot data. In this example, the halftone processing unit 196 generates C, M, Y, and K dot data.

The data addition processing unit 198 performs a process that adds the original data of the defective nozzle detection pattern generated by the defective nozzle detection pattern generation unit 192 to the data of the user image 502 to be printed to generate output data corresponds to one page. The data of the defective nozzle detection pattern may be added to the data of the user image before halftone processing or may be added to the data after halftone processing.

The output image data generated by the output image data generation unit 190 is transmitted to the image recording control unit 124 (see FIG. 2) through the information output unit 180.

The image inspection unit 140 includes a defective nozzle detection processing unit 142, a streak detection processing unit 144, and a defective nozzle specification processing unit 146. The defective nozzle detection processing unit 142 analyzes the data of the read image of the defective nozzle detection pattern to detect a defective nozzle. The defective nozzle detection processing unit 142 performs a process that registers the information of the defective nozzle detection result in the defective nozzle detection result history database 160. The defective nozzle detection processing unit 142 performs the process in Step S16 in FIG. 12.

The streak detection processing unit 144 analyzes the data of the read image obtained by reading the user image printed on the sheet P to detect a streak. The streak detection processing unit 144 compares the proper image 530 and the measured image 540 to generate the streak information 550 and determines whether there is a streak. The streak detection processing unit 144 performs the process in Step S18 in FIG. 12. The streak detection processing unit 144 corresponds to an example of an image defect detection processing unit.

The defective nozzle specification processing unit 146 specifies a defective nozzle from the streak information 550 detected by the streak detection processing unit 144 with reference to the defective nozzle detection result history database 160. The defective nozzle specification processing unit 146 performs the process in Step S22 in FIG. 12. Information of the defective nozzle specified by the defective nozzle specification processing unit 146 is transmitted to the correction processing unit 194. The correction processing unit 194 performs a defective nozzle correction process which is an image quality correction process for the specified defective nozzle.

Figure 17:
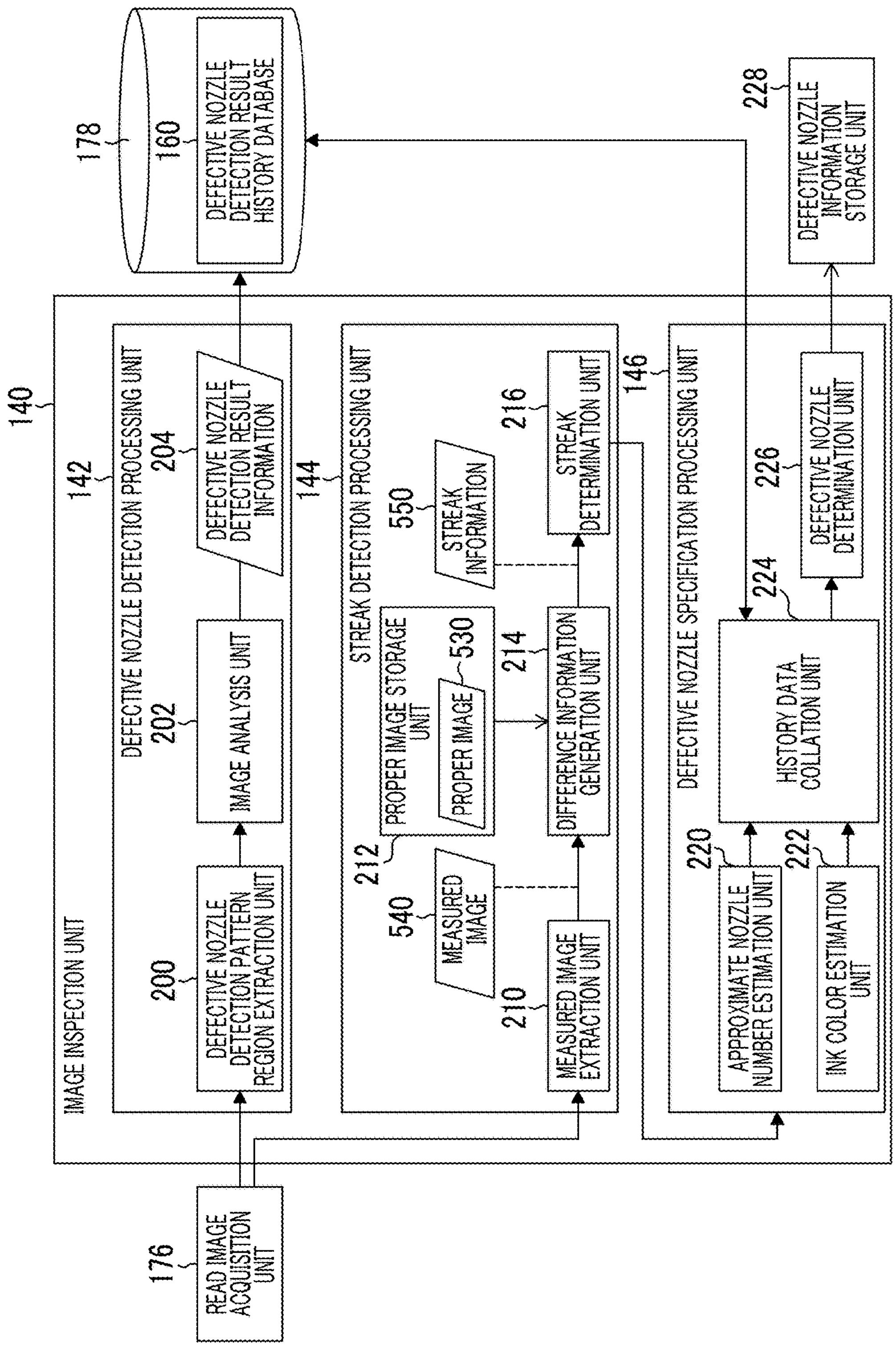
FIG. 17 is a block diagram providing the function of an image inspection unit.

FIG. 17 is a block diagram providing a detailed processing function of the image inspection unit 140. The defective nozzle detection processing unit 142 includes a defective nozzle detection pattern region extraction unit 200 and an image analysis unit 202.

The defective nozzle detection pattern region extraction unit 200 performs a process that extracts data of an image region portion of the defective nozzle detection pattern from the read image acquired through the read image acquisition unit 176. Data of the first read image which is the read image of the defective nozzle detection pattern is generated by the defective nozzle detection pattern region extraction unit 200.

The image analysis unit 202 analyzes the data of the read image of the defective nozzle detection pattern to detect a defective nozzle. The image analysis unit 202 determines the jetting state of each nozzle from the recording state of each line of the defective nozzle detection pattern and detects the nozzle number of the defective nozzle. The recording state of each line indicates at least one of whether the line is recorded, the recording position of the line, the width of the line, or an interval between the lines, or a combination thereof.

Defective nozzle detection result information 204 obtained by the process of the image analysis unit 202 is stored in the defective nozzle detection result history database 160.

The streak detection processing unit 144 includes a measured image extraction unit 210, a proper image storage unit 212, a difference information generation unit 214, and a streak determination unit 216.

The measured image extraction unit 210 performs a process that extracts data of an image region portion of the user image from the read image acquired through the read image acquisition unit 176. The data of the measured image 540 which is the read image of the user image is generated by the measured image extraction unit 210. The data of the measured image 540 corresponds to an example of the second read image.

The data of the proper image 530 is stored in the proper image storage unit 212. The storage area of the information storage unit 118 or the RAM 134 described in FIG. 2 may be used as the proper image storage unit 212.

The difference information generation unit 214 calculates the difference between the proper image 530 and the measured image 540 and generates difference information. The difference information includes the information of a streak included in the measured image 540. The streak information 550 is obtained by the process of the difference information generation unit 214.

The streak determination unit 216 determines whether to treat the streak as an image defect which has an effect on visibility on the basis of the signal intensity of the streak indicated by the streak information 550. For example, the streak determination unit 216 compares the signal intensity of the streak with a threshold value and determines that there is a streak in a case in which signal intensity greater than the threshold value is detected.

The defective nozzle specification processing unit 146 includes an approximate nozzle number estimation unit 220, an ink color estimation unit 222, a history data collation unit 224, and a defective nozzle determination unit 226. The approximate nozzle number estimation unit 220 performs coordinate analysis which calculates the coordinates of the position of the streak in the image, using information indicating the streak detection result obtained by the streak detection processing unit 144 and the streak information 550, to estimate the approximate number of the defective nozzle.

The ink color estimation unit 222 estimates the ink color of the defective nozzle from the color of a streak portion in the streak information 550. One or both of the approximate nozzle number estimation unit 220 and the ink color estimation unit 222 may be included in the streak detection processing unit 144.

The history data collation unit 224 extracts history data corresponding to the range of conditions on the basis of approximate nozzle number estimation information and ink color estimation information with reference to the defective nozzle detection result history database 160.

The defective nozzle determination unit 226 specifies the nozzle number of the defective nozzle from the history data extracted by the history data collation unit 224. An example of the process of the history data collation unit 224 and the defective nozzle determination unit 226 is as described in FIG. 14.

Defective nozzle information indicating the nozzle number of the defective nozzle specified by the defective nozzle specification processing unit 146 is stored in a defective nozzle information storage unit 228. The storage area of the information storage unit 118 or the RAM 134 described in FIG. 2 may be used as the defective nozzle information storage unit 228. The correction processing unit 194 illustrated in FIG. 16 performs the defective nozzle correction process on the basis of the defective nozzle information stored in the defective nozzle information storage unit 228.

Effect of First Embodiment

According to the first embodiment, in a case in which the occurrence of a streak on a printed image is actually detected, the process of specifying a defective nozzle is performed and the image quality correction process is performed for the specified defective nozzle. Therefore, an unnecessary process, such as a process of specifying a defective nozzle or a process of excessively correcting image quality, in the situation in which no streaks occur as described in [Problem 1] is not performed and it is possible to effectively perform an accurate defective nozzle specification process and an accurate image quality correction process.

In addition, according to the first embodiment, in a case in which a streak is detected from a printed image, it is possible to early specify a defective nozzle and to early perform the image quality correction process. Therefore, it is possible to prevent the generation of a waste sheet.

<<Image Inspection Method According to Second Embodiment>>

In the first embodiment, there is a case in which it is difficult to specify a defective nozzle. When the specification of a defective nozzle by the process in the first embodiment fails, it is further preferable to perform a process which interrupts an output during continuous printing, outputs a defective nozzle specification chart, and performs image analysis for the output result of the defective nozzle specification chart to specify a defective nozzle. Hereinafter, an example of an embodiment in which the chart output process using an interrupt is performed will be described as a second embodiment.

Figure 18:
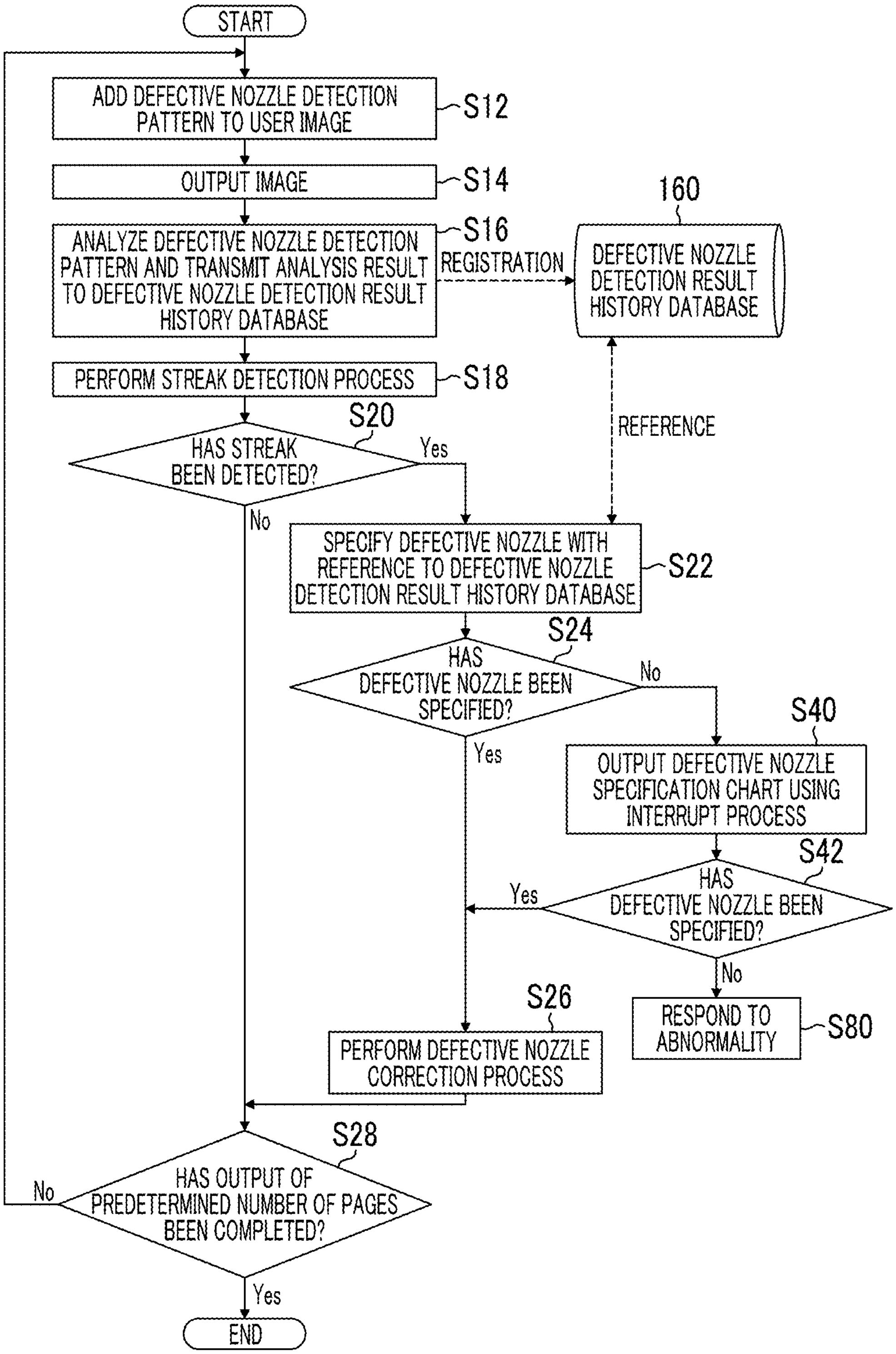
FIG. 18 is a flowchart illustrating the procedure of a process of an image inspection method according to a second embodiment.

FIG. 18 is a flowchart illustrating the procedure of the process of an image inspection method according to the second embodiment. In FIG. 18, the same or similar steps as those in the flowchart illustrated in FIG. 12 are denoted by the same step numbers and the description thereof will not be repeated.

In the flowchart illustrated in FIG. 18, Step S40 and Step S42 which are performed in a case in which the determination result in Step S24 is "No" are added.

In a case in which it is determined in Step S24 that a defective nozzle is not specified and the determination result is "No", the control device 100 proceeds to Step S40. In Step S40, the control device 100 performs a process of outputting the defective nozzle specification chart, using an interrupt. For example, the ladder pattern image corresponding to all colors and all nozzles described in FIG. 6 and FIG. 7 is used as the defective nozzle specification chart output in the interrupt process in Step S40. The defective nozzle specification chart output in Step S40 corresponds to an example of a test chart output by the interrupt process.

In a case in which the defective nozzle specification chart is output by the interrupt process in Step S40, while a predetermined number of pages designated by a print job are continuously printed, an interrupt is performed during continuous printing and the defective nozzle specification chart is drawn without changing a printing speed during continuous printing.

Step S40 includes a step in which the defective nozzle specification chart is output, a step in which the image reading device 48 reads the defective nozzle specification chart drawn on the sheet P, a step in which the control device 100 acquires data of the read image of the defective nozzle specification chart obtained from the image reading device 48, and a step in which image analysis is performed for the read image of the defective nozzle specification chart to specify a defective nozzle. The read image of the defective nozzle specification chart output in Step S40 corresponds to an example of a third read image.

After Step S40, in Step S42, the control device 100 determines whether a defective nozzle has been specified. In a case in which it is determined in Step S40 that a defective nozzle has been specified, the control device 100 proceeds to Step S26 and the defective nozzle correction process. The configuration in which the defective nozzle correction process is performed in Step S26 using the information of the defective nozzle specified in Step S40 corresponds to an example of the configuration in which, after the test chart is output by the interrupt process, the analysis result of the data of the third read image is reflected in a process of printing a printed image during continuous printing.

On the other hand, in a case in which it is determined in Step S40 that a defective nozzle has not been specified, the control device 100 responds to abnormality in Step S80.

According to the second embodiment in which the process illustrated in the flowchart of FIG. 18 is performed, it is possible to compensate each problem described in [Problem 1] to [Problem 3] with the advantages of the streak detection technique and the defective nozzle specification technique and to effectively perform the specification of a defective nozzle and the image quality correction process with high accuracy.

Configuration of Output Image Data Generation Unit in Second Embodiment

Figure 19:
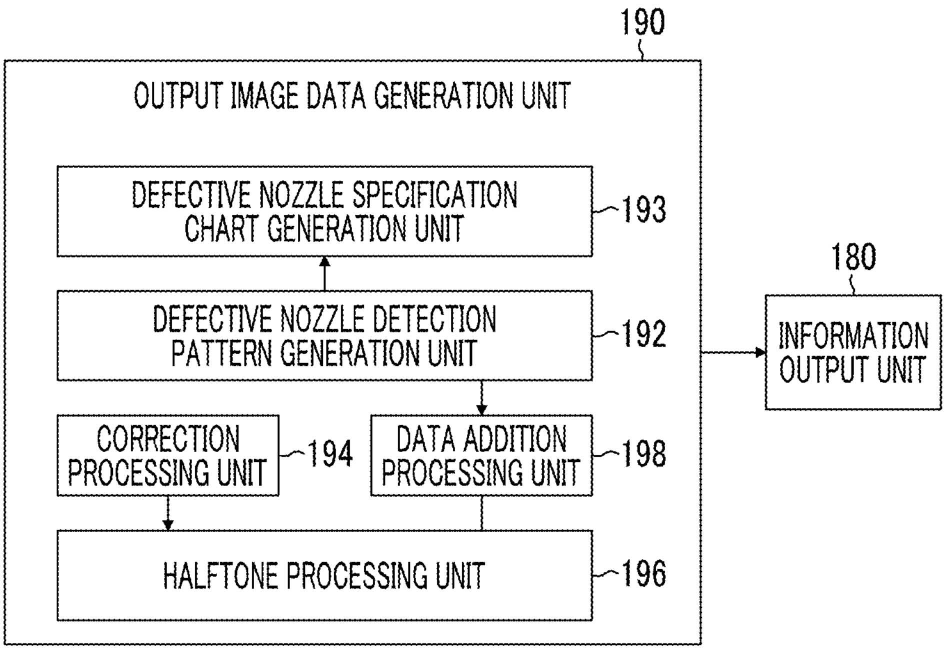
FIG. 19 is a block diagram providing the function of an output image data generation unit in the second embodiment.

FIG. 19 is a block diagram providing the function of an output image data generation unit 190 in the second embodiment. The output image data generation unit 190 includes a defective nozzle specification chart generation unit 193 that generates data for outputting the defective nozzle specification chart. For example, the defective nozzle specification chart generation unit 193 merges data of the defective nozzle detection pattern for each color generated by a defective nozzle detection pattern generation unit 192 to generate the data of the defective nozzle specification chart illustrated in FIG. 6 and FIG. 7. The processing function of the defective nozzle specification chart generation unit 193 can be implemented by the execution of a program by the CPU 130 of the control device 100.

<<Example of Defective Nozzle Specification Chart Using Overlay Method>>

In the second embodiment, the example in which the ladder pattern image described in FIGS. 6 and 7 is output as the defective nozzle specification chart output by the interrupt process (Step S40) has been described. However, since the amount of ink jetted to draw the ladder pattern image described in FIG. 6 and FIG. 7 is less than the amount of ink which is actually used to draw the user image output before and after the interrupt process, the load applied to the ink jet head is less than the actual load. As a result, it may be difficult to appropriately extract a defective nozzle.

Figure 20:
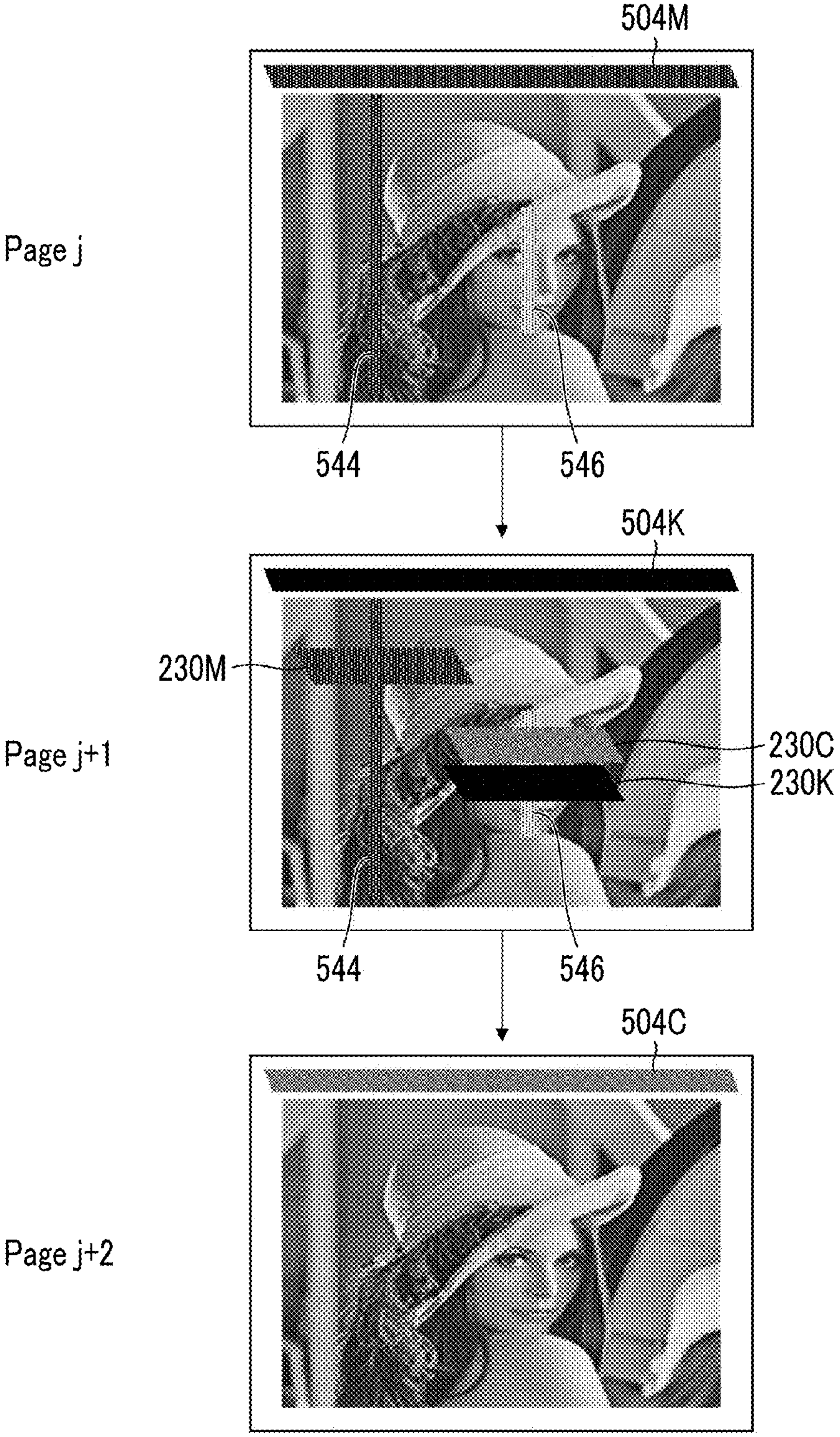
FIG. 20 is a diagram illustrating the outline of the interrupt output of a defective nozzle specification chart using an overlay method.

For this reason, as illustrated in FIG. 20, a method which overlays the defective nozzle specification chart on the user image which is a continuous printing target and is being printed is used to reduce the above-mentioned problem. The main viewpoint of the main defective nozzle specification chart using the overlay method is as follows.

[1] A defective nozzle specification chart is generated according to a streak detection position detected by the streak detection process and the generated defective nozzle specification chart is overlaid on the user image which is a printing target image. The streak detection position means a vertical-direction position and a horizontal-direction position on the image from which a streak has been detected. The defective nozzle specification chart is superimposed on the streak detection position of the user image and is then output.

[2] A defective nozzle specification chart of a corresponding ink color is generated according to the color detected by the streak detection process and the generated defective nozzle specification chart is overlaid on the user image which is a printing target image.

[3] A defective nozzle specification chart is generated according to the range of candidate nozzles including the candidates of a defective nozzle causing a streak and the generated defective nozzle specification chart is overlaid on the user image which is a printing target image.

Next, the main viewpoint will be described in detail with reference to FIG. 20. FIG. 20 is a diagram illustrating the outline of the interrupt output of the defective nozzle specification chart using the overlay method. In FIG. 20, the page number of an output page is indicated by a integer j and three consecutive output pages with page numbers "Page j", "Page j+1", and "Page j+2" are schematically illustrated. FIG. 20 illustrates an example in which two streaks 544 and 546 are detected in a printed image with page number "Page j" during continuous printing.

In this case, when the page with page number "Page j+1" is output by the interrupt process, test charts 230M, 230C, and 230K for specifying a defective nozzle are generated according to the streak detection positions where the streaks 544 and 546 are detected and the generated test charts 230M, 230C, and 230K are overlaid on the streak detection positions of a user image with page number "Page j+1" which is the next printing target image and then output. The user image with page number "Page j+1" corresponds to an example of a printed image which is scheduled to be output during continuous printing.

Each of the test charts 230M, 230C, and 230K for specifying a defective nozzle is a ladder pattern of an ink color corresponding to the color detected by the streak detection process. For example, it is assumed that the ink color of the defective nozzle is estimated to be magenta by color determination for the streak 544. In this case, the test chart 230M for specifying a magenta defective nozzle is generated and the magenta test chart 230M is overlaid on the streak detection position of the streak 544.

It is assumed that the ink color of the defective nozzle is estimated to be cyan or black by color determination for the streak 546. In this case, both the cyan test chart 230C and the black test chart 230K are generated and both the cyan test chart 230C and the black test chart 230K are overlaid on the streak detection position of the streak 546.

Each of the test charts 230M, 230C, and 230K for specifying a defective nozzle is a partial ladder pattern corresponding to a nozzle which belongs to the range of candidate nozzles including the candidates of the defective nozzle causing the streak.

The entire test chart image including the test charts 230M, 230C, and 230K is referred to as the defective nozzle specification chart. As such, the defective nozzle specification chart using the overlay method is output and image analysis is performed for a read image of the output result to specify a defective nozzle. Then, an image quality correction process is performed for the specified defective nozzle to obtain a high-quality printed image in which the occurrence of a streak has been prevented in the output of page number "Page j+2" in FIG. 20.

[Procedure of Generating Defective Nozzle Specification Chart Using Overlay Method]

Figure 21:
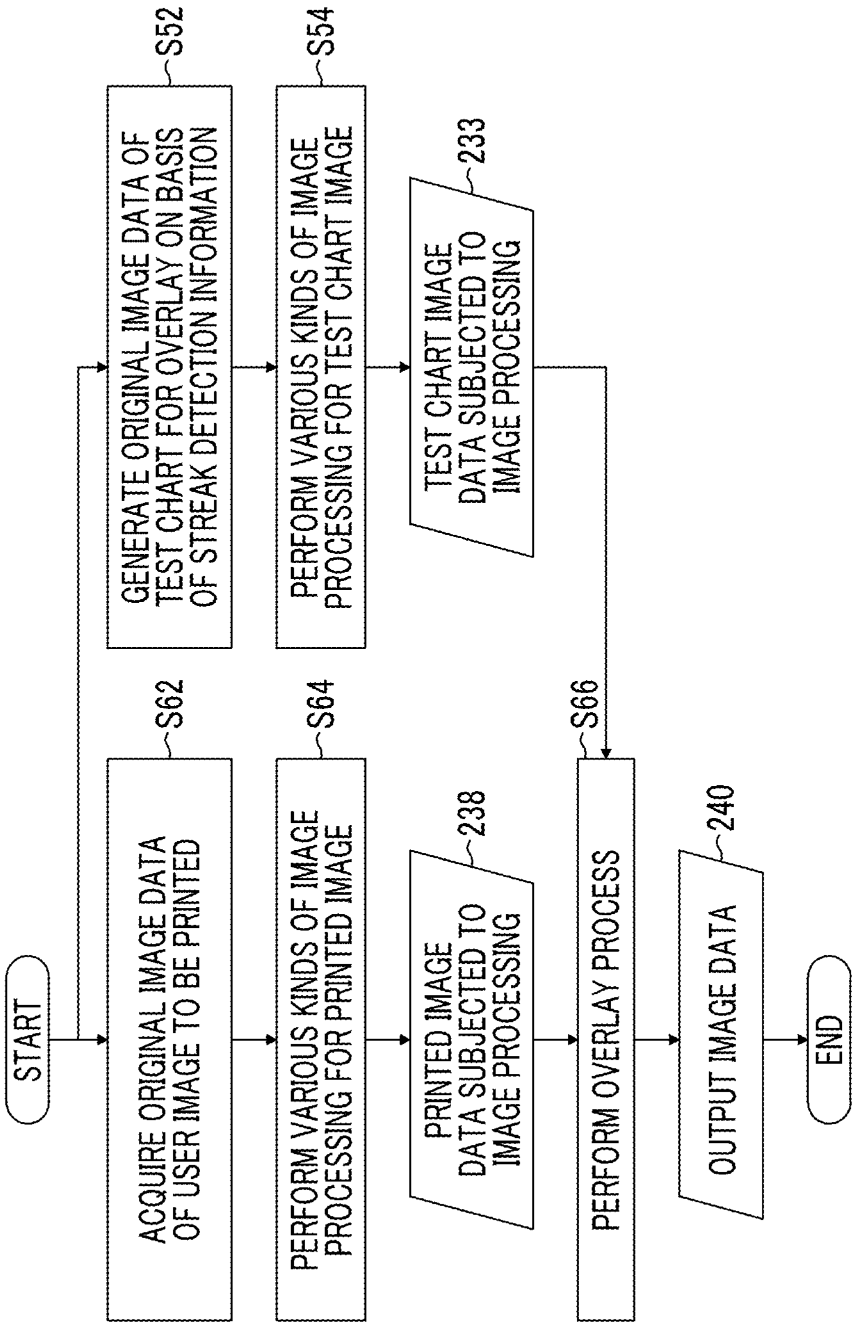
FIG. 21 is a flowchart illustrating a process of generating the defective nozzle specification chart using the overlay method.

FIG. 21 is a flowchart illustrating a procedure of generating the defective nozzle specification chart using the overlay method. Each step of the flowchart illustrated in FIG. 21 is performed by the control device 100 which functions as an image inspection device.

When the defective nozzle specification chart generation process illustrated in FIG. 21 starts, in Step S52, the control device 100 generates original image data of a test chart for overlay, on the basis of streak detection information generated from data of the read image read by an image reading device. The streak detection information indicates information about the streak detected by the streak detection processing unit 144. The streak detection information includes, for example, streak position information indicating the position of the streak or streak color information. The test chart for overlay is a defective nozzle specification test chart and is, for example, a chart image with a pattern in which the test charts 230M, 230C, and 230K with the ladder patterns illustrated in FIG. 20 are arranged so as to correspond to the positions of the streaks.

Figure 22:
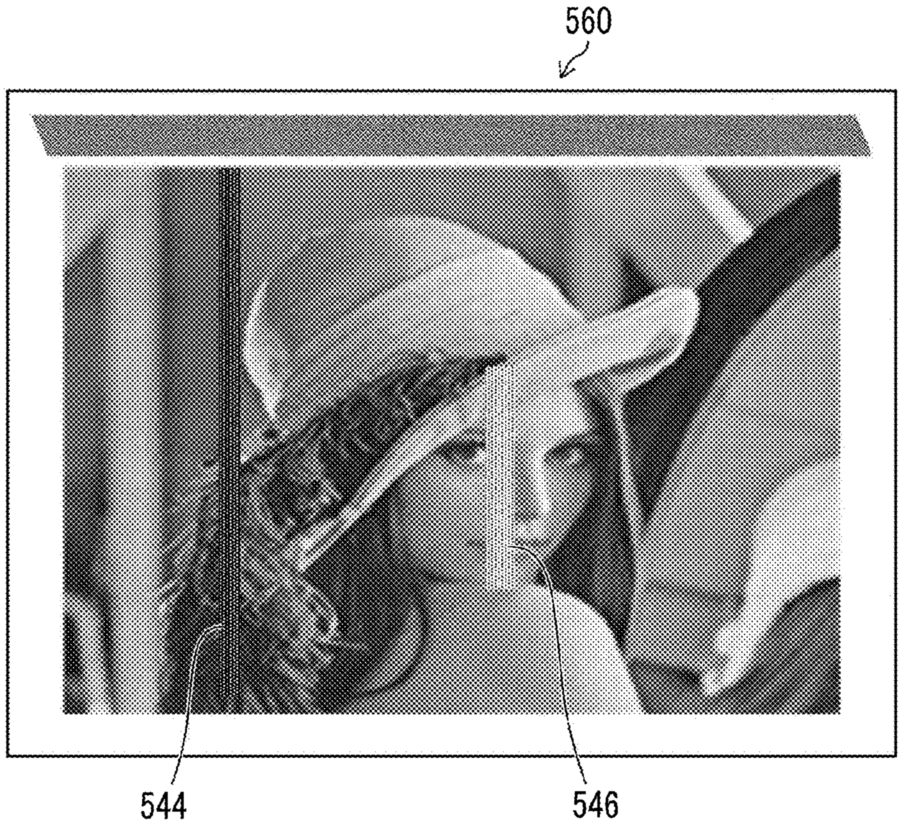
FIG. 22 illustrates an example of data of a read image obtained by an image reading device during continuous printing.
Figure 23:
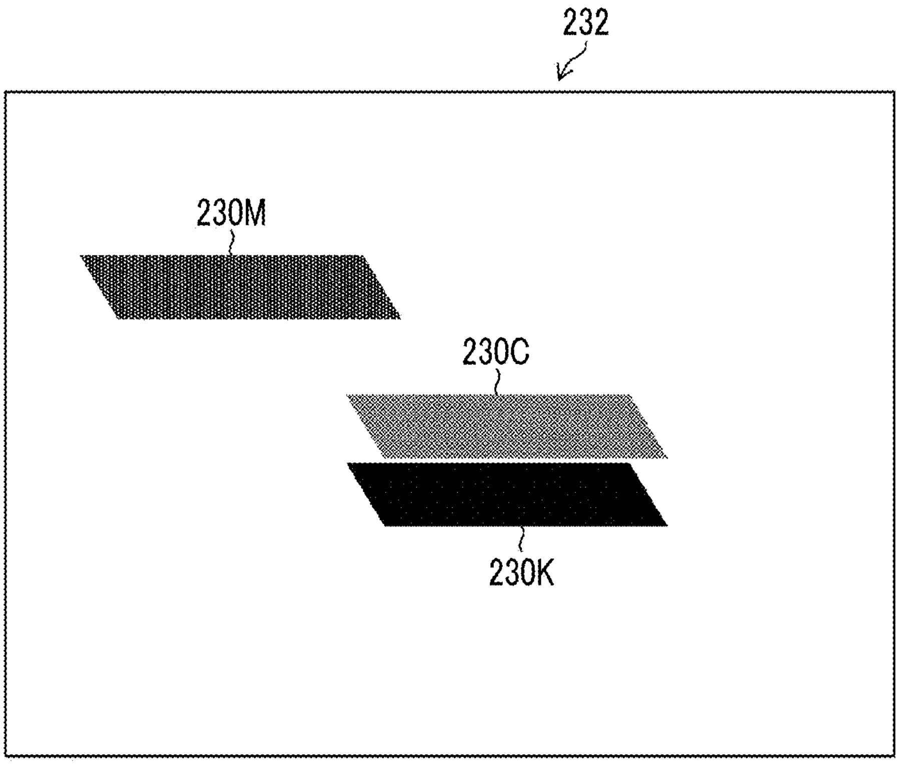
FIG. 23 illustrates an example of original image data of a test chart for overlay.

FIG. 22 illustrates an example of the data of the read image 560 obtained by the image reading device 48 during continuous printing. FIG. 23 illustrates an example of the original image data of the test chart for overlay generated in Step S52 in FIG. 21. The original image data of the test chart for overlay is referred to as test chart original image data.

Test chart original image data 232 illustrated in FIG. 23 includes data of the test chart 230M corresponds to the streak 544 and data of the test charts 230C and 230K corresponds to the streak 546. The test chart original image data 232 corresponds to an example of data of a test chart for interrupt output.

Then, in Step S54 in FIG. 21, the control device 100 performs various kinds of image processing for a test chart image for the test chart original image data 232. Examples of the image processing that can be applied to Step S54 include an image correction process, halftone processing, and a combination thereof. Step S54 is performed to generate test chart image data 233 subjected to image processing.

In parallel to Step S52 and Step S54 or before and after Step S52 and Step S54, various kinds of image processing for a test chart image are also applied to the original image data of the user image which is a printing target (Steps S62 and S64).

Figure 24:
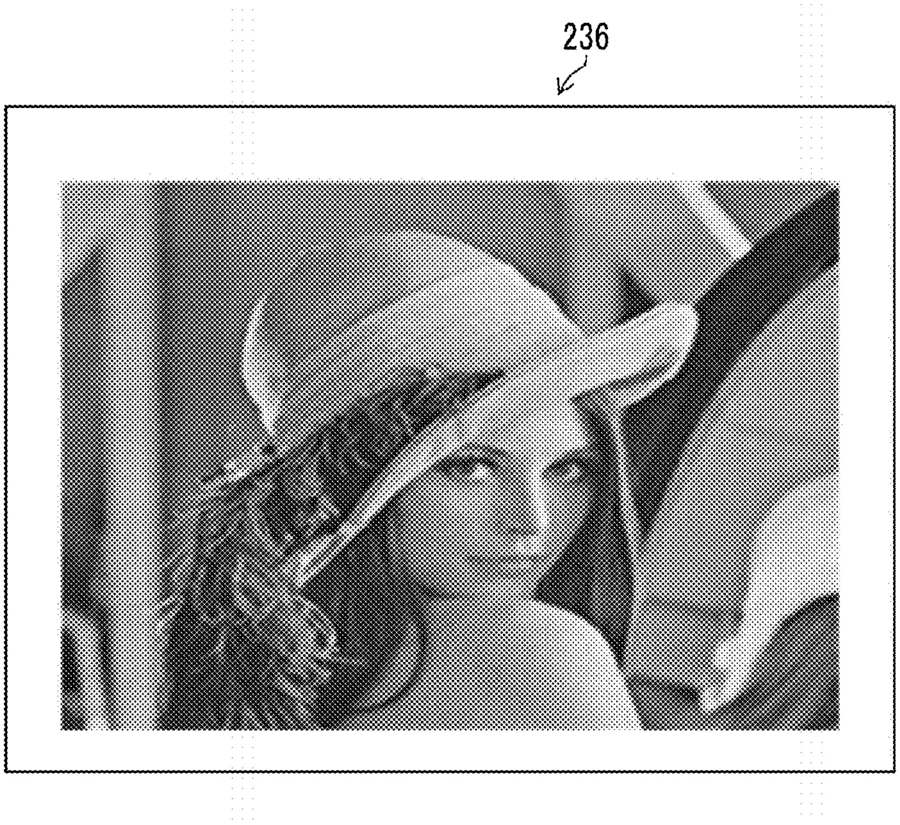
FIG. 24 illustrates an example of original image data of a user image.

That is, in Step S62, the control device 100 acquires the original image data of the user image which is a printing target. FIG. 24 illustrates an example of original image data 236 of the user image. The original image data 236 corresponds to an example of the printed image scheduled to be output during continuous printing.

Then, in Step S64 in FIG. 21, the control device 100 performs various kinds of image processing for a printed image for the original image data 236 of the user image. Examples of the image processing that can be applied to Step S64 include an image correction process, halftone processing, a defective nozzle detection pattern giving process, and a combination thereof. The content of various kinds of image processing applied to the original image data 236 of the user image in Step S64 and the content of various kinds of image processing applied to the test chart original image data 232 in Step S54 may include whether to apply image processing and may be different from each other.

For example, in Step S54, a dedicated image correction process and dedicated halftone processing for a test chart image are applied to the test chart original image data 232. In Step S64, an image correction process, halftone processing, and a defective nozzle detection pattern giving process for a printed image are applied to the original image data 236 of the user image.

The image processing applied to the original image data 236 of the user image in Step S64 corresponds to an example of first image processing. The image processing applied to the test chart original image data 232 in Step S54 corresponds to an example of second image processing.

Figure 25:
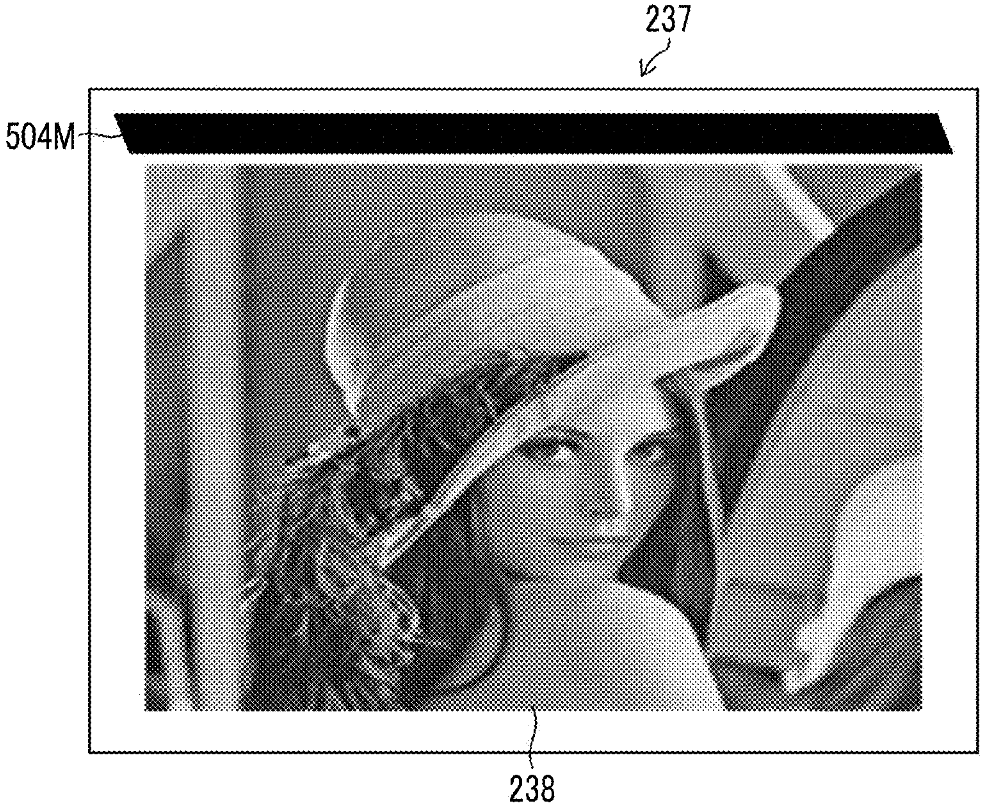
FIG. 25 illustrates an example of printed image data subjected to image processing.

Step S64 is performed to generate printed image data 237 subjected to image processing. FIG. 25 illustrates an example of the printed image data 237 subjected to image processing. The printed image data 237 subjected to image processing is image data indicating the content of an image in which the ladder pattern 504M which is the defective nozzle detection pattern is added to the leading end of a dot pattern image 238 of the user image converted into a dot pattern by halftone processing. The printed image data 237 subjected to image processing corresponds to an example of image data subjected to the first image processing. The test chart image data 233 subjected to image processing corresponds to an example of image data subjected to the second image processing.

When the printed image data 237 subjected to image processing and the test chart image data 233 subjected to image processing are generated in this way, the control device 100 performs an overlay process in Step S66 of FIG. 21. The overlay process in Step S66 is an image combination process which overlays and combines the printed image data 237 subjected to image processing and the test chart image data 233 subjected to image processing. In other words, the overlay process may be referred to as an image combination process. The overlay process in Step S66 is performed to generate output image data 240.

Figure 26:
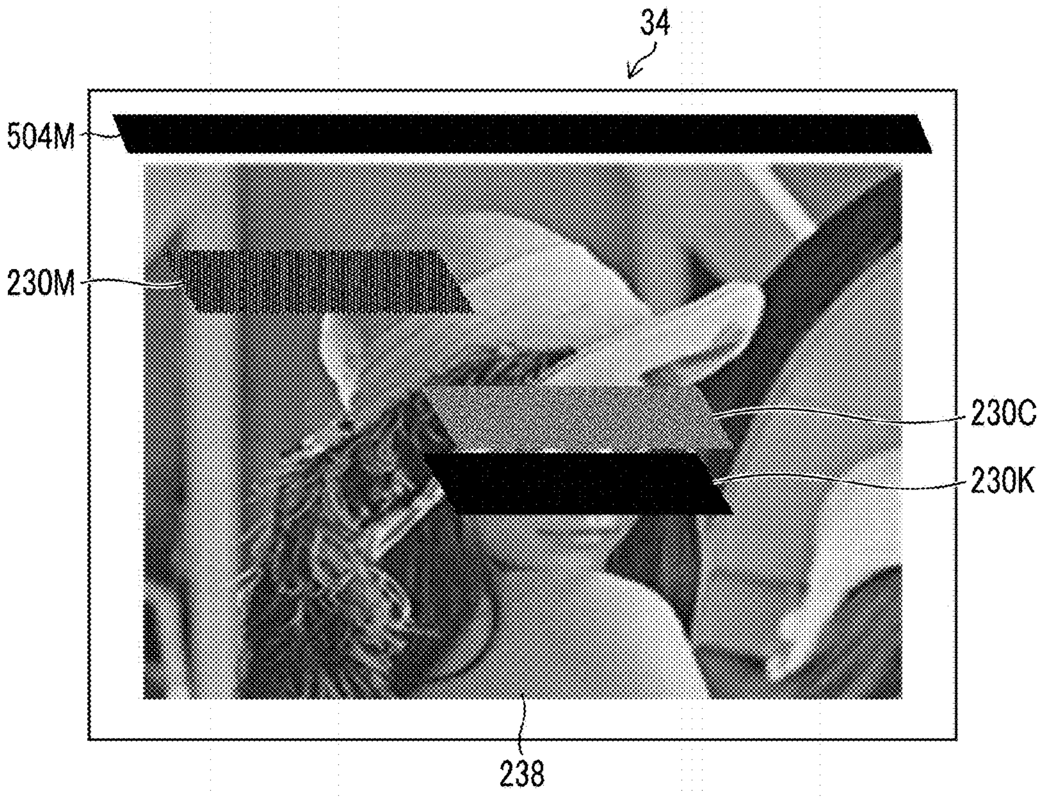
FIG. 26 illustrates an example of output image data generated through an overlay process.

FIG. 26 illustrates an example of the output image data 240 generated through the overlay process (Step S66). The output image data 240 corresponds to an example of composite image data. The output image data 240 is data indicating a composite image chart in which the test charts 230M, 230C, and 230K are incorporated into the user image.

The ink jet printing apparatus 1A prints out an image using the output image data 240 obtained by the execution of the flowchart illustrated in FIG. 21. The defective nozzle specification chart indicated by the output image data 240 corresponds to an example of a composite image chart in which the test chart is incorporated into one or more types of printed images scheduled to be output during continuous printing.

<<Post-Process after Defective Nozzle is Specified>>

Next, an example of a post-process performed after a defective nozzle is specified will be described.

[Image Quality Correction Process after Defective Nozzle is Specified]

An image quality correction process using the non jetting correction technique representatively disclosed in JP5457307B can be used as an example of a post-process after a defective nozzle is specified. In the technique disclosed in JP5457307B, it is assumed that defective nozzle correction parameters are prepared before continuous printing. The reason is that, when a process of optimizing the defective nozzle correction parameters is performed during continuous printing, productivity is reduced.

However, the state of the defective nozzle before continuous printing is not necessarily the same as the state of the defective nozzle when the defective nozzle occurs actually. Therefore, it is considered that the defective nozzle correction parameters prepared in advance are not the same as the amount of parameters for obtaining the optimal image quality.

For this reason, in a case in which image quality has priority over productivity, when the technique of the above-mentioned "interrupt process" is applied to specify a defective nozzle, it is considered that a process of printing an adjustment chart for optimizing the defective nozzle correction parameters, which is are parameters for correcting image quality caused by a corresponding defective nozzle, using the interrupt process and analyzing the adjustment chart to adjust the parameters to optimum values is effective in maintaining the highest image quality. The adjustment chart corresponds to an example of a test chart which is printed by the interrupt process during continuous printing.

For example, the technique disclosed in JP5111216B or the technique disclosed in JP5457307B is suitable as the technique using the process of adjusting the correction parameters to optimal values.

In addition, the number of types of test charts output by the interrupt process is not limited to 1 and a plurality of types of test charts may be output. For example, after a process which outputs the defective nozzle specification chart first using the interrupt process and specifies a defective nozzle is performed, adjustment parameters for adjusting the correction parameters may be output to adjust the correction parameters.

A read image obtained by reading the adjustment chart output by the interrupt process using the image reading device 48 corresponds to an example of a fourth read image. In addition, the configuration in which the correction parameters are adjusted using the adjustment chart and the image quality correction process is performed using the adjusted correction parameters corresponds to an example of a configuration in which the analysis result of the data of the fourth read image is reflected in a process of printing the printed image during continuous printing after the test chart is output by the interrupt process.

[Image Processing after Specification of Defective Nozzle Fails]

Figure 27:
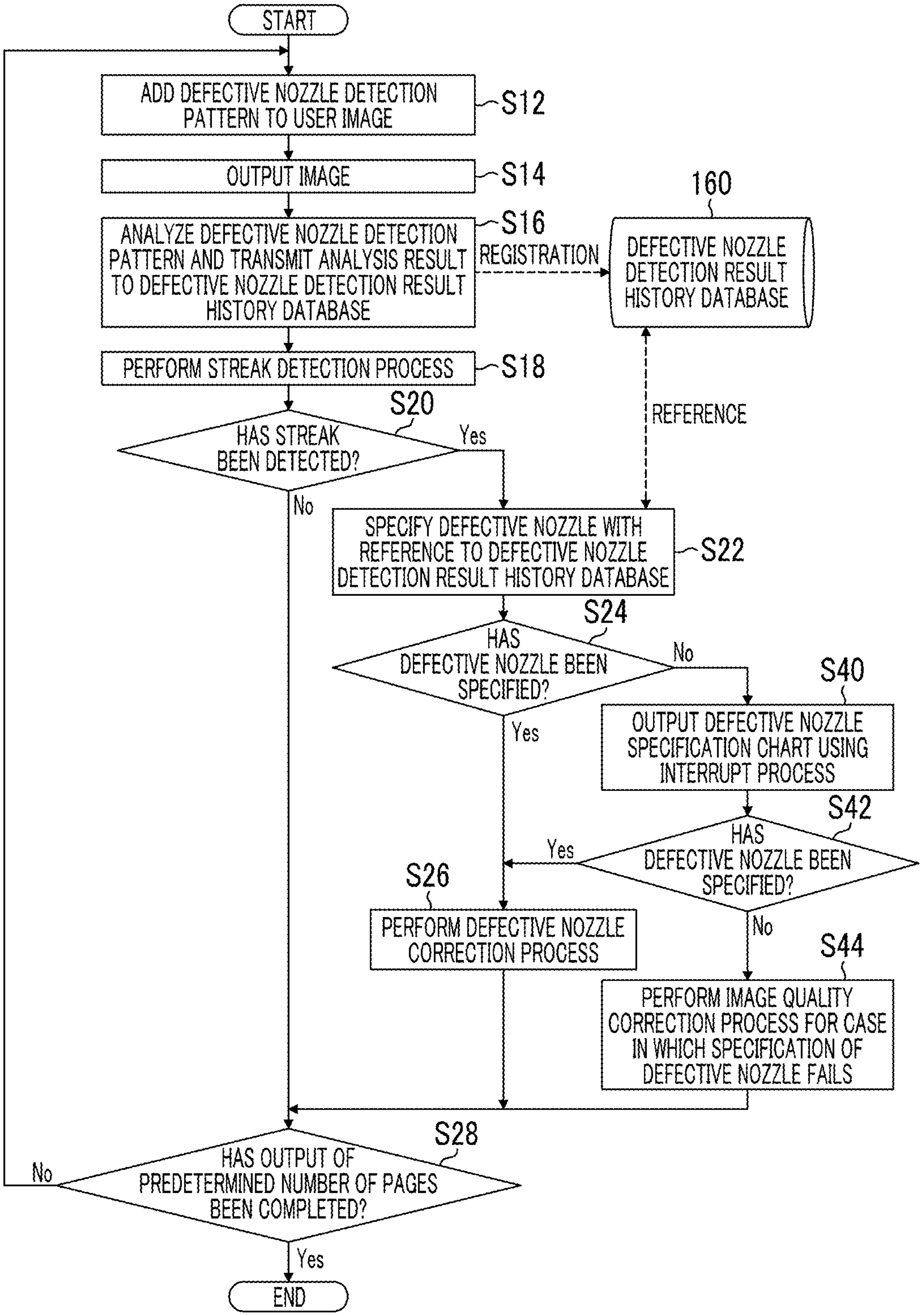
FIG. 27 is a flowchart illustrating an example of a printing process including image processing after the specification of a defective nozzle fails.

When the process ends due to abnormality in a state in which the specification of a defective nozzle fails, there is a concern that productivity will be significantly reduced. There is a user who gives priority to productivity and "does not want to reduce productivity instead of allowing a little degradation of image quality". It is considered to perform another image processing which can meet the user's requirements, is different from general image processing when the specification of a defective nozzle fails, and is most suitable for a case in which the specification of a defective nozzle fails. FIG. 27 illustrates an example of a process flow in this case.

FIG. 27 is a flowchart illustrating an example of a printing process including image processing after the specification of a defective nozzle fails. FIG. 27 illustrates a modification example of the flowchart illustrated in FIG. 18. In FIG. 27, the same or similar steps as those in the flowchart illustrated in FIG. 18 are denoted by the same step numbers and the description thereof will not be repeated.

In the flowchart illustrated in FIG. 27, Step S44 performed in a case in which the determination result of Step S42 is "No" is added.

In a case in which it is determined in Step S42 that a defective nozzle has not been specified and the determination result is "No", the control device 100 proceeds to Step S44. In Step S44, the control device 100 performs an image quality correction process for a case in which the specification of a defective nozzle fails. The image quality correction process for a case in which the specification of a defective nozzle fails is an image quality correction process applied to the case in which the specification of a defective nozzle fails. The image quality correction process for a case in which the specification of a defective nozzle fails which is applied as measures to the case in which the specification of a defective nozzle fails is an image quality correction process different from the defective nozzle correction process performed in Step S26. The image quality correction process for a case in which the specification of a defective nozzle fails corresponds to an example of a second image quality correction process. The defective nozzle correction process performed in Step S26 is an image quality correction process applied to the printed image to be output after the specification of a defective nozzle succeeds and corresponds to an example of a first image quality correction process.

A "plural-non-jetting correction" processes can be used as an example of the image quality correction process for a case in which the specification of a defective nozzle fails in Step S44. Next, the outline of the plural-non-jetting correction processes will be described.

Detailed Example of Image Quality Correction Process for Case in which Specification of Defective Nozzle Fails Plural-non-jetting correction means a correction method that disables two or more nozzles with respect to one defective nozzle and performs correction. A set of two or more nozzles is referred to as a nozzle group. In contrast, the defective nozzle correction process performed in Step S26 is a single-non-jetting correction process. The single-non-jetting correction is a correction method that disables a specific nozzle with respect to one defective nozzle and performs correction.

Disabling a nozzle means a process of prohibiting the use of a nozzle. The disabled nozzle is in a state in which the nozzle is not capable of jetting liquid droplets and becomes a non-jetting nozzle. In other words, the term "disabling a nozzle" can be referred to as making a nozzle incapable of jetting or making a nozzle unavailable. The nozzle in the disabled state is referred to as a disabled nozzle. The process of disabling a nozzle and performing correction means a process of performing correction such that a non-jetting portion is not visible.

The process of performing correction such that a non-jetting portion is not visible means a process of performing correction for reducing the visibility of a streak such that the streak caused by the non-jetting nozzle is not visible during printing. The non-jetting portion is a missing portion in which no dot is recorded due to the disabled nozzle. In the case of the single pass method, the non-jetting portion is a streak.

An operation mode in which correction is performed by the single-non-jetting correction function is referred to as a single-non-jetting correction mode. An operation mode in which correction is performed by the plural-non-jetting correction function is referred to as a plural-non-jetting correction mode. In a case in which it is difficult to specify one defective nozzle in a state in which a streak occurs due to the defective nozzle, the plural-non-jetting correction mode in which a nozzle group within a nozzle range corresponding to a region including abnormality is disabled and correction is performed is used.

Non-jetting correction may be performed for each nozzle group in the plural-non-jetting correction mode to prevent the generation of a waste sheet. In this state, printing may be continuously performed. Then, in a case in which it is possible to really specify a defective nozzle, the correction mode may be switched to the single-non-jetting correction mode.

Next, the content of the plural-non-jetting correction process will be described.

<For Detection of Image Abnormality and Method for Setting Abnormal Region>

Figure 28:
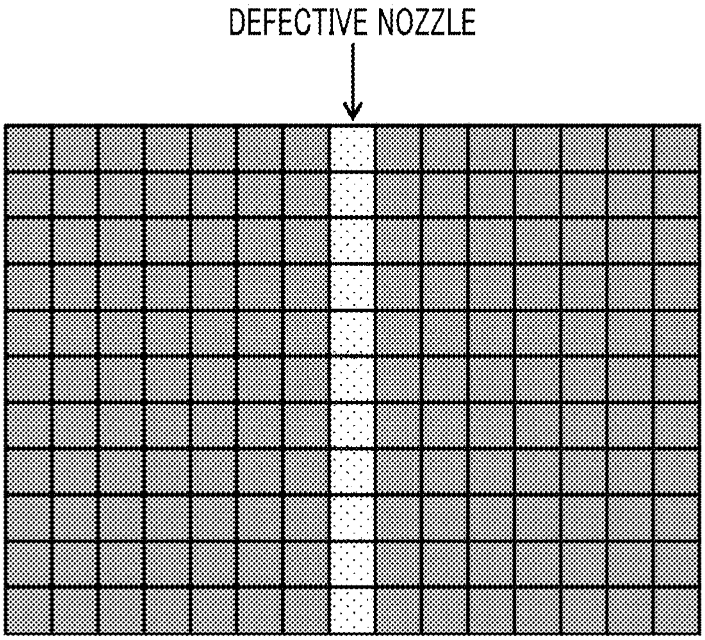
FIG. 28 is a diagram schematically illustrating a printed image in a case in which abnormality is detected from the printed image.

FIG. 28 is a diagram schematically illustrating a printed image in a case in which abnormality is detected from the printed image. Each cell indicates a pixel of the printed image. In FIG. 28, the horizontal direction is the X direction and the vertical direction is the Y direction. Nozzles which are in charge of recording pixels are associated with the pixels arranged in the X direction. Therefore, the position of the pixel in the X direction can be understood as the position of the nozzle.

The nozzle that is in charge of recording an eighth column of pixel positions from the left in FIG. 28 is a defective nozzle. A streak that extends in the Y direction occurs at a corresponding image position due to the defective nozzle. In FIG. 28, a pixel column of an image portion which is the streak is displayed so as to be lightly shaded.

Figure 29:
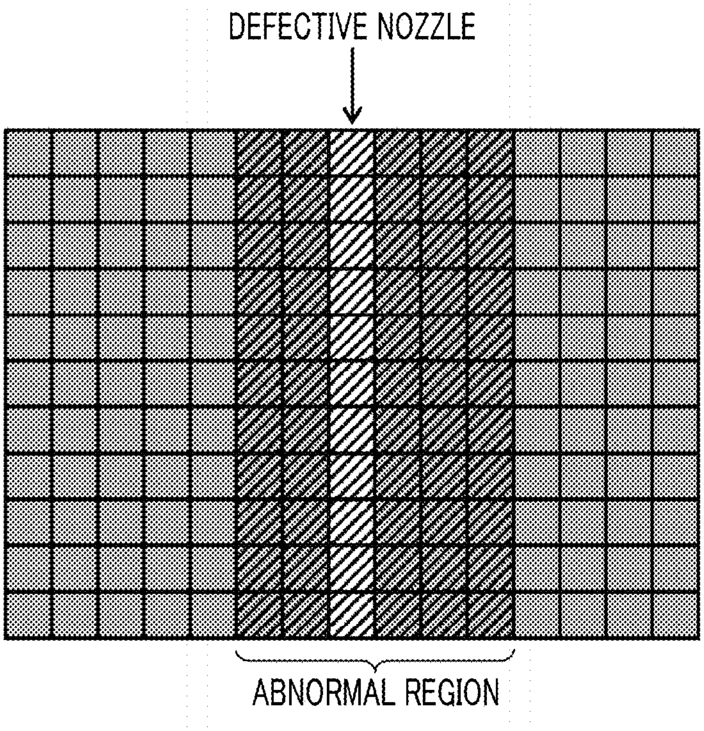
FIG. 29 is a diagram schematically illustrating an aspect in which an abnormal region including the position of a defective nozzle is set.

FIG. 29 is a diagram schematically illustrating an aspect in which an abnormal region including the position of a defective nozzle is set. FIG. 29 illustrates an example in which an image region corresponding to a nozzle range of six nozzles which are suspected to be defective nozzles is set as an abnormal region on an image. In the example illustrated in FIG. 29, a region corresponding to six consecutive pixels in the X direction is set as the abnormal region. However, the pixel range set as the abnormal region can be set to an appropriate range including one or more pixels according to the resolution of the image reading device.

A process of setting the abnormal region is performed when the plural-non-jetting correction is performed.

<For Method for Specifying Nozzle Group Including Defective Nozzle>

Figure 30:
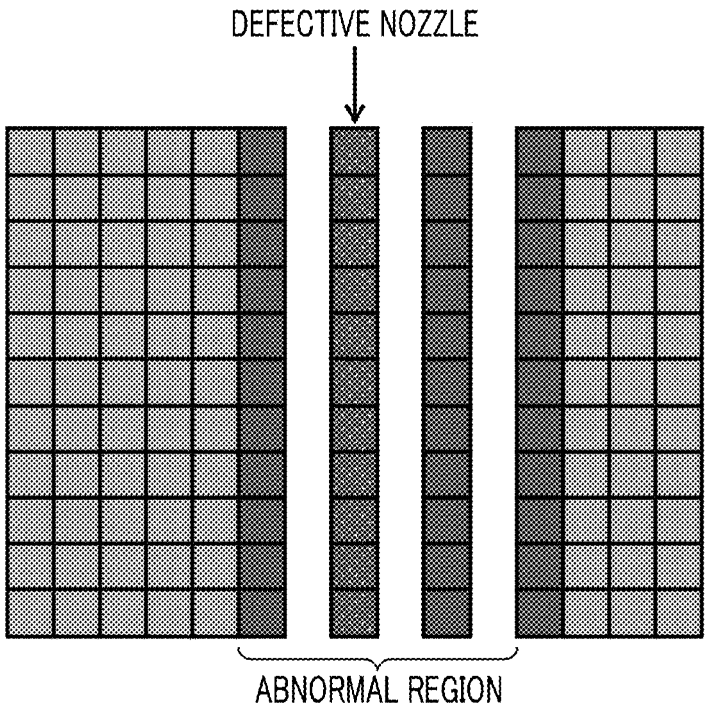
FIG. 30 is a diagram schematically illustrating an aspect in which a first nozzle group belonging to a nozzle range corresponding to the abnormal region is disabled and plural-non-jetting correction is performed.

Next, a detailed example of a nozzle group search method for specifying a nozzle group including a defective nozzle will be described. FIG. 30 is a diagram schematically illustrating an aspect in which a first nozzle group within a nozzle range corresponding to an abnormal region is disabled and plural-non-jetting correction is performed. In FIG. 30, the disabled first nozzle group is, for example, an odd-numbered nozzle group. For simplicity of explanation, it is assumed that the column number of pixels is matched with a nozzle number in such a way that the nozzle number of a nozzle which is in charge of recording a first column of pixels from the left end of FIG. 30 is "1" and a nozzle which is in charge of recording a second column of pixels has nozzle number 2. The abnormal region corresponds to a range of nozzle number 6 to nozzle number 11. The odd-numbered nozzle group in the abnormal region includes nozzles with nozzle numbers 7, 9, and 11.

In the example illustrated in FIG. 30, the odd-numbered nozzle group including nozzles with nozzle number 7, 9, and 11 is disabled and non jetting correction is performed using nozzles adjacent to the disabled nozzles. In this case, a nozzle with nozzle number 8, which is a defective nozzle, is used for non-jetting correction. However, since the nozzle with nozzle number 8 used for correction is a defective nozzle, an appropriate correction effect is not obtained and a streak is visibly recognized from the image. That is, non jetting correction for the odd-numbered nozzle group in the plural-non-jetting correction mode fails.

Figure 31:
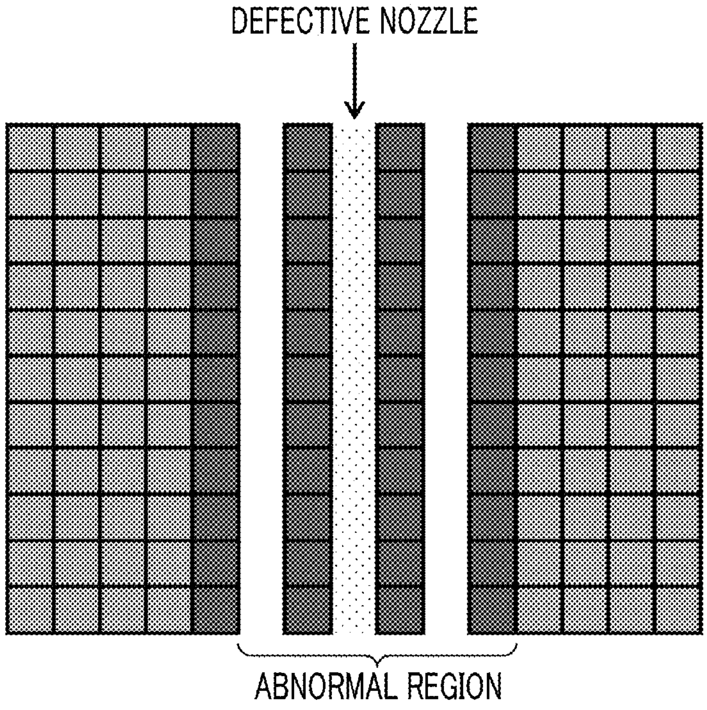
FIG. 31 is a diagram schematically illustrating an aspect in which a second nozzle group belonging to the nozzle range corresponding to the abnormal region is disabled and plural-non-jetting correction is performed.

FIG. 31 is a diagram schematically illustrating an aspect in which a second nozzle group within a nozzle range corresponding to an abnormal region is disabled and plural-non-jetting correction is performed. In FIG. 31, the disabled second nozzle group is, for example, an even-numbered nozzle group. The even-numbered nozzle group in the abnormal region includes nozzles with nozzle numbers 6, 8, and 10.

In the example illustrated in FIG. 31, the even-numbered nozzle group including nozzles with nozzle number 6, 8, and 10 is disabled and non-jetting correction is performed using nozzles adjacent to the disabled nozzles. In this case, a nozzle with nozzle number 8, which is a defective nozzle, is disabled and non-jetting correction is performed using other normal nozzles. Therefore, a high-quality image in which a streak is invisible is obtained by a non-jetting correction effect. That is, non-jetting correction for the even-numbered nozzle group in the plural-non-jetting correction mode succeeds. In this way, it is checked that a defective nozzle belongs to the even-numbered nozzle group.

As described in FIGS. 30 and 31, non-jetting correction is performed while switching a nozzle group to determine which nozzle group a defective nozzle belongs to. In a case in which a defective nozzle is included in a disabled nozzle group, the defective nozzle is appropriately corrected. However, in a case in which a defective nozzle is not included in the nozzle group, a streak occurs. It is possible to determine whether or not appropriate correction is performed by reading an image of a user image region using the image reading device and analyzing and inspecting the read image.

A correction mode in which an odd-numbered nozzle group is disabled and correction is performed is referred to as an odd-numbered nozzle group correction mode. A correction mode in which an even-numbered nozzle group is disabled and correction is performed is referred to as an even-numbered nozzle group correction mode. In a plural-non-jetting correction process, a correction operation in the even-numbered nozzle group non-jetting correction mode and a correction operation in the odd-numbered nozzle group non-jetting correction mode can be selectively performed.

Assuming that the defective nozzle is not restored, the defective nozzle certainly belongs to one of the even-numbered nozzle group and the odd-numbered nozzle group. Therefore, when correction is performed in one of the even-numbered nozzle group correction mode and the odd-numbered nozzle group correction mode, it is possible to specify the nozzle group including the defective nozzle according to whether there is abnormality in the corrected image. Therefore, for example, when it is confirmed that non-jetting correction in the odd-numbered nozzle group non-jetting correction mode has failed as illustrated in FIG. 30, it may be determined that the defective nozzle belongs to the even-numbered nozzle group.

In each of the odd-numbered nozzle group correction mode and the even-numbered nozzle group correction mode, every other nozzle in the X direction is disabled. In FIGS. 30 and 31, the nozzle groups are divided into two types of nozzle groups, that is, the odd-numbered nozzle group and the even-numbered nozzle group. However, a method for determining a nozzle group is not limited to this example. Three or more types of nozzle groups may be used. For example, every two nozzles form a nozzle group or every three nozzles form a nozzle group. In this embodiment, plural-non-jetting correction using plural-non-jetting correction means disables a plurality of nozzles which are discontinuously arranged in the X direction and reduces the visibility of a missing portion using the remaining nozzles other than the disabled nozzles.

[Another Method for Specifying Nozzle Group Including Defective Nozzle]

Figure 32:
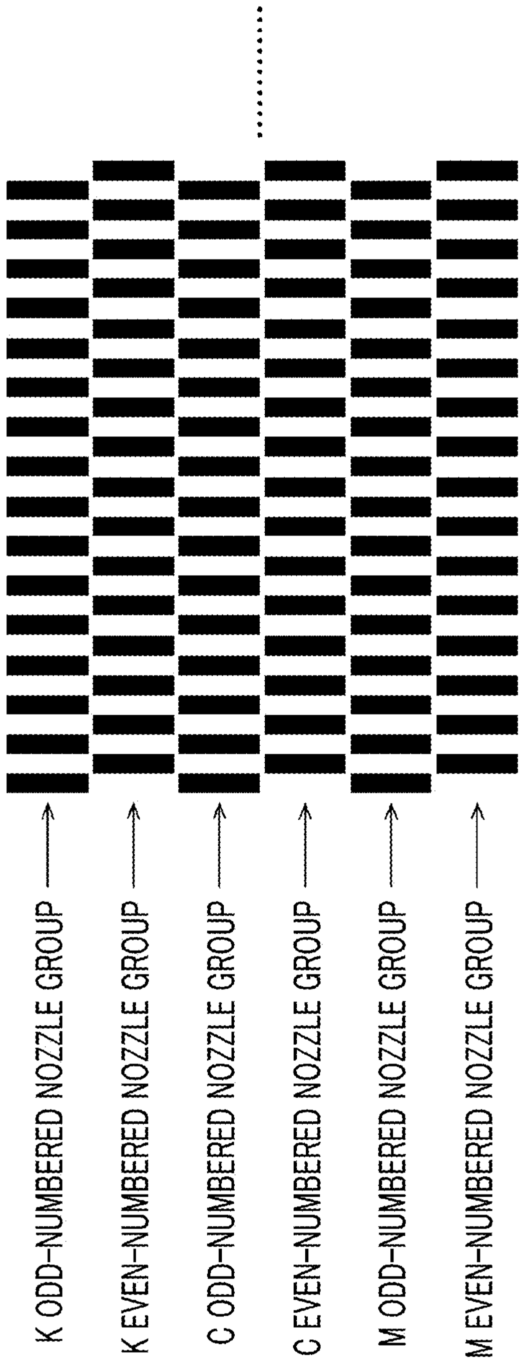
FIG. 32 illustrates an example of a nozzle group specification chart.

As another method for specifying a nozzle group including a defective nozzle, there is a method which uses a dedicated test chart for specifying the nozzle group. FIG. 32 illustrates an example of a nozzle group specification chart.

In FIG. 32, a pattern in a first stage from the top is a line group pattern recorded by an odd-numbered nozzle group of the ink jet head that jets black ink. A pattern in a second stage is a line group pattern recorded by an even-numbered nozzle group of the ink jet head that jets black ink. Black is represented by K.

A pattern in a third stage is a line group pattern recorded by an odd-numbered nozzle group of the ink jet head that jets cyan ink. A pattern in a fourth stage is a line group pattern recorded by an even-numbered nozzle group of the ink jet head that jets cyan ink. Cyan is represented by C.

A pattern in a fifth stage is a line group pattern recorded by an odd-numbered nozzle group of the ink jet head that jets magenta ink. A pattern in a sixth stage is a line group pattern recorded by an even-numbered nozzle group of the ink jet head that jets magenta ink. Magenta is represented by M. The nozzle group specification chart includes a chart in which the colors of ink jetted between the nozzle groups are different from each other.

FIG. 32 is a schematic enlarged view and illustrates only some of the line groups. However, all of the nozzles of the ink jet head are used to print the nozzle group specification chart.

As illustrated in FIG. 32, it is possible to specify a nozzle group including a defective nozzle by outputting a line chart in which nozzle groups have different stage configurations, specifying which stage abnormality occurs in, and associating the stage with a corresponding nozzle group.

When abnormality has been detected from an image on the basis of the inspection result of a user image region, there are two cases, that is, a case in which it is possible to specify which color nozzle abnormality occurs in and a case in which it is difficult to specify which color nozzle abnormality occurs in. In the case in which it is difficult to specify which color nozzle abnormality occurs in, the nozzle group specification chart illustrated in FIG. 32 is printed to determine the color of the defective nozzle and the nozzle group including the defective nozzle.

<For Single Nozzle Specification Method>

Next, a detailed example of a single nozzle specification method for specifying a defective nozzle will be described. It is possible to determine a single nozzle which is a defective nozzle on the basis of the inspection result of the defective nozzle detection pattern drawn in a nozzle inspection region while a nozzle group is being searched for or after the nozzle group is searched for.

As still another method, the disabled nozzles which belong to the nozzle group subjected to plural-non-jetting correction are sequentially restored to an enabled state one by one and each corrected image is analyzed to detect abnormality in the image on the user image. In this way, it is possible to specify a defective nozzle. In this case, a waste sheet with abnormal image quality is generated only when the defective nozzle is released. It is possible to specify a defective nozzle, using control for restoring the disabled nozzle to the enabled state and image analysis for the user image region.

A method for specifying a defective nozzle from the user image will be described with reference to FIGS. 33 to 36.

Figure 33:
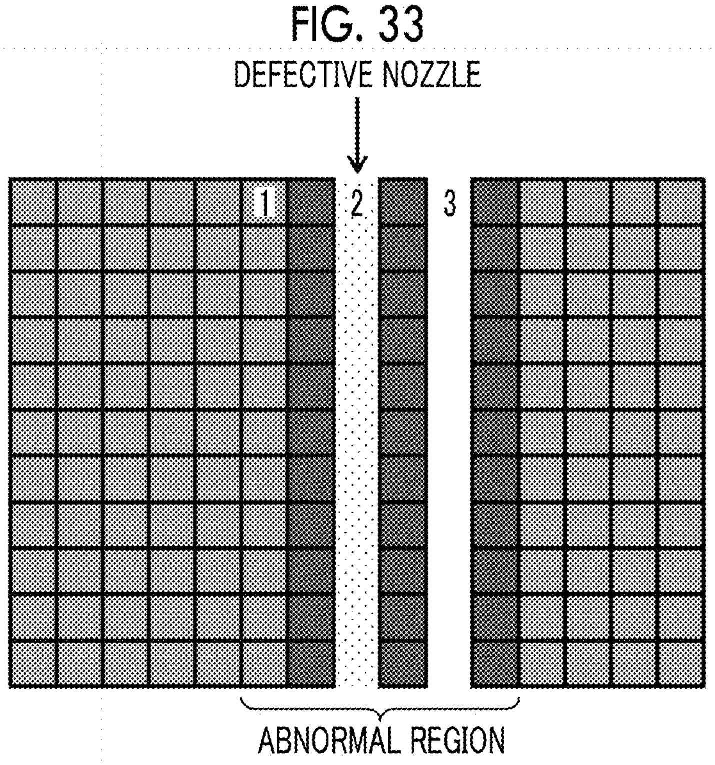
FIG. 33 is a diagram schematically illustrating an example in which one nozzle of the nozzle group disabled in FIG. 31 is restored to an enabled state.

FIG. 33 illustrates an aspect in which a nozzle with nozzle number 6 which is in a disabled state is restored to an enabled state, in a state in which plural-non-jetting correction for the nozzle group described in FIG. 31 has succeeded. In the example illustrated in FIG. 33, a nozzle group including a defective nozzle in an abnormal region includes three nozzles with nozzle numbers 6, 8, and 10. Therefore, the three nozzles are the candidate nozzles of the defective nozzle. It is assumed that the nozzles with nozzle numbers 6, 8, and 10 are referred to as candidate nozzles 1, 2, and 3 in this order. In FIG. 33, numbers "1", "2", and "3" indicates the positions of the candidate nozzles 1, 2, and 3, which holds for FIGS. 34 to 36.

As illustrated in FIG. 33, the candidate nozzle 1 in a disabled state is restored to an enabled state and the candidate nozzles 2 and 3 are maintained in a disabled state. In this state, when correction is performed for a nozzle group including the candidate nozzles 2 and 3 in the plural-non-jetting correction mode, a high-quality image in which a streak is invisible is obtained by the effect of the non jetting correction. That is, the candidate nozzle 1 is determined not to be a defective nozzle and a defective nozzle has not been specified.

Figure 34:
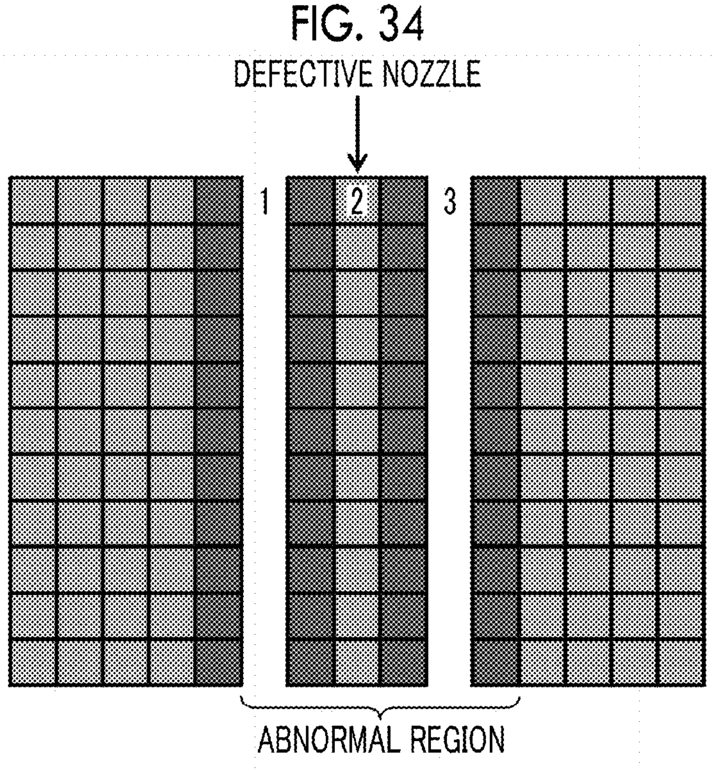
FIG. 34 is a diagram schematically illustrating an example in which one nozzle of the nozzle group disabled in FIG. 31 is restored to an enabled state.

FIG. 34 illustrates an aspect in which the candidate nozzle 2, that is, the nozzle with nozzle number 8 in a disabled state is restored to an enabled state, in a state in which plural-non-jetting correction for the nozzle group described in FIG. 31 has succeeded. As illustrated in FIG. 34, the candidate nozzle 1 in a disabled state is restored to an enabled state and the candidate nozzles 1 and 3 are maintained in a disabled state. In this state, when correction is performed for a nozzle group including the candidate nozzles 1 and 3 in the plural-non-jetting correction mode, an image in which a streak is visible is obtained since the candidate nozzle 2 restored from the disabled state is a defective nozzle. That is, the non-jetting correction fails and the candidate nozzle 2 is specified to be a defective nozzle.

Figure 35:
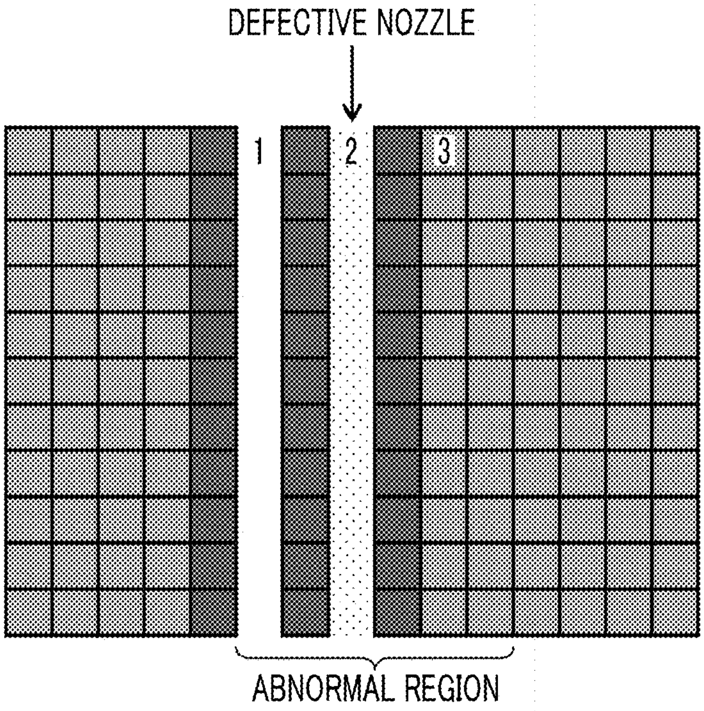
FIG. 35 is a diagram schematically illustrating an example in which one nozzle of the nozzle group disabled in FIG. 31 is restored to an enabled state.

FIG. 35 illustrates an aspect in which the candidate nozzle 3, that is, the nozzle with nozzle number 10 in a disabled state is restored to an enabled state, in a state in which plural-non-jetting correction for the nozzle group described in FIG. 31 has succeeded. As illustrated in FIG. 35, the candidate nozzle 3 in a disabled state is restored to an enabled state and the candidate nozzles 1 and 2 are maintained in a disabled state. In this state, when correction is performed for a nozzle group including the candidate nozzles 1 and 2 in the plural-non-jetting correction mode, a high-quality image in which a streak is invisible is obtained by the effect of the non-jetting correction. That is, the candidate nozzle 3 is determined not to be a defective nozzle and a defective nozzle has not been specified.

The processes in FIGS. 33, 34, and 35 may be performed in any order. In a case in which the candidate nozzles 1, 2, and 3 in the disabled state are sequentially restored to the enabled state in this order, since a defective nozzle is specified in a stage in which the candidate nozzle 2 in the disabled state is restored to the enabled state, it is possible to omit the execution of plural-non-jetting correction for restoring the candidate nozzle 3 in the disabled state to the enabled state described in FIG. 35. That is, when a defective nozzle is specified, it is possible to omit a process for the remaining candidate nozzles.

In a case in which it is confirmed that the candidate nozzle 1 is not a defective nozzle in FIG. 33, when the next candidate nozzle 2 in the disabled state is restored to the enabled state, the candidate nozzle 1 may not be disabled. Among the candidate nozzles, a nozzle which is in a disabled state and has been confirmed not to be a defective nozzle may be restored to the enabled state. After the specification of the defective nozzle is completed, it is preferable that the specified defective nozzle is maintained in the disabled state and the other nozzles in the disabled state are restored to the enabled state. Then, the specified defective nozzle is disabled and correction is performed in the single-non-jetting correction mode.

Figure 36:
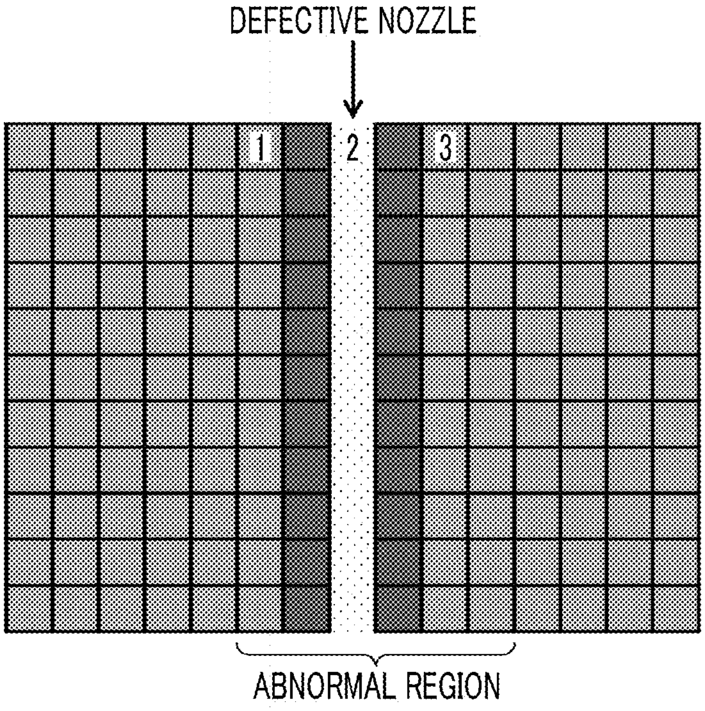
FIG. 36 is a diagram schematically illustrating an aspect in which a specified defective nozzle is disabled and single-non-jetting correction is performed.

FIG. 36 illustrates an aspect in which a specified defective nozzle is disabled and single-non-jetting correction is performed. In FIG. 36, the candidate nozzles 1 and 3 in the disabled state are restored to the enabled state. The defective nozzle is disabled and a high-quality image in which a streak is invisible is obtained by the effect of the single-non-jetting correction.

The use of the above-mentioned method makes it possible to specify a streak that occurs on a user image and to perform correction while minimizing the generation of a waste sheet.

Example of Method for Setting Correction Parameters

A correction method using any of the single-non-jetting correction mode and the plural-non-jetting correction mode uses a method which detects abnormality in nozzles, disables a nozzle corresponding to an abnormal portion, and fills a portion corresponding to the disabled nozzle with liquid droplets jetted from neighboring nozzles as an image correction method for preventing a streak caused by abnormality in the nozzle from being seen. For example, a method disclosed in JP5597680B can be used as a method for correcting a streak caused by a defective nozzle. The method disclosed in JP5597680 outputs a chart obtained when a case in which each nozzle is disabled is simulated, determines the correction intensity of nozzles in the vicinity of the non-jetting nozzle such that the chart is flattened, and determines correction parameters when liquid droplets are not jetted.

Figure 37:
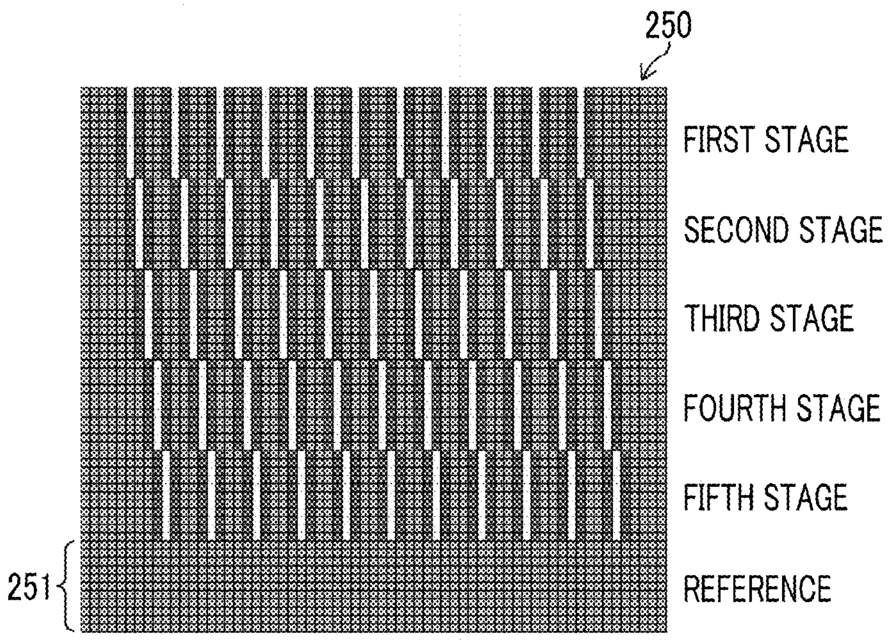
FIG. 37 is a diagram schematically illustrating a single-non-jetting correction parameter calculation chart.

FIG. 37 is a diagram schematically illustrating a single-non-jetting correction parameter calculation chart 250. In practice, a white streak illustrated in FIG. 37 is invisible. However, for ease of understanding, the white streak is displayed so as to be visible. In FIG. 37, cells of pixels are drawn. However, there is no compartment line between the cells in the actual chart. This holds for FIG. 38.

In the single-non-jetting correction parameter calculation chart 250 illustrated in FIG. 37, a pattern having a simulated non-jetting region in which non-jetting is simulated for every N nozzles is arranged in N stages in a solid image region in gradation that is desired to be optimized. N is a natural number. FIG. 37 illustrates an example in which N is 5. The "solid image region" means a "constant-density region". In addition, a non-jetting correction region adjacent to each simulated non-jetting region has density obtained by applying non-jetting correction parameters to the density of the content-density region.

In order to form the single-non-jetting correction parameter calculation chart 250, data in the first stage of the chart causes every N first nozzles arranged in a direction perpendicular to the transport direction of a sheet not to jet ink and to form a simulated non-jetting region, causes the second nozzles adjacent to both sides of the first nozzles to form a non-jetting correction region on the basis of a command value corrected by the non jetting correction parameters, and causes the third nozzles other than the first nozzles and the second nozzles to form the constant-density region on the basis of a command value which has not been corrected. The first nozzle corresponds to a "simulated non jetting nozzle". The second nozzle corresponds to a "non jetting correction nozzle".

That is, the single-non-jetting correction parameter calculation chart 250 includes the simulated non-jetting region formed by the first nozzle, the non-jetting correction region formed by the second nozzles adjacent to both sides of the first nozzle, and the constant-density region formed by the third nozzle other than the first nozzle and the second nozzle.

A plurality of first stages in which the simulated non-jetting regions are arranged at a predetermined interval in the first direction are arranged in the second direction perpendicular to the first direction and the simulated non-jetting regions in a plurality of stages are arranged at different positions in the first direction.

In addition, the data of the single-non-jetting correction parameter calculation chart 250 causes the first nozzles not to jet ink, causes the third nozzles to jet ink on the basis of a command value indicating predetermined density, and causes the second nozzles to jet ink on the basis of a command value obtained by correcting the command value indicating the predetermined density with the non-jetting correction parameters of an adjacent first nozzle.

Specifically, when a command value for gradation that is desired to be optimized is D and the nozzle number of the first nozzle is i, the data causes the first nozzle not to jet ink, causes the second nozzles with nozzle numbers i−1 and i+1 to jet ink on the basis of a command value of D×mi, and causes the third nozzles with nozzle numbers i−N+1, i−3, i−2, i+2, i+3, . . . , i+N−1 to jet ink on the basis of a command value of D. The nozzle numbers are integer numbers which are uniquely given to the nozzles in the order in which the nozzles are arranged in the X direction in the ink jet head. In addition, "mi" is a non-jetting correction parameter indicating the correction intensity of each nozzle.

In each stage of the single-non-jetting correction parameter calculation chart, the first nozzles are arranged so as to be shifted in the nozzle array direction. In the example illustrated in FIG. 37, the first nozzles with nozzle numbers i, i+1, i+2, i+3, and i+4 are arranged in the first to fifth stages, respectively. As such, since the first nozzles in each stage are arranged so as to be shifted in the nozzle array direction, it is possible to make all of the nozzles function as the simulated non-jetting nozzles. Therefore, it is possible to evaluate the non-jetting correction parameters of all of the nozzles.

The single-non-jetting correction parameter calculation chart 250 may be provided with a reference density stage 251 as illustrated in FIG. 37. In the reference density stage 251, the constant-density region in gradation that is desired to be optimized is drawn by all of the nozzles. In a case in which the reference density stage 251 is provided, a difference between scanning density in the vicinity of the simulated non-jetting region and the scanning density of the reference density stage can be used as a correction intensity evaluation value. In this case, it is possible to offset unevenness in the shading or resolution of the image reading device in the nozzle direction and to reduce the influence of low-frequency streak unevenness peculiar to the single pass type. In addition, the scanning density can be average density which is calculated on the basis of a read image signal.

In the example illustrated in FIG. 37, the nozzles adjacent to both sides of the simulated non-jetting nozzle are the non-jetting correction nozzles and the non-jetting correction parameters of the simulated non-jetting nozzle are applied to the non-jetting correction nozzles. However, the non-jetting correction nozzle is not limited to this aspect. For example, in addition to the nozzles adjacent to both sides of the simulated non-jetting nozzle, nozzles adjacent to the nozzles may be used as the non-jetting correction nozzles. That is, in a case in which a nozzle with nozzle number i is used as the simulated non-jetting nozzle, nozzles with nozzle numbers i−2, i−1, i+1, and i−2 may be used as the non-jetting correction nozzles.

In this embodiment, before continuous printing starts, the single-non-jetting correction parameters of each nozzle can be calculated in advance, using the single-non-jetting correction parameter calculation chart 250 illustrated in FIG. 37. When a defective nozzle occurs, the defective nozzle can be disabled and correction is performed using the above-mentioned correction parameters such that a streak caused by the defective nozzle is invisible.

The correction parameters of the single-non-jetting correction mode can be generated by the above-mentioned method. The correction parameters of the single-non-jetting correction mode can be used as the correction parameters of the plural-non-jetting correction mode.

Figure 38:
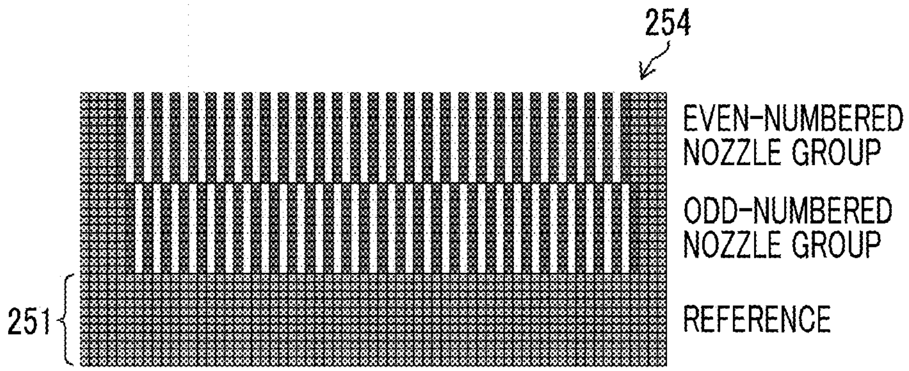
FIG. 38 is a diagram schematically illustrating a plural-non-jetting correction parameter calculation chart.

Alternatively, as illustrated in FIG. 38, a plural-non-jetting correction parameter calculation chart 254 for the plural-non-jetting correction mode may be output and correction parameters for only the plural-non-jetting correction mode may be calculated. In the plural-non-jetting correction parameter calculation chart 254 illustrated in FIG. 38, a pattern having a simulated non-jetting region in which an even-numbered nozzle group is set to the simulated non-jetting nozzles and a pattern having a simulated non-jetting region in which an odd-numbered nozzle group is set to the simulated non-jetting nozzles are arranged in two stages in a solid image region of gradation that is desired to be optimized. In addition, the plural-non-jetting correction parameter calculation chart 254 has the reference density stage 251. The even-numbered nozzle group indicates a nozzle group including nozzles with even-numbered nozzle numbers. The odd-numbered nozzle group indicates a nozzle group including nozzles with odd-numbered nozzle numbers.

The use of the chart illustrated in FIG. 38 makes it possible to calculate accurate correction parameters in the plural-non-jetting correction mode.

[Provision of Defective Nozzle Specification Result Information to User after Streak Detection]

In a case in which a streak is detected by the streak detection process and then the defective nozzle specification process is performed, it is preferable to notify the user of information indicating the detection result of the streak and the result of determining whether the specification of the defective nozzle has failed or succeeded. The control device 100 has an information providing function which visualizes information indicating the processing results and provides the user with the information after the streak detection process and the defective nozzle specification process are performed.

Figure 39:
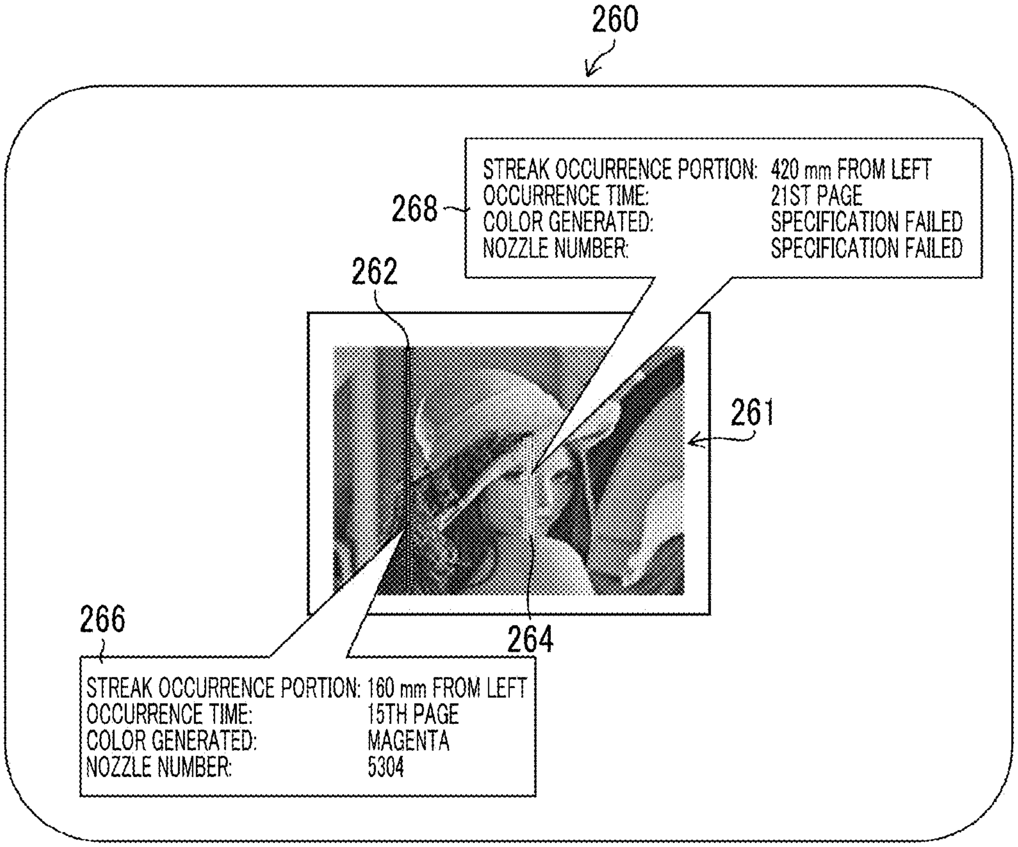
FIG. 39 is an image diagram illustrating an example of the display content of an information display screen that informs a user of the result of determining whether the specification of a defective nozzle succeeds or fails after streak detection.

FIG. 39 is an image diagram illustrating an example of the display content of an information display screen 260 that informs the user of the result of determining whether the specification of a defective nozzle has failed or succeeded after the detection of the streak.

In a case in which the defective nozzle specification process is performed after the detection of a streak, the information display screen 260 illustrated in FIG. 39 is displayed on the display unit 114 described in FIG. 2.

Examples of information items and requirements to be preferably provided to the user are as follows.

<1> The image output by the ink jet printing apparatus is displayed.

<2> A streak detection portion is visualized on the displayed image.

<3> Information indicating the portion in which the streak occurs, information indicating the time when the streak occurs, and information indicating the specification result of the defective nozzle are displayed with respect to each visualized streak.

The information indicating the time when the streak occurs is information indicating a page number in continuous printing. The information indicating the specification result of the defective nozzle includes at least one of information about the ink color generated by the defective nozzle, information about the nozzle number of the defective nozzle, or specification result information about whether the specification of the defective nozzle has succeeded or failed. The ink color generated by the defective nozzle is referred to as a "defective nozzle generation color".

In the example illustrated in FIG. 39, information indicating the content of an output image 261 is displayed at the center of the information display screen 260. In addition, streak visualization information items 262 and 264 in which streaks are visualized are displayed in streak detection portions which are image defect portions on the displayed output image 261. Furthermore, box regions 266 and 268 including the information indicating the portion in which the streak occurs, the information indicating the time when the streak occurs, the information indicating the defective nozzle generation color, and the information indicating the nozzle number of the defective nozzle are displayed in the form of speech balloons for the streak visualization information items 262 and 264, respectively.

The information indicating the position in which the streak occurs is, for example, a distance from the end of the image. FIG. 39 illustrates an example in which, for the streak visualization information 264, the specification of the defective nozzle generation color has failed and the specification of the nozzle number has failed. In addition, information indicating that the specification of the generation color and the nozzle number has failed is displayed. The streak visualization information corresponds to an example of image defect visualization information.

FIG. 39 illustrates an aspect in which all of the information of the output image, the streak visualization information in which the streak detection portion is visualized, the information indicating the portion in which the streak occurs, the information indicating the time when the streak occurs, and information indicating the specification result of the defective nozzle are provided to the user. However, at least one of these information items may be visualized and provided to the user.

The image processing unit 120 described in FIG. 2 generates display data for displaying the information display screen 260 illustrated in FIG. 39 on the display unit 114, using the inspection result of the image inspection unit 140. The image processing unit 120 includes a display data generation unit (not illustrated) that performs a process of generating the display data. The image processing unit 120 including the display unit 114 on which the information display screen 260 illustrated in FIG. 39 is displayed and the processing unit which generates the display data corresponds to an example of an information providing unit.

<<For Process of Interrupting Output of Test Chart During Continuous Printing>>

A process of outputting test charts other than the defective nozzle specification chart during continuous printing, using an interrupt process, is not necessarily used in combination with the defective nozzle specification process (Steps S16 to S22 in FIG. 12 and FIG. 18) described in the first and second embodiments.

Figure 40:
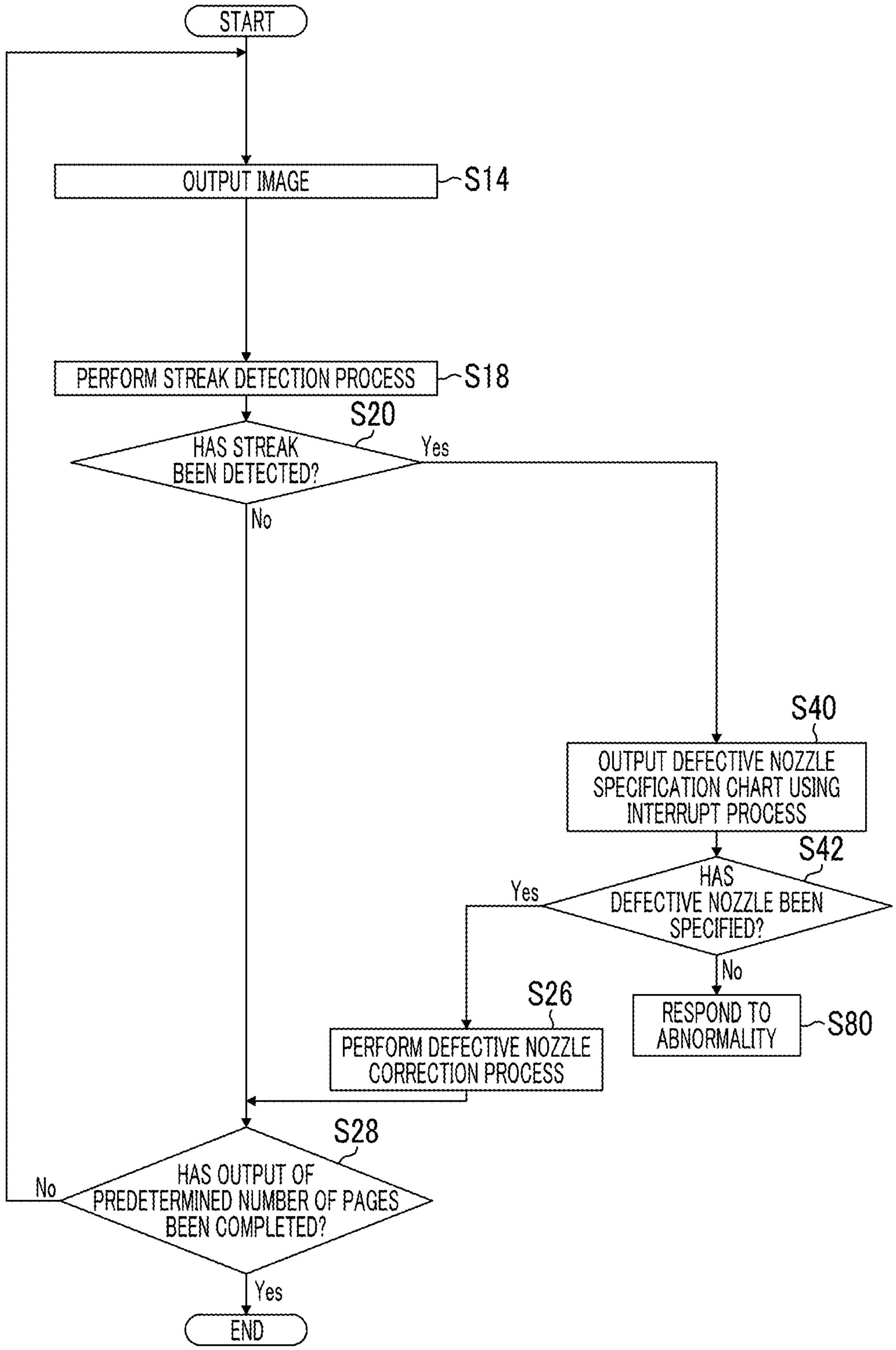
FIG. 40 is a flowchart illustrating another example of the printing process including a test chart output interrupt process.

FIG. 40 is a flowchart illustrating an example of a process flow in a case in which the test chart output interrupt process is not combined with the defective nozzle specification process described in the first and second embodiments and is separately used.

FIG. 40 is a flowchart illustrating another example of the printing process including the test chart output interrupt process.

In the flowchart illustrated in FIG. 40, the same or similar steps as those in the flowchart illustrated in FIG. 12 are denoted by the same step numbers and the description thereof will not be repeated. In FIG. 40, Steps S14 to S20 are the same as Steps S542 to S546 in FIG. 11. When a streak is detected in Step S20 in FIG. 40, the process proceeds to Step S40.

A device structure that performs the flowchart illustrated in FIG. 40 does not require the defective nozzle specification processing unit 146 of the image inspection unit 140 and the defective nozzle detection result history database 160.

According to a processing method following the flowchart illustrated in FIG. 40, it is possible to compensate the disadvantages of the streak detection process described in [Problem 3] and to early perform accurate image quality correction.

Application Examples of Chart Output Interrupt Process

The process of outputting a test chart during continuous printing, using an interrupt process, is referred to as a "chart output interrupt process". The type of test chart output by the chart output interrupt process is not limited to the defective nozzle specification charts illustrated in FIGS. 6 and 7.

The chart output interrupt process may output the single-non-jetting correction parameter calculation chart 250 illustrated in FIG. 37, the plural-non-jetting correction parameter calculation chart 254 illustrated in FIG. 38, other charts, an adjustment chart for adjusting correction parameters for density correction, and various other test charts.

Measures to the case in which a streak is detected by the streak detection process have been mainly described above. However, the technical ideal that, when abnormality occurs in image quality during printing, the test chart is output by the interrupt process to respond to the abnormality can also be applied to image processing other than streak detection. Examples of image quality abnormality other than streaks include granular abnormality, density abnormality, and color abnormality.

The specification includes the disclosure of the following ink jet printing system. That is, when a plurality of images of one or more types are continuously printed by the single pass ink jet method, the ink jet printing system has a function of detecting image quality abnormality during continuous printing and a function of outputting a test chart using an interrupt process during scheduled continuous printing on the basis of the detection result of image quality abnormality.

The function of detecting image quality abnormality during continuous printing performs image analysis, such as a process of comparing the difference between a proper image with a read image obtained by reading an output printed image using the image reading device, to detect the image quality abnormality.

<<Application Examples of Process of Outputting Test Chart Using Overlay Method>>

The process of outputting the test chart using the overlay method described in FIGS. 20 to 26 is not necessarily used in combination with the defective nozzle specification process (Steps S16 to S22 in FIGS. 12 and 18) described in the first and second embodiments. In addition, the process of outputting the test chart using the overlay method is not necessarily performed in the chart output interrupt process.

The process of outputting the test chart using the overlay method may not be combined with the defective nozzle specification process described in the first and second embodiments and may be performed at an appropriate time other than the chart output interrupt process.

Figure 41:
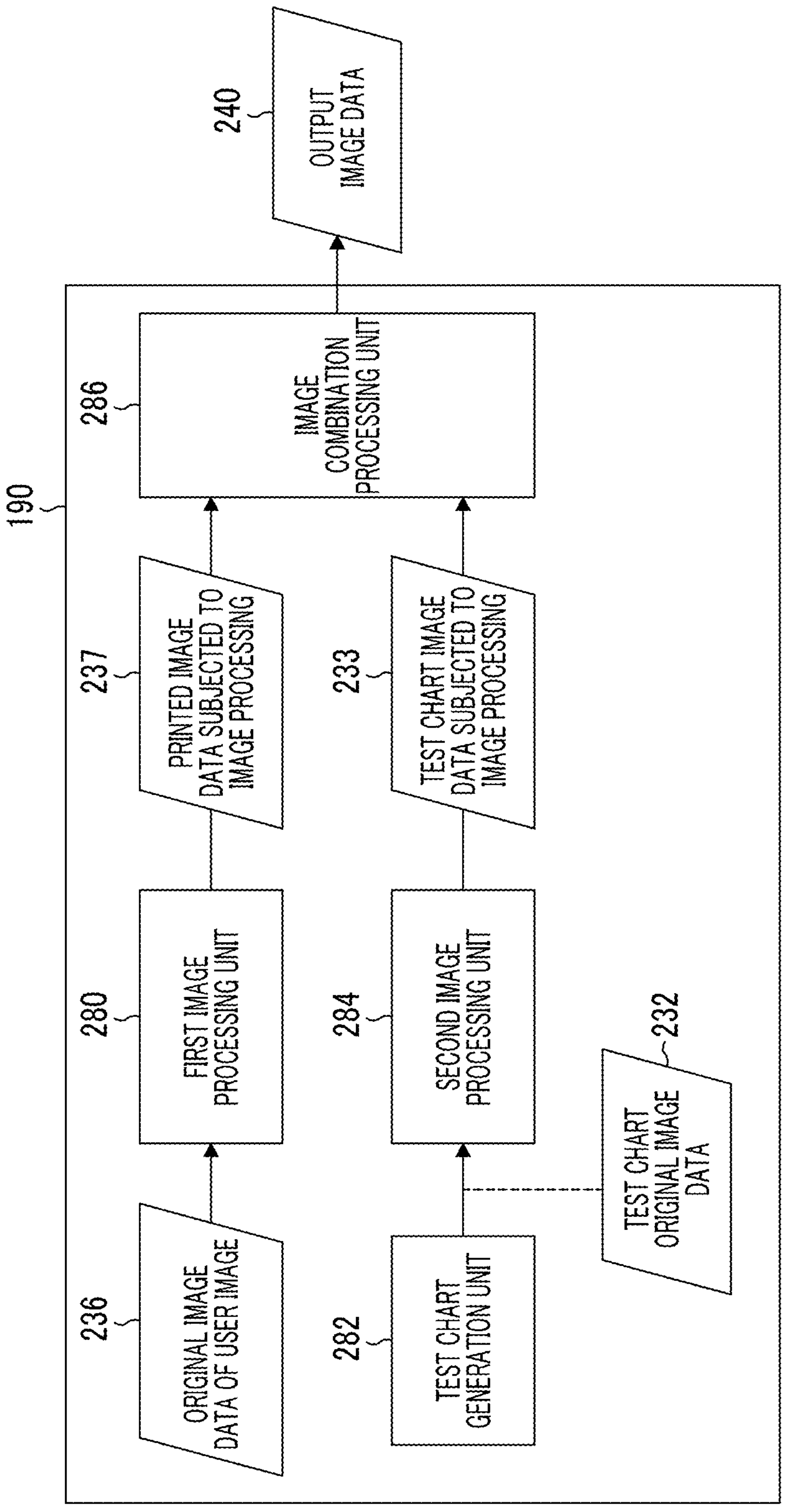
FIG. 41 is a block diagram providing the function of an output image data generation unit for outputting a test chart using the overlay method.

FIG. 41 is a block diagram providing the function of an output image data generation unit 190 for outputting the test chart using the overlay method.

The output image data generation unit 190 includes a first image processing unit 280, a test chart generation unit 282, a second image processing unit 284, and an image combination processing unit 286.

The first image processing unit 280 performs various kinds of image processing described in Step S64 of FIG. 21 for user image original image data 236. Printed image data 237 subjected to the image processing which has been generated by the process of the first image processing unit 280 is transmitted to the image combination processing unit 286.

The test chart generation unit 282 generates original image data of a test chart for overlay. The test chart generation unit 282 may adaptively generate test chart original image data 232 on the basis of the streak detection information detected from the printed image, as described in Step S52 of FIG. 21, or may provide test chart original image data which has been prepared in advance. The test chart generation unit 282 may include a storage unit that stores the test chart original image data prepared in advance.

The second image processing unit 284 performs various kinds of image processing described in Step S54 of FIG. 21 for the test chart original image data 232. The same image processing as the first image processing performed by the first image processing unit 280 or image processing different from the first image processing may be applied as the second image processing performed by the second image processing unit 284. As described in FIG. 21, it is preferable that the content of the first image processing is different from the content of the second image processing.

Test chart image data 233 subjected to the image processing which has been generated by the process of the second image processing unit 284 is transmitted to the image combination processing unit 286.

The image combination processing unit 286 performs the overlay process described in Step S66 of FIG. 21. The image combination processing unit 286 combines the printed image data 237 subjected to the image processing with the test chart image data 233 subjected to the image processing to generate output image data 240. The image recording control unit 124 illustrated in FIG. 2 controls the ink jet operation of the ink jet heads 46C, 46M, 46Y, and 46K on the basis of the output image data 240 such that an image is drawn.

<<For Program Causing Computer to Function as Image Inspection Device>>

A program that causes a computer to implement an image processing function including the image inspection function described in the above-mentioned embodiments and the control function of the ink jet printing apparatus can be recorded on a computer readable medium, such as a compact disc read-only memory (CD-ROM), a magnetic disk, or other tangible and non-transitory information storage media, and the program can be provided through the information storage medium. Instead of the aspect in which the program is stored in the tangible and non-transitory information storage medium and then provided, program signals may be provided as a download service through a communication network such as the Internet.

In addition, a service may be performed which provides a portion of or the entire image processing function including the image inspection function as an application server and provides the processing function through a communication network.

<<Ink Jetting Method of Ink Jet Head>>

An ejector of the ink jet head includes a nozzle that jets a liquid, a pressure chamber that is connected to the nozzle, and a jetting energy generation element that applies jetting energy to the liquid in the pressure chamber. For a jetting method which jets liquid droplets from the nozzle of the ejector, means for generating jetting energy is not limited to a piezoelectric element and various jetting energy generation elements, such as a heating element and an electrostatic actuator, can be applied. For example, a method can be used which jets liquid droplets using the pressure of film boiling caused by the heating of a liquid by a heating element. A jetting energy generating element corresponding to the jetting method of a liquid jetting head is provided in a flow path structure.

<<For Recording Medium>>

The "recording medium" means a "medium" used to record an image. The "recording medium" or the "medium" is a general term of various media, such as a sheet, a recording sheet, a printing sheet, a printing medium, a printed medium, an image formation medium, an image-formed medium, an image receiving medium, and a medium to which liquid droplets are jetted. For example, the material or shape of the recording medium is not particularly limited. Various sheets, such as a seal sheet, a resin sheet, a film, fabric, a non-woven fabric, and other materials, may be used, regardless of the material or shape of the recording medium. The recording medium is not limited to the sheet-type medium and may be a continuous medium such as continuous paper. In a case in which the continuous medium is used, the concept of the printing of "a plurality of pages" means that printing is performed on different regions of the continuous medium a plurality of times. In addition, in a case in which the continuous medium is used, an inter-image region formed between the user image regions corresponds to a blank portion and the inter-image region can be the first region in which the defective nozzle detection pattern is recorded.

The sheet-type recording medium is not limited to a cut sheet which has been cut into a prescribed size in advance. The continuous medium may be cut into the sheet-type recording media with a prescribed size at any time.

<<For Recording Medium Transport Means>>

Transport means for transporting the recording medium is not limited to the drum transport type illustrated in FIG. 1 and various transport types, such as a belt transport type, a nip transport type, a chain transport type, and a pallet transport type, can be used. In addition, these types can be appropriately combined with each other.

Modification Example 1

In the above-described embodiments, as an example of the image quality correction process, the non jetting correction parameters are applied to image data before halftone processing to correct a signal value and halftone processing is performed for the corrected image data. However, when the invention is embodied, a structure in which data after halftone processing is corrected may be used. In addition, a driving signal that is applied to the jetting energy generation element of each nozzle may be corrected.

Modification Example 2

In the above-described embodiments, an example in which the Y direction which is the scanning direction in the single pass method is the first direction and the X direction which is the nozzle column direction perpendicular to the first direction is the second direction has been described. However, the second direction may be a direction perpendicular to the first direction. In the specification, the term "perpendicular" or "vertical" includes an aspect in which the same operation and effect as those in a case in which two directions substantially intersect with each other at an angle of 90° are obtained among the aspects in which two directions intersect each other at an angle less than 90° or at an angle greater than 90°.

For Terms

The term "printing apparatus" is synonymous with the terms, such as a printing machine, a printer, a typewriter, an image recording apparatus, an image formation apparatus, an image output apparatus, and a drawing apparatus.

The term "image" is construed broadly and includes a color image, a black-and-white image, a monochromatic image, a gradation image, and a uniform-density (solid) image. The "image" is not limited to a photographed image and is used as the all-encompassing term including a design, a letter, a sign, a drawing line, a mosaic pattern, a coloring pattern, and various other patterns, or combinations thereof.

The "user image" indicates an image which is designated as an object to be printed by the user.

The "image recording" includes the concept of the terms, such as image formation, printing, typing, drawing, and print.

The term "during continuous printing" means for the period for which a plurality of images of one or more types are continuously printed.

For Combinations of Embodiments and Modification Examples

The configurations described in the above-mentioned embodiments and the matters described in the above-mentioned modification examples may be appropriately combined with each other and some of them may be substituted.

In the above-described embodiments of the invention, the components may be appropriately changed, added or deleted without departing from the scope of the invention. The invention is not limited to the above-described embodiments and may be variously modified by those skilled in the art within the technical scope and spirit of the invention.

EXPLANATION OF REFERENCES

1A: ink jet printing apparatus
10: sheet feed unit
12: sheet feed device
12A: sheet feed base
14: feeder board
16: sheet feed drum
20: treatment liquid applying unit
22: treatment liquid applying drum
23, 33, 43, 74: gripper
24: treatment liquid applying device
30: treatment liquid drying unit
32: treatment liquid drying drum
34: warm air blower
40: drawing unit
42: drawing drum
44: head unit
46C, 46M, 46Y, 46K: ink jet head
48: image reading device
50: ink drying unit
60: stacking unit
62: stacking device
62A: stacking tray
70: chain gripper
72: chain
80: sheet guide
82: first sheet guide
84: second sheet guide
90: warm air blowing unit
100: control device
101: ink jet printing system
110: system controller
112: communication unit
114: display unit
116: operation unit
118: information storage unit
120: image processing unit
122: transport control unit
124: image recording control unit
130: CPU
132: ROM
134: RAM
140: image inspection unit
142: defective nozzle detection processing unit
144: streak detection processing unit
146: defective nozzle specification processing unit
150: medium transport mechanism
152: rotary encoder
160: defective nozzle detection result history database
162A, 162B, 164: frame
172: image acquisition unit
174: memory
176: read image acquisition unit
178: database storage unit
180: information output unit
190: output image data generation unit
192: defective nozzle detection pattern generation unit
193: defective nozzle specification chart generation unit
194: correction processing unit
196: halftone processing unit
198: data addition processing unit
200: defective nozzle detection pattern region extraction unit
202: image analysis unit
204: defective nozzle detection result information
210: measured image extraction unit
212: proper image storage unit
214: difference information generation unit
216: streak determination unit
220: approximate nozzle number estimation unit
222: ink color estimation unit
224: history data collation unit
226: defective nozzle determination unit
228: defective nozzle information storage unit
230C: test chart
230K: test chart
230M: test chart
232: test chart original image data

233: test chart image data
236: original image data
237: printed image data
238: dot pattern image
240: output image data
250: single-non-jetting correction parameter calculation chart
251: reference density stage
254: plural-non-jetting correction parameter calculation chart
260: information display screen
261: output image
262, 264: streak visualization information
266, 268: box region
280: first image processing unit
282: test chart generation unit
284: second image processing unit
286: image combination processing unit
460: line head
462: nozzle
464: nozzle column
472: dot
502: user image
504, 504C, 504K, 504M, 504Y: ladder pattern
506: line
511, 512, 513, 514, 515, 516, 517, 518: printed matter
530: proper image
532, 542: user image region
540: measured image
544, 546: streak
550: streak information
560: read image
Nz3: third nozzle
Nz8: eighth nozzle
P: sheet
S12 to S28, S40 to S44, S80: step of printing process including process of image inspection method according to embodiment
S52 to S66: step of defective nozzle specification chart generation process
S101 to S105: step of defective nozzle specification process according to embodiment
S512 to S522: step of printing process of performing defective nozzle specification process during continuous printing
S542 to S550: step of streak detection process performed during continuous printing

What is claimed is:

1. An image inspection device comprising:

a read image acquisition unit that acquires data of read images obtained by reading a defective nozzle detection pattern which is recorded in a first region of a recording medium by a single pass ink jet printing apparatus and a printed image which is recorded in a second region different from the first region in the recording medium by the ink jet printing apparatus, using an image reading device;

a defective nozzle detection processing unit that analyzes data of a first read image, which is the read image of the defective nozzle detection pattern, to detect a defective nozzle of a line-type ink jet head used to record the defective nozzle detection pattern;

a history information storage unit that stores a history of a detection result of the defective nozzle obtained by the defective nozzle detection processing unit;

an image defect detection processing unit that analyzes data of a second read image, which is the read image of the printed image, to detect an image defect of the printed image; and a defective nozzle specification processing unit that collates information about the image defect detected by the image defect detection processing unit with history information stored in the history information storage unit to specify a defective nozzle causing the image defect.

2. The image inspection device according to claim 1, wherein, during continuous printing in which the ink jet printing apparatus continuously prints a plurality of printed images of one or more types, a process of acquiring the data of the read image, a process of detecting the defective nozzle, a process of storing the history of the detection result of the defective nozzle, a process of detecting the image defect, and a process of specifying the defective nozzle are performed.

3. The image inspection device according to claim 1, wherein the defective nozzle specification processing unit performs a process of specifying the defective nozzle from the history information, using at least one of estimation information of an ink color obtained by estimating an ink color causing the image defect from color analysis for the information about the image defect detected by the image defect detection processing unit, estimation information of an approximate nozzle number obtained by estimating an approximate nozzle number of a nozzle causing the image defect from coordinate analysis for the information about the image defect detected by the image defect detection processing unit, or time information indicating a time when the image defect detected by the image defect detection processing unit occurs.

4. The image inspection device according to claim 3, wherein the defective nozzle specification processing unit comprises:

an ink color estimation unit that performs the color analysis for the information about the image defect detected by the image defect detection processing unit to estimate the ink color causing the image defect;

an approximate nozzle number estimation unit that performs the coordinate analysis for the information about the image defect detected by the image defect detection processing unit to estimate the approximate nozzle number of the nozzle causing the image defect;

a history data collation unit that extracts one or more data items including the latest data among the data items of the detection result of the defective nozzle of the ink color estimated by the ink color estimation unit from the history information, on the basis of the estimation information of the estimated ink color, and extracts data of the detection result of the defective nozzle in a range of nozzles with a plurality of consecutive nozzle numbers including the approximate nozzle number estimated by the approximate nozzle number estimation unit from the history information; and a defective nozzle determination unit that specifies the defective nozzle from the data extracted by the history data collation unit.

5. The image inspection device according to claim 1, further comprising:

an information providing unit that, after the process of detecting the image defect and the process of specifying the defective nozzle are performed, visualizes information indicating the processing results and provides the information to a user, wherein the information providing unit provides one or more information items among an output image which is output by the ink jet printing apparatus, image defect visualization information obtained by visualizing an image defect portion detected by the image defect detection processing unit on the output image, information indicating a portion in which the image defect occurs, information indicating the time when the image defect occurs, and information indicating a specification result of the defective nozzle by the process of specifying the defective nozzle.

6. The image inspection device according to claim 1, wherein the image defect is a streak defect extending in a scanning direction which is a direction in which the ink jet head and the recording medium are moved relative to each other when recording is performed by a single pass method.

7. An ink jet printing system comprising:

a single pass ink jet printing apparatus;

an image reading device that is provided in the ink jet printing apparatus;

a control device that controls an operation of the ink jet printing apparatus; and the image inspection device according to claim 1.

8. The ink jet printing system according to claim 7, further comprising:

a correction processing unit that, in a case in which a defective nozzle causing the image defect is specified, performs an image quality correction process of preventing the image defect caused by the defective nozzle.

9. The ink jet printing system according to claim 7, wherein, in a case in which the defective nozzle has not been specified by a process of the defective nozzle specification processing unit during continuous printing in which the ink jet printing apparatus continuously prints a plurality of printed images of one or more types, the control device controls an interrupt process of outputting a test chart during the continuous printing, using an interrupt.

10. The ink jet printing system according to claim 9, wherein at least one of the test charts output by the interrupt process is a defective nozzle specification chart including a line pattern for specifying the defective nozzle, and the control device reflects an analysis result of data of a third read image, which is obtained by reading the output defective nozzle specification chart using the image reading device, in a process of printing the printed image during the continuous printing after the test chart is output by the interrupt process.

11. The ink jet printing system according to claim 9, wherein at least one of the test charts output by the interrupt process is a chart formed by a composite image obtained by incorporating a test chart into one or more types of printed images which are scheduled to be output during the continuous printing.

12. The ink jet printing system according to claim 11, further comprising:

a first image processing unit that applies first image processing to at least one of the one or more types of printed images scheduled to be output during the continuous printing to generate image data subjected to the first image processing;

a second image processing unit that applies second image processing to data of a test chart for interrupt output to generate image data subjected to the second image processing; and an image combination processing unit that applies an image combination process to the image data subjected to the first image processing and the image data subjected to the second image processing to generate composite image data.

13. The ink jet printing system according to claim 12, further comprising:

a test chart generation unit that generates data of the test chart for interrupt output, on the basis of detection information of the image defect detected by the image defect detection processing unit.

14. The ink jet printing system according to claim 12, wherein the content of the first image processing is different from the content of the second image processing.

15. The ink jet printing system according to claim 9, wherein at least one of the test charts output by the interrupt process is an adjustment chart for adjusting a correction parameter that is used for an image correction process of preventing a streak defect which is the image defect, and the control device reflects an analysis result of data of a fourth read image, which is obtained by reading the output adjustment chart using the image reading device, in the process of printing the printed image during the continuous printing after the test chart is output by the interrupt process.

16. The ink jet printing system according to claim 9, wherein the content of a first image quality correction process which is applied to the printed image to be output after the specification of the defective nozzle succeeds in a case in which the specification of the defective nozzle causing the image defect has succeeded and prevents the image defect is different from the content of a second image quality correction process which is applied to the printed image to be output after the specification of the defective nozzle succeeds in a case in which the specification of the defective nozzle causing the image defect has failed and prevents the image defect.

17. An image inspection method comprising:

a read image acquisition step of acquiring data of read images obtained by reading a defective nozzle detection pattern which is recorded in a first region of a recording medium by a single pass ink jet printing apparatus and a printed image which is recorded in a second region different from the first region in the recording medium by the ink jet printing apparatus, using an image reading device;

a defective nozzle detection processing step of analyzing data of a first read image, which is the read image of the defective nozzle detection pattern, to detect a defective nozzle of a line-type ink jet head used to record the defective nozzle detection pattern;

a history information storage step of storing a history of a detection result of the defective nozzle obtained in the defective nozzle detection processing step in a history information storage unit;

an image defect detection processing step of analyzing data of a second read image, which is the read image of the printed image, to detect an image defect of the printed image; and a defective nozzle specification processing step of collating information about the image defect detected in the image defect detection processing step with history information stored in the history information storage unit to specify a defective nozzle causing the image defect.

18. A non-transitory computer-readable tangible recording medium including a program that causes a computer to perform:

a read image acquisition step of acquiring data of read images obtained by reading a defective nozzle detection pattern which is recorded in a first region of a recording medium by a single pass ink jet printing apparatus and a printed image which is recorded in a second region different from the first region in the recording medium by the ink jet printing apparatus, using an image reading device;

a defective nozzle detection processing step of analyzing data of a first read image, which is the read image of the defective nozzle detection pattern, to detect a defective nozzle of a line-type ink jet head used to record the defective nozzle detection pattern;

a history information storage step of storing a history of a detection result of the defective nozzle obtained in the defective nozzle detection processing step in a history information storage unit;

an image defect detection processing step of analyzing data of a second read image, which is the read image of the printed image, to detect an image defect of the printed image; and a defective nozzle specification processing step of collating information about the image defect detected in the image defect detection processing step with history information stored in the history information storage unit to specify a defective nozzle causing the image defect.

* * * * *